US012649006B2

(12) United States Patent
Fyffe-Maricich et al.

(10) Patent No.: US 12,649,006 B2
(45) Date of Patent: Jun. 9, 2026

(54) GENE THERAPY FOR TREATING CDKL5 DEFICIENCY DISORDER

(71) Applicant: Ultragenyx Pharmaceutical Inc., Novato, CA (US)

(72) Inventors: Sharyl Lynne Fyffe-Maricich, Novato, CA (US); Matthew Scott Fuller, Millis, MA (US); Margaret Caroline Wright, San Rafael, CA (US); Lorelei Ioana Stoica, Acton, MA (US); Stewart Craig, Cambridge, MA (US); Sean Christopher Daugherty, Petaluma, CA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 969 days.

(21) Appl. No.: 17/796,064

(22) PCT Filed: Feb. 11, 2021

(86) PCT No.: PCT/US2021/017656
§ 371 (c)(1),
(2) Date: Jul. 28, 2022

(87) PCT Pub. No.: WO2021/163322
PCT Pub. Date: Aug. 19, 2021

(65) Prior Publication Data
US 2023/0054144 A1 Feb. 23, 2023

Related U.S. Application Data

(60) Provisional application No. 63/090,492, filed on Oct. 12, 2020, provisional application No. 62/976,483, filed on Feb. 14, 2020.

(51) Int. Cl.
| | |
|---|---|
| *A61K 48/00* | (2006.01) |
| *A61K 31/573* | (2006.01) |
| *A61K 35/761* | (2015.01) |
| *A61P 25/28* | (2006.01) |

(52) U.S. Cl.
CPC ........ *A61K 48/0058* (2013.01); *A61K 31/573* (2013.01); *A61K 35/761* (2013.01); *A61K 48/0075* (2013.01); *A61P 25/28* (2018.01)

(58) Field of Classification Search
CPC ..... A61K 48/00; A61K 48/0058; C12N 15/86
See application file for complete search history.

(56) References Cited

U.S. PATENT DOCUMENTS

| | | | |
|---|---|---|---|
| 6,309,634 | B1 | 10/2001 | Bankiewicz et al. |
| 6,759,050 | B1 | 7/2004 | Sista et al. |
| 6,764,845 | B2 | 7/2004 | Sista et al. |
| 6,953,575 | B2 | 10/2005 | Bankiewicz et al. |
| 7,282,199 | B2 | 10/2007 | Gao et al. |
| 7,534,613 | B2 | 5/2009 | Bankiewicz et al. |
| 7,598,070 | B2 | 10/2009 | Sista et al. |
| 7,790,449 | B2 | 9/2010 | Gao et al. |
| 8,192,975 | B2 | 6/2012 | Sista et al. |
| 8,309,355 | B2 | 11/2012 | Bankiewicz et al. |
| 8,734,809 | B2 | 5/2014 | Gao et al. |
| 8,852,607 | B2 | 10/2014 | Sista et al. |
| 8,927,514 | B2 | 1/2015 | Chatterjee et al. |
| 9,051,542 | B2 | 6/2015 | Wright et al. |
| 9,492,415 | B2 | 11/2016 | Bankiewicz et al. |
| 9,506,083 | B2 | 11/2016 | Arbetman et al. |
| 9,585,971 | B2 | 3/2017 | Deverman et al. |
| 9,587,282 | B2 | 3/2017 | Schaffer et al. |
| 9,611,302 | B2 | 4/2017 | Srivastava et al. |
| 9,725,485 | B2 | 8/2017 | Srivastava et al. |
| 9,856,539 | B2 | 1/2018 | Schaffer et al. |
| 9,909,142 | B2 | 3/2018 | Yazicioglu et al. |
| 9,920,097 | B2 | 3/2018 | Zhong et al. |
| 10,011,640 | B2 | 7/2018 | Srivastava et al. |
| 10,081,659 | B2 | 9/2018 | Chiorini et al. |
| 10,179,176 | B2 | 1/2019 | Kay et al. |
| 10,202,657 | B2 | 2/2019 | Schaffer et al. |
| 10,214,566 | B2 | 2/2019 | Schaffer et al. |
| 10,214,785 | B2 | 2/2019 | Schaffer et al. |
| 10,266,845 | B2 | 4/2019 | Cronin et al. |
| 10,294,281 | B2 | 5/2019 | Srivastava et al. |
| 10,301,648 | B2 | 5/2019 | Vandenberghe et al. |
| 10,385,320 | B2 | 8/2019 | Kay et al. |

(Continued)

FOREIGN PATENT DOCUMENTS

| | | | |
|---|---|---|---|
| EP | 1310571 | B1 | 5/2003 |
| WO | WO-2003/042397 | A2 | 5/2003 |

(Continued)

OTHER PUBLICATIONS

Gao et al. Brain 2020 143:811-832 (Year: 2020).*

(Continued)

*Primary Examiner* — Marcia S Noble
(74) *Attorney, Agent, or Firm* — Antheros Legal Advisors LLP

(57) ABSTRACT

This present disclosure provides adeno-associated viral vectors, recombinant adeno-associated vims (rAAV), and methods of their use in gene therapy for treating CDKL5 deficiency disorder (CDD). Also provided are pharmaceutical compositions comprising an rAAV of the invention and a pharmaceutically acceptable carrier or excipient. These pharmaceutical compositions may be useful in gene therapy for the treatment of CDD caused by mutations in CDKL.

15 Claims, 16 Drawing Sheets

Specification includes a Sequence Listing.

(56) References Cited

U.S. PATENT DOCUMENTS

| | | | |
|---|---|---|---|
| 10,392,632 | B2 | 8/2019 | Wright et al. |
| 10,532,110 | B2 | 1/2020 | Gray et al. |
| 10,561,743 | B2 | 2/2020 | Gray et al. |
| 11,491,242 | B2 | 11/2022 | Gray et al. |
| 2007/0036760 | A1 | 2/2007 | Wilson et al. |
| 2009/0197338 | A1 | 8/2009 | Vandenberghe et al. |
| 2011/0229971 | A1 | 9/2011 | Knop et al. |
| 2012/0100606 | A1 | 4/2012 | Zolotukhin et al. |
| 2012/0135515 | A1 | 5/2012 | Qu et al. |
| 2013/0072548 | A1 | 3/2013 | Wright et al. |
| 2015/0344911 | A1 | 12/2015 | Chatterjee et al. |
| 2018/0023070 | A1 | 1/2018 | Kjellman et al. |
| 2018/0037962 | A1 | 2/2018 | Kjellman et al. |
| 2019/0060400 | A1 | 2/2019 | During |
| 2025/0011810 | A1 | 1/2025 | Wei et al. |

FOREIGN PATENT DOCUMENTS

| | | | |
|---|---|---|---|
| WO | WO-2014/186579 | A1 | 11/2014 |
| WO | WO-2015/128746 | A2 | 9/2015 |
| WO | WO-2016/049230 | A1 | 3/2016 |
| WO | WO-2017/134274 | A1 | 8/2017 |
| WO | WO-2017/136202 | A1 | 8/2017 |
| WO | WO-2017/153834 | A1 | 9/2017 |
| WO | WO-2017/165859 | A1 | 9/2017 |
| WO | WO-2018/005617 | A2 | 1/2018 |
| WO | WO-2018/022905 | A2 | 2/2018 |
| WO | WO-2018/156654 | A1 | 8/2018 |
| WO | WO-2018/213786 | A1 | 11/2018 |
| WO | WO-2018/222503 | A1 | 12/2018 |
| WO | WO-2018/226602 | A1 | 12/2018 |
| WO | 201909406 | A1 | 1/2019 |
| WO | WO-2019/108924 | A2 | 6/2019 |
| WO | WO-2019/168961 | A1 | 9/2019 |
| WO | 2020023612 | A1 | 1/2020 |
| WO | WO-2020/016318 | A1 | 1/2020 |
| WO | WO-2020/159970 | A1 | 8/2020 |
| WO | 2020214929 | A1 | 10/2020 |
| WO | WO-2021/067598 | A1 | 4/2021 |
| WO | WO-2021/081135 | A2 | 4/2021 |
| WO | WO-2021/087282 | A1 | 5/2021 |
| WO | 2021154923 | A2 | 8/2021 |
| WO | WO-2021/222118 | A1 | 11/2021 |
| WO | 2023023590 | A1 | 2/2023 |

OTHER PUBLICATIONS

Liguore et al. 2019 Molecular Therapy 27(11):2018-2037 (Year: 2019).*

Altschul et al. (1990) "Basic Local Alignment Search Tool," J. Mol. Biol. 215:403-410.

Choi et al. (2005) "AAV hybrid serotypes: improved vectors for gene delivery," Curr Gene Ther. 5(3):299-310 (20 pages).

Clark (2002) "Recent advances in recombinant adeno-associated virus vector production," Kidney International 61:S9-S15.

Daya et al. (2008) "Gene Therapy Using Adeno-Associated Virus Vectors," Clinical Microbiology Reviews 21(4):583-593 (19 pages).

Del Rosso et al. (2017) "Genetic diseases with impaired central respiratory control," The EuroBiotech Journal 1(2):122-127.

Gao et al. (2005), "New Recombinant Serotypes of AAV Vectors," Current Gene Therapy 5(3):285-297.

Gao et al., Abstract #OR15, ESGCT XXV Anniversary Congress in Collaboration with German Society for Gene Therapy, Oct. 17-20, 2017, Berlin, Germany (3 pages).

Gao Y. et al. (2017) "Gene therapy with AAV-CDKL5 vectors in models of CDKL5 disorder," Human Gene therapy Mary Ann Liebert Inc. NLD, 28(12), XP055809246 ISSN:1557-7422 (1 page).

Ghosh et al. (2006) Long-term correction of murine glycogen storage disease type la by recombinant adeno-associated virus-1-mediated gene transfer, Gene Therapy 13(4):321-329.

Hector et al. (2017) "CDKL5 variants: Improving our understanding of a rare neurologic disorder," Neurology:Genetics (11 pages).

Howden et al. (2008) "The transient expression of mRNA coding for Rep protein from AAV facilitates targeted plasmid integration," J Gene Med 10(1):42-50.

International Search Report and Written Opinion for PCT/US2021/017656 mailed Jun. 15, 2021 (15 pages).

Lin et al. (2005) "CDKL5/Stk9 kinase inactivation is associated with neuronal developmental disorders," Human Molecular Genetics 14(24):3775-3786.

McLean et al. (2014) "Widespread neuron-specific transgene expression in brain and spinal cord following synapsin promoter-driven AAV9 neonatal intracerebroventricular injection," Neuroscience Letters 576:73-78.

Mignone F. et al. (2002) "Untranslated regions of mRNAs" Genome Biol 3:REVIEWS0004 (10 pages).

Nakai et al. (2003) "AAV serotype 2 vectors preferentially integrate into active genes in mice," Nature Genetics 34(3):297-302.

Olson et al. (2019) "Cyclin-Dependent Kinase-Like 5 Deficiency Disorder: Clinical Review," Pediatric Neurology 97:18-25.

Philpott et al. (2002) "Efficient Integration of Recombinant Adeno-Associated Virus DNA Vectors Requires a p5-rep Sequence in cis," Journal of Virology 76(11):5411-5421.

Russo et al. (2009) "Novel mutations in the CDKL5 gene, predicted effects and associated phenotypes," Neurogenetics 10(3):241-250.

The CDKL5 gene homepage Global Variome shared LOVD, https://databases.lovd.nl/shared/genes/CDKL5, retrieved on Feb. 3, 2023 (1 page).

Yuan et al. 2011 "A Versatile Adeno-Associated Virus Vector Producer Cell Line Method for Scalable Vector Production of Different Serotypes," Human Gene Therapy 22:613-624.

Wilson, "Challenges of gene therapy and editing to the Cns," CDKL5 Forum Presentation, Nov. 5, 2019, pp. 1-14.

Schmid et al., "Evaluation of CDKL5 Gene Therapy in CDD Mouse Models," CDKL5 Forum Presentation Poster, Nov. 2019, p. 1.

Wright, "AAV9/hCDKL5 Delivery to Cerebrospinal Fluid of Juvenile CDKL5-Deficient Mice Improves Learning and Memory and Motor Function in Adult Mice," American Society of Gene & Cell Therapy Presentation, May 12, 2020, pp. 1-12.

Wright et al., "AAV9/hCDKL5 Delivery to Cerebrospinal Fluid of Juvenile CDKL5-Deficient Mice Improves Learning and Memory and Motor Function in Adult Mice," Molecular Therapy vol. 28 No 4S1, Apr. 28, 2020 (2 pages).

Gao, Y. "Gene Therapy with AAV-CDKL5 Vectors in Models of CDKL5 Disorder," Submitted for the Degree of Doctor of Philosophy, Oct. 2018, Department of Medicine, Imperial College London (260 pages).

Chai, Z, et al., Optimization of Dexamethasone Administration for Maintaining Global Transduction Efficacy of Adeno-Associated Virus Serotype 9, Hum Gene Ther, 30(7): 829-840 (2019).

Genbank, Accession No. NM_001323289, pp. 1-7 (2019) retrieved on Jan. 25, 2025 at <https://www.ncbi.nlm.nih.gov/nuccore/1653614648?sat=48&satkey=28800153>.

Gray, S.J., et al., Optimizing promoters for recombinant adeno-associated virus-mediated gene expression in the peripheral and central nervous system using self-complementary vectors, Hum Gene Ther, 22(9): 1143-1153 (2011).

Sehara, Y., et al., Efficient transduction of adeno-associated virus vectors into gerbil hippocampus with an appropriate combination of viral capsids and promoters, Neurosci Lett, 682: 27-31 (2018).

Shevtsova, Z. et al., Promoters and serotypes: targeting of adeno-associated virus vectors for gene transfer in the rat central nervous system in vitro and in vivo, Exp Physiol, 90(1): 53-59 (2005).

Tanaka, T., et al., Pre-clinical study of the CDKL5 gene replacement therapy tested on the Cdkl5 knockout mouse, Brain and Development, 51(suppl), S231: E-037.

Thiel, G., et al., Characterization of tissue-specific transcription by the human synapsin I gene promoter, Proc Natl Acad Sci USA, 88(8):3431-3435 (1991).

Zhu, Y-C., et al., Molecular and Synaptic Bases of CDKL5 Disorder, Dev Neurobiol, 79(1): 8-12 (2019).

Bodratti, A.M., et al., Formulation of Poloxamers for Drug Delivery, J Funct Biomater, 9(1): 11, pp. 1-24 (2018).

(56)                    References Cited

OTHER PUBLICATIONS

Dufour, J.P., et al., Hydrocephalus after Intrathecal Administration of Dextran to Rhesus Macaques (*Macaca mulatta*), Comp Med, 68(3): 227-232 (2018).

Gray, S.J., et al., Global CNS gene delivery and evasion of anti-AAV-neutralizing antibodies by intrathecal AAV administration in non-human primates, Gene Ther, 20(4): 450-459 (2013), 22 pages.

Hadaczek, P., et al., Widespread AAV1- and AAV2-mediated transgene expression in the nonhuman primate brain: implications for Huntington's disease, Mol Ther Methods Clin Dev, 3: 16037, pp. 1-11 (2016).

Samulski, R.J., et al., AAV-Mediated Gene Therapy for Research and Therapeutic Purposes, Annu Rev Virol, 1(1): 427-451 (2014).

Wang, D., et al., Adeno-associated virus vector as a platform for gene therapy delivery, Nat Rev Drug Discov, 18(5): 358-378 (2019), 61 pages.

PCT/US2022/075130 International Search Report and Written Opinion mailed Nov. 3, 2022, 10 pages.

* cited by examiner

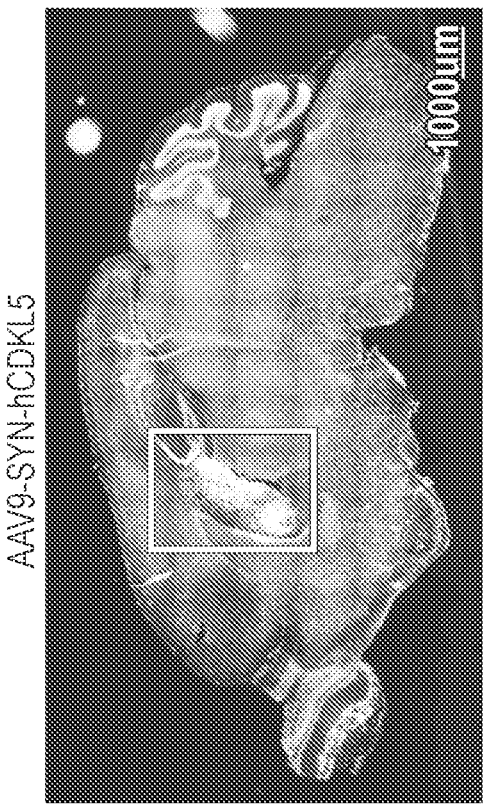
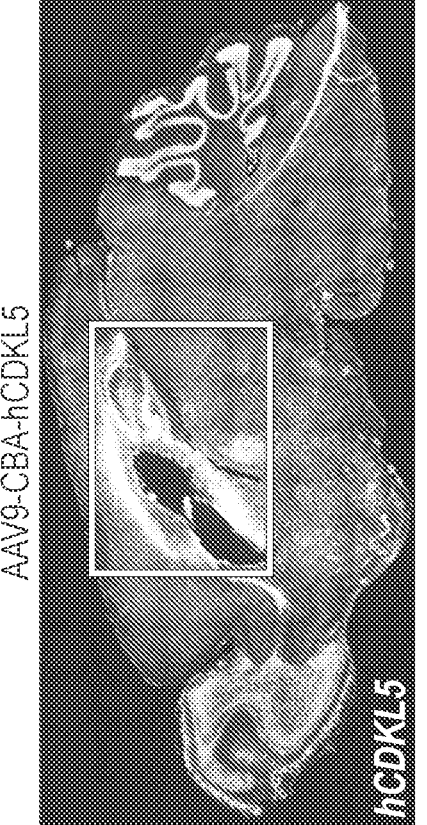
FIG. 6A

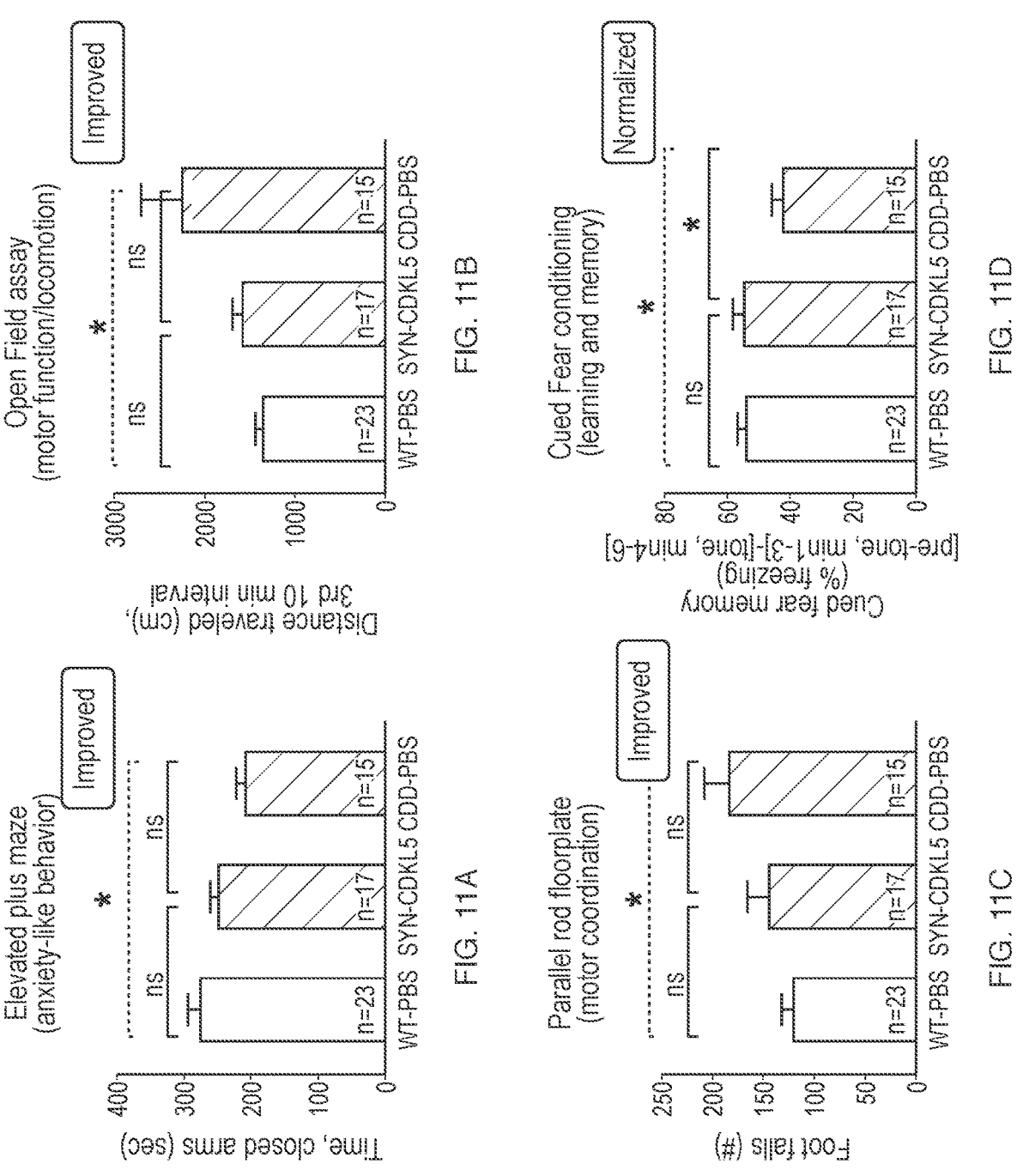

SEQUENCE LISTING

```
<160> NUMBER OF SEQ ID NOS: 24

<210> SEQ ID NO 1
<211> LENGTH: 2880
<212> TYPE: DNA
<213> ORGANISM: Homo sapiens

<400> SEQUENCE: 1
atgaagattc ctaacattgg taatgtgatg aataaatttg agatccttgg ggttgtaggt      60
gaaggagcct atggagttgt acttaaatgc agacacaagg aaacacatga aattgtggcg     120
atcaagaaat tcaaggacag tgaagaaaat gaagaagtca aagaaacgac tttacgagag     180
cttaaaatgc ttcggactct caagcaggaa aacattgtgg agttgaagga agcatttcgt     240
cggaggggaa agttgtactt ggtgtttgag tatgttgaaa aaaatatgct cgaattgctg     300
```

```
gaagaaatgc caaatggagt tccacctgag aaagtaaaaa gctacatcta tcagctaatc    360
aaggctattc actggtgcca taagaatgat attgtccatc gagatataaa accagaaaat    420
ctcttaatca gccacaatga tgtcctaaaa ctgtgtgact ttggttttgc tcgtaatctg    480
tcagaaggca ataatgctaa ttacacagag tacgttgcca ccagatggta tcggtcccca    540
gaactcttac ttggcgctcc ctatggaaag tccgtggaca tgtggtcggt gggctgtatt    600
cttggggagc ttagcgatgg acagccttta tttcctggag aaagtgaaat tgaccaactt    660
tttactattc agaaggtgct aggaccactt ccatctgagc agatgaagct tttctacagt    720
aatcctcgct tccatgggct ccggtttcca gctgttaacc atcctcagtc cttggaaaga    780
agataccttg gaattttgaa tagtgttcta cttgacctaa tgaagaattt actgaagttg    840
gacccagctg acagatactt gacagaacag tgtttgaatc accctacatt tcaaacccag    900
agacttctgg atcgttctcc ttcaaggtca gcaaaaagaa aaccttacca tgtggaaagc    960
agcacattgt ctaatagaaa ccaagccggc aaaagtactg ctttgcagtc tcaccacaga   1020
tctaacagca aggacatcca gaacctgagt gtaggcctgc cccgggctga cgaaggtctc   1080
cctgccaatg aaagcttcct aaatggaaac cttgctggag ctagtcttag tccactgcac   1140
accaaaacct accaagcaag cagccagcct gggtctacca gcaaagatct caccaacaac   1200
aacataccac accttcttag cccaaaagaa gccaagtcaa aaacagagtt tgattttaat   1260
attgacccaa agccttcaga aggcccaggg acaaagtacc tcaagtcaaa cagcagatct   1320
cagcagaacc gccactcatt catggaaagc tctcaaagca aagctgggac actgcagccc   1380
aatgaaaagc agagtcggca tagctatatt gacacaattc cccagtcctc taggagtccc   1440
tcctacagga ccaaggccaa aagccatggg gcactgagtg actccaagtc tgtgagcaac   1500
ctttctgaag ccagggccca aattgcggag cccagtacca gtaggtactt cccatctagc   1560
tgcttagact tgaattctcc caccagccca accccaccca gacacagtga cacgagaact   1620
ttgctcagcc cttctggaag aaataaccga aatgagggaa cgctggactc acgtcgaacc   1680
acaaccagac attctaagac gatggaggaa ttgaagctgc cggagcacat ggacagtagc   1740
cattcccatt cactgtctgc acctcacgaa tcttttttctt atggactggg ctacaccagc   1800 ccctttttctt cccagcaacg tcctcatagg cattctatgt atgtgacccg tgacaaagtg   1860
agagccaagg gcttggatgg aagcttgagc atagggcaag ggatggcagc tagagccaac   1920
agcctgcaac tcttgtcacc ccagcctgga gaacagctcc ctccagagat gactgtggca   1980
agatcttcgg tcaaagagac ctccagagaa ggcacctctt ccttccatac acgccagaag   2040
tctgagggtg gagtgtatca tgacccacac tctgatgatg gcacagcccc caaagaaaat   2100
agacacctat acaatgatcc tgtgccaagg agagttggta gcttttacag agtgccatct   2160
ccacgtccag acaattcttt ccatgaaaat aatgtgtcaa ctagagtttc ttctctacca   2220
tcagagagca gttctggaac caaccactca aaaagacaac cagcattcga tccatggaaa   2280
agtcctgaaa atattagtca ttcagagcaa ctcaaggaaa agagaagca aggattttttc   2340 aggtcaatga aaagaaaaa gaagaaatct caaacagtac ccaattccga cagccctgat   2400
cttctgacgt tgcagaaatc cattcattct gctagcactc caagcagcag accaaaggag   2460
tggcgccccg agaagatctc agatctgcag acccaaagcc agccattaaa atcactgcgc   2520
aagttgttac atctctcttc ggcctcaaat caccecggctt cctcagatcc ccgcttccag   2580
cccttaacag ctcaacaaac caaaaattcc ttctcagaaa ttcggattca cccccctgagc   2640
```

-continued

```
caggcctctg gcgggagcag caacatccgg caggaacccg caccgaaggg caggccagcc      2700
ctccagctgc caggtcagat ggatcctggt tggcatgtgt cctctgtgac caggagtgcc      2760
acagagggcc cttcctactc tgaacagctg ggtgccaaaa gtgggccaaa tgggcacccc      2820
tataacagaa caaatcgctc acgaatgcca aatctgaatg atttaaaaga gacagccttg      2880
```

```
<210> SEQ ID NO 2
<211> LENGTH: 3090
<212> TYPE: DNA
<213> ORGANISM: Homo sapiens

<400> SEQUENCE: 2
```

```
atgaagattc ctaacattgg taatgtgatg aataaatttg agatccttgg ggttgtaggt        60
gaaggagcct atggagttgt acttaaatgc agacacaagg aaacacatga aattgtggcg       120
atcaagaaat tcaaggacag tgaagaaaat gaagaagtca agaaacgac tttacgagag        180 cttaaaatgc ttcggactct caagcaggaa aacattgtgg agttgaagga agcatttcgt       240
cggaggggaa agttgtactt ggtgtttgag tatgttgaaa aaaatatgct cgaattgctg       300
gaagaaatgc caaatggagt tccacctgag aaagtaaaaa gctacatcta tcagctaatc       360
aaggctattc actggtgcca taagaatgat attgtccatc gagatataaa accagaaaat       420
ctcttaatca gccacaatga tgtcctaaaa ctgtgtgact ttggttttgc tcgtaatctg       480
tcagaaggca ataatgctaa ttacacagag tacgttgcca ccagatggta tcggtccca        540 gaactcttac ttggcgctcc ctatggaaag tccgtggaca tgtggtcggt gggctgtatt       600 cttgggagc ttagcgatgg acagcctta tttcctggag aaagtgaaat tgaccaactt         660
tttactattc agaaggtgct aggaccactt ccatctgagc agatgaagct tttctacagt       720
aatcctcgct ccatgggct ccggtttcca gctgttaacc atcctcagtc cttggaaaga        780
agataccttg gaattttgaa tagtgttcta cttgacctaa tgaagaattt actgaagttg       840
gacccagctg acagatactt gacagaacag tgtttgaatc accctacatt tcaaacccag       900
agacttctgg atcgttctcc ttcaaggtca gcaaaaagaa aaccttacca tgtggaaagc       960
agcacattgt ctaatagaaa ccaagccggc aaaagtactg ctttgcagtc tcaccacaga      1020
tctaacagca aggacatcca gaacctgagt gtaggcctgc cccgggctga cgaaggtctc      1080
cctgccaatg aaagcttcct aaatggaaac cttgctggag ctagtcttag tccactgcac      1140
accaaaacct accaagcaag cagccagcct gggtctacca gcaaagatct caccaacaac      1200
aacataccac accttcttag cccaaaagaa gccaagtcaa aaacagagtt tgattttaat      1260
attgacccaa agccttcaga aggcccaggg acaaagtacc tcaagtcaaa cagcagatct      1320
cagcagaacc gccactcatt catggaaagc tctcaaagca aagctgggac actgcagccc      1380
aatgaaaagc agagtcggca tagctatatt gacacaattc cccagtcctc taggagtccc      1440
tcctacagga ccaaggccaa aagccatggg gcactgagtg actccaagtc tgtgagcaac      1500
ctttctgaag ccagggccca aattgcggag cccagtacca gtaggtactt ccatctagc       1560 tgcttagact tgaattctcc caccagccca accccacca gacacagtga cacgagaact       1620
ttgctcagcc cttctggaag aaataaccga aatgagggaa cgctggactc acgtcgaacc      1680
acaaccagac attctaagac gatggaggaa ttgaagctgc cggagcacat ggacagtagc      1740
cattcccatt cactgtctgc acctcacgaa tcttttttctt atggactggg ctacaccagc      1800 ccctttttctt cccagcaacg tcctcatagg cattctatgt atgtgacccg tgacaaagtg      1860
agagccaagg gcttggatgg aagcttgagc ataggggcaag ggatggcagc tagagccaac      1920
```

-continued

```
agcctgcaac tcttgtcacc ccagcctgga gaacagctcc ctccagagat gactgtggca    1980
agatcttcgg tcaaagagac ctccagagaa ggcacctctt ccttccatac acgccagaag    2040
tctgagggtg gagtgtatca tgacccacac tctgatgatg gcacagcccc caaagaaaat    2100
agacacctat acaatgatcc tgtgccaagg agagttggta gcttttacag agtgccatct    2160
ccacgtccag acaattcttt ccatgaaaat aatgtgtcaa ctagagtttc ttctctacca    2220
tcagagagca gttctggaac caaccactca aaaagacaac cagcattcga tccatggaaa    2280
agtcctgaaa atattagtca ttcagagcaa ctcaaggaaa aagagaagca aggatttttc    2340
aggtcaatga aaaagaaaaa gaagaaatct caaacagtac ccaattccga cagccctgat    2400
cttctgacgt tgcagaaatc cattcattct gctagcactc caagcagcag accaaaggag    2460
tggcgccccg agaagatctc agatctgcag acccaaagcc agccattaaa atcactgcgc    2520
aagttgttac atctctcttc ggcctcaaat caccccggctt cctcagatcc ccgcttccag    2580
cccttaacag ctcaacaaac caaaaattcc ttctcagaaa ttcggattca ccccctgagc    2640
caggcctctg gcgggagcag caacatccgg caggaacccg caccgaaggg caggccagcc    2700
ctccagctgc cagacggtgg atgtgatggc agaagacaga gacaccattc tggaccccaa    2760
gatagacgct tcatgttaag gacgacagaa caacaaggag aatacttctg ctgtggtgac    2820
ccaaagaagc ctcacactcc gtgcgtccca aaccgagccc ttcatcgtcc aatctccagt    2880
cctgctccct atccagtact ccaggtccga ggcacttcca tgtgcccgac actccaggtc    2940
cgaggcactg atgctttcag ctgcccaacc cagcaatccg ggttctcttt cttcgtgaga    3000
cacgttatga gggaagccct gattcacagg gcccaggtaa accaagctgc gctcctgaca    3060
taccatgaga atgcggcact gacgggcaag                                      3090
```

```
<210> SEQ ID NO 3
<211> LENGTH: 2880
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
```

```
atgaagattc ctaatattgg gaatgtgatg aataagtttg agattctggg ggtggtgggg     60 gaggggggctt atggggtggt gctgaagtgt aggcataagg agacacatga gattgtggct    120
attaagaagt ttaaggattc tgaggagaat gaggaggtga aggagacaac actgagggag    180
ctgaagatgc tgaggacact gaagcaggag aatattgtgg agctgaagga ggcttttagg    240
aggaggggga agctgtatct ggtgtttgag tatgtggaga agaatatgct ggagctgctg    300
gaggagatgc ctaatggggt gcctcctgag aaggtgaagt cttatattta tcagctgatt    360
aaggctattc attggtgtca taagaatgat attgtgcata gggatattaa gcctgagaat    420
ctgctgattt ctcataatga tgtgctgaag ctgtgtgatt ttgggtttgc taggaatctg    480
tctgagggga ataatgctaa ttatacagag tatgtggcta caaggtggta taggtctcct    540
gagctgctgc tgggggctcc ttatgggaag tctgtggata tgtggtctgt ggggtgtatt    600
ctgggggagc tgtctgatgg gcagcctctg tttcctgggg agtctgagat tgatcagctg    660
tttacaattc agaaggtgct ggggcctctg ccttctgagc agatgaagct gttttattct    720
aatcctaggt ttcatgggct gaggtttcct gctgtgaatc atcctcagtc tctggagagg    780
```

```
aggtatctgg ggattctgaa ttctgtgctg ctggatctga tgaagaatct gctgaagctg     840
gatcctgctg ataggtatct gacagagcag tgtctgaatc atcctacatt tcagacacag     900
aggctgctgg ataggtctcc ttctaggtct gctaagagga agccttatca tgtggagtct     960
tctacactgt ctaataggaa tcaggctggg aagtctacag ctctgcagtc tcatcatagg    1020
tctaattcta aggatattca gaatctgtct gtggggctgc ctagggctga tgaggggctg    1080
cctgctaatg agtcttttct gaatgggaat ctggctgggg cttctctgtc tcctctgcat    1140
acaaagacat atcaggcttc ttctcagcct gggtctacat ctaaggatct gacaaataat    1200
aatattcctc atctgctgtc tcctaaggag gctaagtcta agacagagtt tgattttaat    1260
attgatccta agccttctga gggggcctggg acaaagtatc tgaagtctaa ttctaggtct    1320
cagcagaata ggcattcttt tatggagtct tctcagtcta aggctgggac actgcagcct    1380
aatgagaagc agtctaggca ttcttatatt gatacaattc ctcagtcttc taggtctcct    1440
tcttatagga caaaggctaa gtctcatggg gctctgtctg attctaagtc tgtgtctaat    1500
ctgtctgagg ctagggctca gattgctgag ccttctacat ctaggtattt tccttcttct    1560
tgtctggatc tgaattctcc tacatctcct acacctacaa ggcattctga tacaaggaca    1620
ctgctgtctc cttctgggag gaataatagg aatgagggga cactggattc taggaggaca    1680
acaacaaggc attctaagac aatggaggag ctgaagctgc ctgagcatat ggattcttct    1740
cattctcatt ctctgtctgc tcctcatgag tctttttctt atgggctggg gtatacatct    1800 ccttttctt ctcagcagag gcctcatagg cattctatgt atgtgacaag ggataaggtg    1860
agggctaagg ggctggatgg gtctctgtct attgggcagg ggatggctgc tagggctaat    1920
tctctgcagc tgctgtctcc tcagcctggg gagcagctgc ctcctgagat gacagtggct    1980
aggtcttctg tgaaggagac atctagggag gggacatctt cttttcatac aaggcagaag    2040 tctgagggg gggtgtatca tgatcctcat tctgatgatg ggacagctcc taaggagaat    2100
aggcatctgt ataatgatcc tgtgcctagg agggtgtgggt cttttatag ggtgccttct    2160 cctaggcctg ataattcttt tcatgagaat aatgtgtcta caagggtgtc ttctctgcct    2220
tctgagtctt cttctgggac aaatcattct aagaggcagc ctgctttga tccttggaag    2280 tctcctgaga atatttctca ttctgagcag ctgaaggaga aggagaagca ggggtttttt    2340
aggtctatga agaagaagaa gaagaagtct cagacagtgc ctaattctga ttctcctgat    2400
ctgctgacac tgcagaagtc tattcattct gcttctacac cttcttctag gcctaaggag    2460
tggaggcctg agaagatttc tgatctgcag acacagtctc agcctctgaa gtctctgagg    2520
aagctgctgc atctgtcttc tgcttctaat catcctgctt cttctgatcc taggtttcag    2580
cctctgacag ctcagcagac aaagaattct ttttctgaga ttaggattca tcctctgtct    2640
caggcttctg gggggtcttc taatattagg caggagcctg ctcctaaggg gaggcctgct    2700
ctgcagctgc ctgggcagat ggatcctggg tggcatgtgt cttctgtgac aaggtctgct    2760
acagaggggc cttcttattc tgagcagctg ggggctaagt ctgggcctaa tgggcatcct    2820 tataataggga caaataggtc taggatgcct aatctgaatg atctgaagga gacagctctg    2880
```

<210> SEQ ID NO 4
<211> LENGTH: 2880
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

-continued

<400> SEQUENCE: 4

```
atgaagattc caaatattgg gaatgtgatg aataagtttg agattctggg ggtggtgggg      60 gaggggcat atgggtggt gctgaagtgt aggcataagg agacacatga gattgtggca      120
attaagaagt ttaaggattc agaggagaat gaggaggtga aggagacaac actgagggag      180
ctgaagatgc tgaggacact gaagcaggag aatattgtgg agctgaagga ggcatttagg      240
aggaggggga agctgtatct ggtgtttgag tatgtggaga agaatatgct ggagctgctg      300
gaggagatgc caaatggggt gccaccagag aaggtgaagt catatattta tcagctgatt      360
aaggcaattc attggtgtca taagaatgat attgtgcata gggatattaa gccagagaat      420
ctgctgattt cacataatga tgtgctgaag ctgtgtgatt ttgggtttgc aaggaatctg      480
tcagagggga ataatgcaaa ttatacagag tatgtggcaa caaggtggta taggtcacca      540
gagctgctgc tgggggcacc atatgggaag tcagtggata tgtggtcagt ggggtgtatt      600
ctgggggagc tgtcagatgg gcagccactg tttccagggg agtcagagat tgatcagctg      660
tttacaattc agaaggtgct ggggccactg ccatcagagc agatgaagct gttttattca      720
aatccaaggt ttcatgggct gaggtttcca gcagtgaatc atccacagtc actggagagg      780
aggtatctgg ggattctgaa ttcagtgctg ctggatctga tgaagaatct gctgaagctg      840
gatccagcag ataggtatct gacagagcag tgtctgaatc atccaacatt tcagacacag      900
aggctgctgg ataggtcacc atcaaggtca gcaaagagga agccatatca tgtggagtca      960
tcaacactgt caaataggaa tcaggcaggg aagtcaacag cactgcagtc acatcatagg      1020
tcaaattcaa aggatattca gaatctgtca gtggggctgc caagggcaga tgaggggctg      1080
ccagcaaatg agtcatttct gaatgggaat ctggcagggg catcactgtc accactgcat      1140
acaaagacat atcaggcatc atcacagcca gggtcaacat caaaggatct gacaaataat      1200
aatattccac atctgctgtc accaaaggag gcaaagtcaa agacagagtt tgattttaat      1260
attgatccaa agccatcaga ggggccaggg acaaagtatc tgaagtcaaa ttcaaggtca      1320
cagcagaata ggcattcatt tatggagtca tcacagtcaa aggcagggac actgcagcca      1380
aatgagaagc agtcaaggca ttcatatatt gatacaattc cacagtcatc aaggtcacca      1440
tcatatagga caaaggcaaa gtcacatggg gcactgtcag attcaaagtc agtgtcaaat      1500
ctgtcagagg caagggcaca gattgcagag ccatcaacat caaggtattt tccatcatca      1560
tgtctggatc tgaattcacc aacatcacca acaccaacaa ggcattcaga tacaaggaca      1620
ctgctgtcac catcagggag gaataatagg aatgaggggg cactggattc aaggaggaca      1680
acaacaaggc attcaaagac aatggaggag ctgaagctgc cagagcatat ggattcatca      1740
cattcacatt cactgtcagc accacatgag tcattttcat atgggctggg gtatacatca      1800
ccattttcat cacagcagag gccacatagg cattcaatgt atgtgacaag ggataaggtg      1860
agggcaaagg ggctggatgg gtcactgtca attgggcagg ggatggcagc aagggcaaat      1920
tcactgcagc tgctgtcacc acagccaggg gagcagctgc caccagagat gacagtggca      1980
aggtcatcag tgaaggagac atcaaggtag gggacatcat cattcatac aaggcagaag      2040 tcagaggggg gggtgtatca tgatccacat tcagatgatg ggacagcacc aaaggagaat      2100
aggcatctgt ataatgatcc agtgccaagg agggtggggt cattttatag ggtgccatca      2160
ccaaggccag ataattcatt tcatgagaat aatgtgtcaa caaggggtgtc atcactgcca      2220 tcagagtcat catcagggac aaatcattca aagaggcagc cagcatttga tccatggaag      2280
```

-continued

```
tcaccagaga atatttcaca ttcagagcag ctgaaggaga aggagaagca ggggtttttt       2340
aggtcaatga agaagaagaa gaagaagtca cagacagtgc caaattcaga ttcaccagat       2400
ctgctgacac tgcagaagtc aattcattca gcatcaacac catcatcaag gccaaaggag       2460
tggaggccag agaagatttc agatctgcag acacagtcac agccactgaa gtcactgagg       2520
aagctgctgc atctgtcatc agcatcaaat catccagcat catcagatcc aaggtttcag       2580
ccactgacag cacagcagac aaagaattca ttttcagaga ttaggattca tccactgtca       2640
caggcatcag gggggtcatc aaatattagg caggagccag caccaaaggg gaggccagca       2700
ctgcagctgc cagggcagat ggatccaggg tggcatgtgt catcagtgac aaggtcagca       2760
acagaggggc catcatattc agagcagctg ggggcaaagt cagggccaaa tgggcatcca       2820
tataatagga caaataggtc aaggatgcca aatctgaatg atctgaagga gacagcactg       2880
```

<210> SEQ ID NO 5
<211> LENGTH: 2880
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5

```
atgaagatac caaatatagg taatgtaatg aataagtttg aaatactagg tgtagtaggt         60
gaaggtgcat atggtgtagt actaaagtgt aggcataagg aaacacatga aatagtagca        120
ataaagaagt ttaaggattc agaagaaaat gaagaagtaa aggaaacaac actaagggaa        180
ctaaagatgc taaggacact aaagcaagaa aatatagtag aactaaagga agcatttagg        240
aggaggggta agctatatct agtatttgaa tatgtagaaa agaatatgct agaactacta        300
gaagaaatgc caaatggtgt accaccagaa aaggtaaagt catatatata tcaactaata        360
aaggcaatac attggtgtca taagaatgat atagtacata gggatataaa gccagaaaat        420
ctactaatat cacataatga tgtactaaag ctatgtgatt ttggttttgc aaggaatcta        480
tcagaaggta ataatgcaaa ttatacagaa tatgtagcaa caaggtggta taggtcacca        540
gaactactac taggtgcacc atatggtaag tcagtagata tgtggtcagt aggttgtata        600
ctaggtgaac tatcagatgg tcaaccacta tttccaggtg aatcagaaat agatcaacta        660
tttacaatac aaaaggtact aggtccacta ccatcagaac aaatgaagct attttattca        720
aatccaaggt ttcatggtct aaggtttcca gcagtaaatc atccacaatc actagaaagg        780
aggtatctag gtatactaaa ttcagtacta ctagatctaa tgaagaatct actaaagcta        840
gatccagcag ataggtatct aacagaacaa tgtctaaatc atccaacatt tcaaacacaa        900
aggctactag ataggtcacc atcaaggtca gcaaagagga agccatatca tgtagaatca        960
tcaacactat caaataggaa tcaagcaggt aagtcaacag cactacaatc acatcatagg       1020
tcaaattcaa aggatataca aaatctatca gtaggtctac caagggcaga tgaaggtcta       1080
ccagcaaatg aatcatttct aaatggtaat ctagcaggtg catcactatc accactacat       1140
acaaagacat atcaagcatc atcacaacca ggttcaacat caaggatct aacaaataat       1200 aatataccac atctactatc accaaaggaa gcaaagtcaa agacagaatt tgattttaat       1260
atagatccaa agccatcaga aggtccaggt acaaagtatc taaagtcaaa ttcaaggtca       1320
caacaaaata ggcattcatt tatggaatca tcacaatcaa aggcaggtac actacaacca       1380
aatgaaaagc aatcaaggca ttcatatata gatacaatac cacaatcatc aaggtcacca       1440
```

```
tcatatagga caaaggcaaa gtcacatggt gcactatcag attcaaagtc agtatcaaat     1500
ctatcagaag caagggcaca aatagcagaa ccatcaacat caaggtattt tccatcatca     1560
tgtctagatc taaattcacc aacatcacca acaccaacaa ggcattcaga tacaaggaca     1620
ctactatcac catcaggtag gaataatagg aatgaaggta cactagattc aaggaggaca     1680
acaacaaggc attcaaagac aatggaagaa ctaaagctac cagaacatat ggattcatca     1740
cattcacatt cactatcagc accacatgaa tcattttcat atggtctagg ttatacatca     1800
ccattttcat cacaacaaag gccacatagg cattcaatgt atgtaacaag ggataaggta     1860
agggcaaagg gtctagatgg ttcactatca ataggtcaag gtatggcagc aagggcaaat     1920
tcactacaac tactatcacc acaaccaggt gaacaactac caccagaaat gacagtagca     1980
aggtcatcag taaaggaaac atcaagggaa ggtacatcat catttcatac aaggcaaaag     2040
tcagaaggtg gtgtatatca tgatccacat tcagatgatg gtacagcacc aaaggaaaat     2100
aggcatctat ataatgatcc agtaccaagg agggtaggtt cattttatag ggtaccatca     2160
ccaaggccag ataattcatt tcatgaaaat aatgtatcaa caagggtatc atcactacca     2220
tcagaatcat catcaggtac aaatcattca aagaggcaac cagcatttga tccatggaag     2280
tcaccagaaa atatatcaca ttcagaacaa ctaaaggaaa aggaaaagca aggttttttt     2340
aggtcaatga agaagaagaa gaagaagtca caaacagtac caaattcaga ttcaccagat     2400
ctactaacac tacaaaagtc aatacattca gcatcaacac catcatcaag gccaaaggaa     2460
tggaggccag aaaagatatc agatctacaa acacaatcac aaccactaaa gtcactaagg     2520
aagctactac atctatcatc agcatcaaat catccagcat catcagatcc aaggtttcaa     2580
ccactaacag cacaacaaac aaagaattca ttttcagaaa taaggataca tccactatca     2640
caagcatcag gtggttcatc aaatataagg caagaaccag caccaaaggg taggccagca     2700
ctacaactac caggtcaaat ggatccaggt tggcatgtat catcagtaac aaggtcagca     2760
acagaaggtc catcatattc agaacaacta ggtgcaaagt caggtccaaa tggtcatcca     2820
tataatagga caaataggtc aaggatgcca aatctaaatg atctaaagga aacagcacta     2880
```

<210> SEQ ID NO 6
<211> LENGTH: 3090
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

```
atgaagattc ctaatattgg gaatgtgatg aataagtttg agattctggg ggtggtgggg      60
gagggggctt atggggtggt gctgaagtgt aggcataagg agacacatga gattgtggct     120
attaagaagt ttaaggattc tgaggagaat gaggaggtga aggagacaac actgagggag     180
ctgaagatgc tgaggacact gaagcaggag aatattgtgg agctgaagga ggcttttagg     240
aggaggggga agctgtatct ggtgtttgag tatgtggaga agaatatgct ggagctgctg     300
gaggagatgc ctaatggggt gcctcctgag aaggtgaagt cttatatta tcagctgatt      360 aaggctattc attggtgtca taagaatgat attgtgcata gggatattaa gcctgagaat     420
ctgctgattt ctcataatga tgtgctgaag ctgtgtgatt ttgggtttgc taggaatctg     480
tctgagggga ataatgctaa ttatacagag tatgtggcta caaggtggta taggtctcct     540
```

-continued

```
gagctgctgc tgggggctcc ttatgggaag tctgtggata tgtggtctgt ggggtgtatt      600 ctggggagc  tgtctgatgg gcagcctctg tttcctgggg agtctgagat tgatcagctg      660
tttacaattc agaaggtgct ggggcctctg ccttctgagc agatgaagct gttttattct      720
aatcctaggt ttcatgggct gaggtttcct gctgtgaatc atcctcagtc tctggagagg      780
aggtatctgg ggattctgaa ttctgtgctg ctggatctga tgaagaatct gctgaagctg      840
gatcctgctg ataggtatct gacagagcag tgtctgaatc atcctacatt tcagacacag      900
aggctgctgg ataggtctcc ttctaggtct gctaagagga agccttatca tgtggagtct      960
tctacactgt ctaataggaa tcaggctggg aagtctacag ctctgcagtc tcatcatagg     1020
tctaattcta aggatattca gaatctgtct gtggggctgc ctagggctga tgaggggctg     1080
cctgctaatg agtcttttct gaatgggaat ctggctgggg cttctctgtc tcctctgcat     1140
acaaagacat atcaggcttc ttctcagcct gggtctacat ctaaggatct gacaaataat     1200
aatattcctc atctgctgtc tcctaaggag gctaagtcta agacagagtt tgatttttaat     1260 attgatccta agccttctga ggggcctggg acaaagtatc tgaagtctaa ttctaggtct     1320
cagcagaata ggcattcttt tatggagtct tctcagtcta aggctgggac actgcagcct     1380
aatgagaagc agtctaggca ttcttatatt gatacaattc ctcagtcttc taggtctcct     1440
tcttatagga caaaggctaa gtctcatggg gctctgtctg attctaagtc tgtgtctaat     1500
ctgtctgagg ctagggctca gattgctgag ccttctacat ctaggtattt tccttcttct     1560
tgtctggatc tgaattctcc tacatctcct acacctacaa ggcattctga tacaaggaca     1620
ctgctgtctc cttctgggag gaataatagg aatgagggga cactggattc taggaggaca     1680
acaacaaggc attctaagac aatggaggag ctgaagctgc ctgagcatat ggattcttct     1740
cattctcatt ctctgtctgc tcctcatgag tcttttttctt atgggctggg gtatacatct     1800 ccttttttctt ctcagcagag gcctcatagg cattctatgt atgtgacaag ggataaggtg     1860
agggctaagg ggctggatgg gtctctgtct attgggcagg ggatggctgc tagggctaat     1920
tctctgcagc tgctgtctcc tcagcctggg gagcagctgc ctcctgagat gacagtggct     1980
aggtcttctg tgaaggagac atctagggag gggacatctt ctttttcatac aaggcagaag     2040 tctgaggggg gggtgtatca tgatcctcat tctgatgatg ggacagctcc taaggagaat     2100
aggcatctgt ataatgatcc tgtgcctagg agggtggggt cttttttatag ggtgccttct     2160 cctaggcctg ataattcttt tcatgagaat aatgtgtcta caagggtgtc ttctctgcct     2220
tctgagtctt cttctgggac aaatcattct aagaggcagc ctgctttttga tccttggaag     2280 tctcctgaga atatttctca ttctgagcag ctgaaggaga aggagaagca ggggtttttt     2340
aggtctatga agaagaagaa gaagaagtct cagacagtgc ctaattctga ttctcctgat     2400
ctgctgacac tgcagaagtc tattcattct gcttctacac cttcttctag gcctaaggag     2460
tggaggcctg agaagatttc tgatctgcag acacagtctc agcctctgaa gtctctgagg     2520
aagctgctgc atctgtcttc tgcttctaat catcctgctt cttctgatcc taggtttcag     2580
cctctgacag ctcagcagac aaagaattct ttttctgaga ttaggattca tcctctgtct     2640
caggcttctg gggggtcttc taatattagg caggagcctg ctcctaaggg gaggcctgct     2700
ctgcagctgc ctgatggggg gtgtgatggg aggaggcaga ggcatcattc tgggcctcag     2760
gataggaggt ttatgctgag gacaacagag cagcaggggg agtattttttg ttgtggggat     2820 cctaagaagc ctcatacacc ttgtgtgcct aataggggctc tgcataggcc tatttcttct     2880
cctgctcctt atcctgtgct gcaggtgagg gggacatcta tgtgtcctac actgcaggtg     2940
```

```
aggggggacag atgctttttc ttgtcctaca cagcagtctg ggtttttcttt ttttgtgagg    3000 catgtgatga gggaggctct gattcatagg gctcaggtga atcaggctgc tctgctgaca    3060
tatcatgaga atgctgctct gacagggaag                                     3090

<210> SEQ ID NO 7
<211> LENGTH: 3090
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
atgaagattc caaatattgg gaatgtgatg aataagtttg agattctggg ggtggtgggg      60
gagggggcat atggggtggt gctgaagtgt aggcataagg agacacatga gattgtggca     120
attaagaagt ttaaggattc agaggagaat gaggaggtga aggagacaac actgagggag     180
ctgaagatgc tgaggacact gaagcaggag aatattgtgg agctgaagga ggcatttagg     240
aggaggggga agctgtatct ggtgtttgag tatgtggaga agaatatgct ggagctgctg     300
gaggagatgc caaatggggt gccaccagag aaggtgaagt catatattta tcagctgatt     360
aaggcaattc attggtgtca taagaatgat attgtgcata gggatattaa gccagagaat     420
ctgctgattt cacataatga tgtgctgaag ctgtgtgatt ttgggtttgc aaggaatctg     480
tcagagggga ataatgcaaa ttatacagag tatgtggcaa caaggtggta taggtcacca     540
gagctgctgc tgggggcacc atatgggaag tcagtggata tgtggtcagt ggggtgtatt     600
ctgggggagc tgtcagatgg gcagccactg tttccagggg agtcagagat tgatcagctg     660
tttacaattc agaaggtgct ggggccactg ccatcagagc agatgaagct gttttattca     720
aatccaaggt ttcatgggct gaggtttcca gcagtgaatc atccacagtc actggagagg     780
aggtatctgg ggattctgaa ttcagtgctg ctggatctga tgaagaatct gctgaagctg     840
gatccagcag ataggtatct gacagagcag tgtctgaatc atccaacatt tcagacacag     900
aggctgctgg ataggtcacc atcaaggtca gcaaagagga agccatatca tgtggagtca     960
tcaacactgt caaataggaa tcaggcaggg aagtcaacag cactgcagtc acatcatagg    1020
tcaaattcaa aggatattca gaatctgtca gtggggctgc aagggcagga tgaggggctg    1080
ccagcaaatg agtcatttct gaatgggaat ctggcagggg catcactgtc accactgcat    1140
acaaagacat atcaggcatc atcacagcca gggtcaacat caaaggatct gacaaataat    1200
aatattccac atctgctgtc accaaaggag gcaaagtcaa agacagagtt tgattttaat    1260
attgatccaa agccatcaga ggggccaggg acaaagtatc tgaagtcaaa ttcaaggtca    1320
cagcagaata ggcattcatt tatggagtca tcacagtcaa aggcagggac actgcagcca    1380
aatgagaagc agtcaaggca ttcatatatt gatacaattc cacagtcatc aaggtcacca    1440
tcatatagga caaaggcaaa gtcacatggg gcactgtcag attcaaagtc agtgtcaaat    1500
ctgtcagagg caagggcaca gattgcagag ccatcaacat caaggtattt tccatcatca    1560
tgtctggatc tgaattcacc aacatcacca acaccaacaa ggcattcaga tacaaggaca    1620
ctgctgtcac catcagggag gaataatagg aatgagggga cactggattc aaggaggaca    1680
acaacaaggc attcaaagac aatggaggag ctgaagctgc cagagcatat ggattcatca    1740
cattcacatt cactgtcagc accacatgag tcattttcat atgggctggg gtatacatca    1800
```

-continued

```
ccattttcat cacagcagag gccacatagg cattcaatgt atgtgacaag ggataaggtg      1860
agggcaaagg ggctggatgg gtcactgtca attgggcagg ggatggcagc aagggcaaat      1920
tcactgcagc tgctgtcacc acagccaggg gagcagctgc caccagagat gacagtggca      1980
aggtcatcag tgaaggagac atcaagggag gggacatcat catttcatac aaggcagaag      2040
tcagaggggg gggtgtatca tgatccacat tcagatgatg ggacagcacc aaaggagaat      2100
aggcatctgt ataatgatcc agtgccaagg agggtggggt catttatag ggtgccatca       2160 ccaaggccag ataattcatt tcatgagaat aatgtgtcaa caagggtgtc atcactgcca      2220
tcagagtcat catcagggac aaatcattca aagaggcagc cagcatttga tccatggaag      2280
tcaccagaga atatttcaca ttcagagcag ctgaaggaga aggagaagca ggggtttttt      2340
aggtcaatga agaagaagaa gaagaagtca cagacagtgc caaattcaga ttcaccagat      2400
ctgctgacac tgcagaagtc aattcattca gcatcaacac catcatcaag gccaaaggag      2460
tggaggccag agaagatttc agatctgcag acacagtcac agccactgaa gtcactgagg      2520
aagctgctgc atctgtcatc agcatcaaat catccagcat catcagatcc aaggtttcag      2580
ccactgacag cacagcagac aaagaattca ttttcagaga ttaggattca tccactgtca      2640
caggcatcag gggggtcatc aaatattagg caggagccag caccaaaggg gaggccagca      2700
ctgcagctgc cagatggggg gtgtgatggg aggaggcaga ggcatcattc agggccacag      2760
gataggaggt ttatgctgag gacaacagag cagcaggggg agtattttg ttgtggggat       2820 ccaaagaagc cacatacacc atgtgtgcca aatagggcac tgcataggcc aatttcatca      2880
ccagcaccat atccagtgct gcaggtgagg gggacatcaa tgtgtccaac actgcaggtg      2940 aggggggacag atgcattttc atgtccaaca cagcagtcag ggttttcatt ttttgtgagg     3000
catgtgatga gggaggcact gattcatagg gcacaggtga atcaggcagc actgctgaca     3060
tatcatgaga atgcagcact gacagggaag                                       3090
```

<210> SEQ ID NO 8
<211> LENGTH: 3090
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8

```
atgaagatac caaatatagg taatgtaatg aataagtttg aaatactagg tgtagtaggt       60
gaaggtgcat atggtgtagt actaaagtgt aggcataagg aaacacatga aatagtagca      120
ataaagaagt ttaaggattc agaagaaaat gaagaagtaa aggaaacaac actaagggaa      180
ctaaagatgc taaggacact aaagcaagaa aatatagtag aactaaagga agcatttagg      240
aggaggggta agctatatct agtatttgaa tatgtagaaa agaatatgct agaactacta      300
gaagaaatgc caaatggtgt accaccagaa aaggtaaagt catatatata tcaactaata      360
aaggcaatac attggtgtca taagaatgat atagtacata gggatataaa gccagaaaat      420
ctactaatat cacataatga tgtactaaag ctatgtgatt ttggttttgc aaggaatcta      480
tcagaaggta ataatgcaaa ttatacagaa tatgtagcaa caaggtggta taggtcacca      540
gaactactac taggtgcacc atatggtaag tcagtagata tgtggtcagt aggttgtata      600
ctaggtgaac tatcagatgg tcaaccacta tttccaggtg aatcagaaat agatcaacta      660
tttacaatac aaaaggtact aggtccacta ccatcagaac aaatgaagct attttattca      720
```

```
aatccaaggt ttcatggtct aaggtttcca gcagtaaatc atccacaatc actagaaagg     780
aggtatctag gtatactaaa ttcagtacta ctagatctaa tgaagaatct actaaagcta     840
gatccagcag ataggtatct aacagaacaa tgtctaaatc atccaacatt tcaaacacaa     900
aggctactag ataggtcacc atcaaggtca gcaaagagga agccatatca tgtagaatca     960
tcaacactat caaataggaa tcaagcaggt aagtcaacag cactacaatc acatcatagg    1020
tcaaattcaa aggatataca aaatctatca gtaggtctac caagggcaga tgaaggtcta    1080
ccagcaaatg aatcatttct aaatggtaat ctagcaggtg catcactatc accactacat    1140
acaaagacat atcaagcatc atcacaacca ggttcaacat caaggatct aacaaataat    1200 aatataccac atctactatc accaaaggaa gcaaagtcaa agacagaatt tgattttaat    1260
atagatccaa agccatcaga aggtccaggt acaaagtatc taaagtcaaa ttcaaggtca    1320
caacaaaata ggcattcatt tatggaatca tcacaatcaa aggcaggtac actacaacca    1380
aatgaaaagc aatcaaggca ttcatatata gatacaatac cacaatcatc aaggtcacca    1440
tcatatagga caaaggcaaa gtcacatggt gcactatcag attcaaagtc agtatcaaat    1500
ctatcagaag caagggcaca aatagcagaa ccatcaacat caaggtattt tccatcatca    1560
tgtctagatc taaattcacc aacatcacca acaccaacaa ggcattcaga tacaaggaca    1620
ctactatcac catcaggtag gaataatagg aatgaaggta cactagattc aaggaggaca    1680
acaacaaggc attcaaagac aatggaagaa ctaaagctac cagaacatat ggattcatca    1740
cattcacatt cactatcagc accacatgaa tcattttcat atggtctagg ttatacatca    1800
ccattttcat cacaacaaag gccacatagg cattcaatgt atgtaacaag ggataaggta    1860
agggcaaagg gtctagatgg ttcactatca ataggtcaag gtatggcagc aagggcaaat    1920
tcactacaac tactatcacc acaaccaggt gaacaactac caccagaaat gacagtagca    1980
aggtcatcag taaaggaaac atcaagggaa ggtacatcat catttcatac aaggcaaaag    2040
tcagaaggtg gtgtatatca tgatccacat tcagatgatg gtacagcacc aaaggaaaat    2100
aggcatctat ataatgatcc agtaccaagg agggtaggtt cattttatag ggtaccatca    2160
ccaaggccag ataattcatt tcatgaaaat aatgtatcaa caagggtatc atcactacca    2220
tcagaatcat catcaggtac aaatcattca aagaggcaac cagcatttga tccatggaag    2280
tcaccagaaa atatatcaca ttcagaacaa ctaaaggaaa aggaaaagca aggtttttt    2340 aggtcaatga agaagaagaa gaagaagtca caaacagtac caaattcaga ttcaccagat    2400
ctactaacac tacaaaagtc aatacattca gcatcaacac catcatcaag gccaaaggaa    2460
tggaggccag aaaagatatc agatctacaa acacaatcac aaccactaaa gtcactaagg    2520
aagctactac atctatcatc agcatcaaat catccagcat catcagatcc aaggtttcaa    2580
ccactaacag cacaacaaac aaagaattca ttttcagaaa taaggataca tccactatca    2640
caagcatcag gtggttcatc aaatataagg caagaaccag caccaaaggg taggccagca    2700
ctacaactac cagatggtgg ttgtgatggt aggaggcaaa ggcatcattc aggtccacaa    2760
gataggaggt ttatgctaag gacaacagaa caacaaggtg aatattttg ttgtggtgat    2820 ccaaagaagc cacatacacc atgtgtacca aatagggcac tacataggcc aatatcatca    2880
ccagcaccat atccagtact acaagtaagg ggtacatcaa tgtgtccaac actacaagta    2940
aggggtacag atgcattttc atgtccaaca caacaatcag gttttttcatt ttttgtaagg    3000 catgtaatga gggaagcact aatacatagg gcacaagtaa atcaagcagc actactaaca    3060
```

-continued

```
tatcatgaaa atgcagcact aacaggtaag                                    3090
```

<210> SEQ ID NO 9
<211> LENGTH: 960
<212> TYPE: PRT
<213> ORGANISM: Homo sapiens

<400> SEQUENCE: 9

```
Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
                20                  25                  30

Lys Glu Thr His Glu Ile Val Ala Ile Lys Lys Phe Lys Asp Ser Glu
            35                  40                  45

Glu Asn Glu Glu Val Lys Glu Thr Thr Leu Arg Glu Leu Lys Met Leu
        50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
            115                 120                 125

Asn Asp Ile Val His Arg Asp Ile Lys Pro Glu Asn Leu Leu Ile Ser
        130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
                180                 185                 190

Asp Met Trp Ser Val Gly Cys Ile Leu Gly Glu Leu Ser Asp Gly Gln
            195                 200                 205

Pro Leu Phe Pro Gly Glu Ser Glu Ile Asp Gln Leu Phe Thr Ile Gln
        210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
            275                 280                 285

Glu Gln Cys Leu Asn His Pro Thr Phe Gln Thr Gln Arg Leu Leu Asp
        290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
            355                 360                 365
```

-continued

```
Gly Asn Leu Ala Gly Ala Ser Leu Ser Pro Leu His Thr Lys Thr Tyr
    370             375             380

Gln Ala Ser Ser Gln Pro Gly Ser Thr Ser Lys Asp Leu Thr Asn Asn
385             390             395             400

Asn Ile Pro His Leu Leu Ser Pro Lys Glu Ala Lys Ser Lys Thr Glu
            405             410             415

Phe Asp Phe Asn Ile Asp Pro Lys Pro Ser Glu Gly Pro Gly Thr Lys
            420             425             430

Tyr Leu Lys Ser Asn Ser Arg Ser Gln Gln Asn Arg His Ser Phe Met
        435             440             445

Glu Ser Ser Gln Ser Lys Ala Gly Thr Leu Gln Pro Asn Glu Lys Gln
    450             455             460

Ser Arg His Ser Tyr Ile Asp Thr Ile Pro Gln Ser Ser Arg Ser Pro
465             470             475             480

Ser Tyr Arg Thr Lys Ala Lys Ser His Gly Ala Leu Ser Asp Ser Lys
            485             490             495

Ser Val Ser Asn Leu Ser Glu Ala Arg Ala Gln Ile Ala Glu Pro Ser
        500             505             510

Thr Ser Arg Tyr Phe Pro Ser Ser Cys Leu Asp Leu Asn Ser Pro Thr
        515             520             525

Ser Pro Thr Pro Thr Arg His Ser Asp Thr Arg Thr Leu Leu Ser Pro
    530             535             540

Ser Gly Arg Asn Asn Arg Asn Glu Gly Thr Leu Asp Ser Arg Arg Thr
545             550             555             560

Thr Thr Arg His Ser Lys Thr Met Glu Glu Leu Lys Leu Pro Glu His
            565             570             575

Met Asp Ser Ser His Ser His Ser Leu Ser Ala Pro His Glu Ser Phe
        580             585             590

Ser Tyr Gly Leu Gly Tyr Thr Ser Pro Phe Ser Ser Gln Gln Arg Pro
        595             600             605

His Arg His Ser Met Tyr Val Thr Arg Asp Lys Val Arg Ala Lys Gly
    610             615             620

Leu Asp Gly Ser Leu Ser Ile Gly Gln Gly Met Ala Ala Arg Ala Asn
625             630             635             640

Ser Leu Gln Leu Leu Ser Pro Gln Pro Gly Glu Gln Leu Pro Pro Glu
            645             650             655

Met Thr Val Ala Arg Ser Ser Val Lys Glu Thr Ser Arg Glu Gly Thr
            660             665             670

Ser Ser Phe His Thr Arg Gln Lys Ser Glu Gly Gly Val Tyr His Asp
        675             680             685

Pro His Ser Asp Asp Gly Thr Ala Pro Lys Glu Asn Arg His Leu Tyr
    690             695             700

Asn Asp Pro Val Pro Arg Arg Val Gly Ser Phe Tyr Arg Val Pro Ser
705             710             715             720

Pro Arg Pro Asp Asn Ser Phe His Glu Asn Asn Val Ser Thr Arg Val
            725             730             735

Ser Ser Leu Pro Ser Glu Ser Ser Ser Gly Thr Asn His Ser Lys Arg
            740             745             750

Gln Pro Ala Phe Asp Pro Trp Lys Ser Pro Glu Asn Ile Ser His Ser
        755             760             765

Glu Gln Leu Lys Glu Lys Glu Lys Gln Gly Phe Phe Arg Ser Met Lys
    770             775             780

Lys Lys Lys Lys Lys Ser Gln Thr Val Pro Asn Ser Asp Ser Pro Asp
```

-continued

```
785              790              795              800

Leu Leu Thr Leu Gln Lys Ser Ile His Ser Ala Ser Thr Pro Ser Ser
                805              810              815

Arg Pro Lys Glu Trp Arg Pro Glu Lys Ile Ser Asp Leu Gln Thr Gln
            820              825              830

Ser Gln Pro Leu Lys Ser Leu Arg Lys Leu Leu His Leu Ser Ser Ala
            835              840              845

Ser Asn His Pro Ala Ser Ser Asp Pro Arg Phe Gln Pro Leu Thr Ala
        850              855              860

Gln Gln Thr Lys Asn Ser Phe Ser Glu Ile Arg Ile His Pro Leu Ser
865              870              875              880

Gln Ala Ser Gly Gly Ser Ser Asn Ile Arg Gln Glu Pro Ala Pro Lys
            885              890              895

Gly Arg Pro Ala Leu Gln Leu Pro Gly Gln Met Asp Pro Gly Trp His
            900              905              910

Val Ser Ser Val Thr Arg Ser Ala Thr Glu Gly Pro Ser Tyr Ser Glu
            915              920              925

Gln Leu Gly Ala Lys Ser Gly Pro Asn Gly His Pro Tyr Asn Arg Thr
        930              935              940

Asn Arg Ser Arg Met Pro Asn Leu Asn Asp Leu Lys Glu Thr Ala Leu
945              950              955              960

<210> SEQ ID NO 10
<211> LENGTH: 1030
<212> TYPE: PRT
<213> ORGANISM: Homo sapiens

<400> SEQUENCE: 10

Met Lys Ile Pro Asn Ile Gly Asn Val Met Asn Lys Phe Glu Ile Leu
1               5               10              15

Gly Val Val Gly Glu Gly Ala Tyr Gly Val Val Leu Lys Cys Arg His
            20              25              30

Lys Glu Thr His Glu Ile Val Ala Ile Lys Lys Phe Lys Asp Ser Glu
        35              40              45

Glu Asn Glu Glu Val Lys Glu Thr Thr Leu Arg Glu Leu Lys Met Leu
    50              55              60

Arg Thr Leu Lys Gln Glu Asn Ile Val Glu Leu Lys Glu Ala Phe Arg
65              70              75              80

Arg Arg Gly Lys Leu Tyr Leu Val Phe Glu Tyr Val Glu Lys Asn Met
            85              90              95

Leu Glu Leu Leu Glu Glu Met Pro Asn Gly Val Pro Pro Glu Lys Val
            100             105             110

Lys Ser Tyr Ile Tyr Gln Leu Ile Lys Ala Ile His Trp Cys His Lys
        115             120             125

Asn Asp Ile Val His Arg Asp Ile Lys Pro Glu Asn Leu Leu Ile Ser
        130             135             140

His Asn Asp Val Leu Lys Leu Cys Asp Phe Gly Phe Ala Arg Asn Leu
145             150             155             160

Ser Glu Gly Asn Asn Ala Asn Tyr Thr Glu Tyr Val Ala Thr Arg Trp
            165             170             175

Tyr Arg Ser Pro Glu Leu Leu Leu Gly Ala Pro Tyr Gly Lys Ser Val
            180             185             190

Asp Met Trp Ser Val Gly Cys Ile Leu Gly Glu Leu Ser Asp Gly Gln
            195             200             205
```

-continued

```
Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
            245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
            325                 330                 335

Ser His His Arg Ser Asn Ser Lys Asp Ile Gln Asn Leu Ser Val Gly
        340                 345                 350

Leu Pro Arg Ala Asp Glu Gly Leu Pro Ala Asn Glu Ser Phe Leu Asn
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
            405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
            485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
            565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
```

-continued

```
625             630             635             640

Ser Leu Gln Leu Leu Ser Pro Gln Pro Gly Glu Gln Leu Pro Pro Glu
             645             650             655

Met Thr Val Ala Arg Ser Ser Val Lys Glu Thr Ser Arg Glu Gly Thr
             660             665             670

Ser Ser Phe His Thr Arg Gln Lys Ser Glu Gly Gly Val Tyr His Asp
             675             680             685

Pro His Ser Asp Asp Gly Thr Ala Pro Lys Glu Asn Arg His Leu Tyr
     690             695             700

Asn Asp Pro Val Pro Arg Arg Val Gly Ser Phe Tyr Arg Val Pro Ser
705             710             715             720

Pro Arg Pro Asp Asn Ser Phe His Glu Asn Asn Val Ser Thr Arg Val
             725             730             735

Ser Ser Leu Pro Ser Glu Ser Ser Ser Gly Thr Asn His Ser Lys Arg
             740             745             750

Gln Pro Ala Phe Asp Pro Trp Lys Ser Pro Glu Asn Ile Ser His Ser
             755             760             765

Glu Gln Leu Lys Glu Lys Glu Lys Gln Gly Phe Phe Arg Ser Met Lys
     770             775             780

Lys Lys Lys Lys Lys Ser Gln Thr Val Pro Asn Ser Asp Ser Pro Asp
785             790             795             800

Leu Leu Thr Leu Gln Lys Ser Ile His Ser Ala Ser Thr Pro Ser Ser
             805             810             815

Arg Pro Lys Glu Trp Arg Pro Glu Lys Ile Ser Asp Leu Gln Thr Gln
             820             825             830

Ser Gln Pro Leu Lys Ser Leu Arg Lys Leu Leu His Leu Ser Ser Ala
             835             840             845

Ser Asn His Pro Ala Ser Ser Asp Pro Arg Phe Gln Pro Leu Thr Ala
     850             855             860

Gln Gln Thr Lys Asn Ser Phe Ser Glu Ile Arg Ile His Pro Leu Ser
865             870             875             880

Gln Ala Ser Gly Gly Ser Ser Asn Ile Arg Gln Glu Pro Ala Pro Lys
             885             890             895

Gly Arg Pro Ala Leu Gln Leu Pro Asp Gly Gly Cys Asp Gly Arg Arg
             900             905             910

Gln Arg His His Ser Gly Pro Gln Asp Arg Arg Phe Met Leu Arg Thr
             915             920             925

Thr Glu Gln Gln Gly Glu Tyr Phe Cys Cys Gly Asp Pro Lys Lys Pro
     930             935             940

His Thr Pro Cys Val Pro Asn Arg Ala Leu His Arg Pro Ile Ser Ser
945             950             955             960

Pro Ala Pro Tyr Pro Val Leu Gln Val Arg Gly Thr Ser Met Cys Pro
             965             970             975

Thr Leu Gln Val Arg Gly Thr Asp Ala Phe Ser Cys Pro Thr Gln Gln
             980             985             990

Ser Gly Phe Ser Phe Phe Val Arg  His Val Met Arg Glu  Ala Leu Ile
             995             1000             1005

His Arg  Ala Gln Val Asn Gln  Ala Ala Leu Leu Thr  Tyr His Glu
     1010             1015             1020

Asn Ala  Ala Leu Thr Gly Lys
1025             1030
```

<210> SEQ ID NO 11

-continued

```
<211> LENGTH: 145
<212> TYPE: DNA
<213> ORGANISM: Adeno-associated virus 2

<400> SEQUENCE: 11
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                          145

<210> SEQ ID NO 12
<211> LENGTH: 448
<212> TYPE: DNA
<213> ORGANISM: Homo sapiens

<400> SEQUENCE: 12
agtgcaagtg ggtttttagga ccaggatgag gcggggtggg ggtgcctacc tgacgaccga     60
ccccgaccca ctggacaagc acccaacccc cattccccaa attgcgcatc ccctatcaga    120 gaggggggagg ggaaacagga tgcggcgagg cgcgtgcgca ctgccagctt cagcaccgcg    180
gacagtgcct tcgcccccgc ctggcggcgc gcgccaccgc cgcctcagca ctgaaggcgc    240
gctgacgtca ctcgccggtc ccccgcaaac tccccttccc ggccaccttg gtcgcgtccg    300
cgccgccgcc ggcccagccg gaccgcacca cgcgaggcgc gagataggggg ggcacgggcg    360 cgaccatctg cgctgcggcg ccggcgactc agcgctgcct cagtctgcgg tgggcagcgg    420
aggagtcgtg tcgtgcctga gagcgcag                                      448

<210> SEQ ID NO 13
<211> LENGTH: 276
<212> TYPE: DNA
<213> ORGANISM: Gallus sp.

<400> SEQUENCE: 13
tcgaggtgag ccccacgttc tgcttcactc tccccatctc cccccctcc ccaccccaa       60 ttttgtattt atttattttt taattatttt atgcagcgat gggggcgggg gggggggggg    120
cgcgcgccag gcggggcggg gcggggcgag gggcggggcg gggcgaggcg gagaggtgcg    180
gcggcagcca atcagagcgg cgcgctccga aagtttcctt ttatggcgag gcggcggcgg    240
cggcggccct ataaaaagcg aagcgcgcgg cgggcg                             276

<210> SEQ ID NO 14
<211> LENGTH: 1654
<212> TYPE: DNA
<213> ORGANISM: Homo sapiens

<400> SEQUENCE: 14
tgcgaagccc tctgttgttg cctctgactc cattttccct ctttgctaat tcattgctcc     60
tacctgtaaa attttctaat atgcttccac tttcatttcc tcatcaaata ttcaccgtta    120
tgaaaaagaa aatcctattg gcttggtatc aagtggccaa actgagcatg ctgctacata    180
ttgttaccag attcactaca ggaatagatt aagtggattt tatcccaaat atctatttcc    240
tattacagta ctgcatcttt ctaatttggt ggcagctatg acctcataca ctgcctattt    300
tccgtgcttt tcctaaccag aagagaccct attttttctcc tttgcttgtt aaagcgaaaa    360
taattatgca gctttccata gatttgtccc caatgtcttt ttaaaaaaat ttttttttctt   420 tattttctaa aagtagcatt ggaaatgtta tctccttcaa tttcatcacc tcttcatcct    480
ccttggaaac ccgatccatg gtgggtatta agatctttac atttgtactg gttgggcgat    540
```

```
gacttcattg ctttcaagcc agctggggga tcttgtgtgg cagagcatcg gaccgaagcg      600
gaggtgtggg tcgttgctgc tgctgctgct gctactgctg caacagctct ttgcacgcgc      660
ccagctgctg tgtaaggaat cctcaggctg ctaggtcttt gcgcctaact cacccaaggg      720
accgcaagct gctggatgag tgtacgtgtg agtgtgtgtt gtgtgtgtgc atatgtgcgt      780
gtgtgtgtgc acacgcagcg gcaacagttg ggcagcagca gcaatggact tcgatatcat      840
ttttaccaac aacagagata aaccatcctc catcctgtat ttctcagctc ccgccccgag      900
tatgttctcc ccctcttctc cgacttcccc caccccagcc cccggcacgg gtccctccgg      960
agggagggca gggtagctgc gctgcaggca ggattccctc ttttttccgc agtgacaggc     1020
ggattccggg gcctcctcgc cacctcctac ccccgcagcc accccctttct cagtcacgat     1080 ctccccaccc caccaccgtc gaccctctcc ctgcttcccc gctctacccc ccggcgtcga     1140
ctccaggctc gggccccgcc cctctcagcc tctccagccc aggttgctag ggcttggcgg     1200
ggcaaccaaa cctggcgtgc caggaggcgc ggcgcgcgcg tgagcgcgca ggcgagcttg     1260
tataaggaac cagcgttctt cggcttcgga gactcgagca cgagcggcgc gagcccgaac     1320
cccaggacaa gcgcttcctc ctcattggct cctaccagaa gggggcgggg taaaggcggg     1380
atcgggcaaa acctgaggtg ctttcccatt ggtccgaacg ggccggctgg ggcggggcag     1440
ttagcaaaat aggctgcgcg ttcgcttctg ctagagggcg gggccggagg tttcgattag     1500
ttgtctctgc cgctggggaa ggtaaagcgg cgacggcgtc ctcaggagct gtggggtccc     1560
ctgctagaag tggggggactc ggcggggtga gtagtcgcgc cgccacccgc ccgccaagcc     1620 ttcttacccct tacatcggcc ccgcgtccac ccag                                1654
```

```
<210> SEQ ID NO 15
<211> LENGTH: 198
<212> TYPE: DNA
<213> ORGANISM: Unknown
<220> FEATURE:
<221> NAME/KEY: source
<223> OTHER INFORMATION: /note="Description of Unknown:
      SV40 Polyadenylation Signal sequence"

<400> SEQUENCE: 15
gatccagaca tgataagata cattgatgag tttggacaaa ccacaactag aatgcagtga       60
aaaaaatgct ttatttgtga aatttgtgat gctattgctt tatttgtaac cattataagc      120
tgcaataaac aagttaacaa caacaattgc attcatttta tgtttcaggt tcagggggag      180
gtgtgggagg tttttttag                                                    198
```

```
<210> SEQ ID NO 16
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16 gccgccacc                                                                9
```

```
<210> SEQ ID NO 17
<211> LENGTH: 304
<212> TYPE: DNA
<213> ORGANISM: Cytomegalovirus sp.
```

<400> SEQUENCE: 17
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggac tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catg                                                                 304

<210> SEQ ID NO 18
<211> LENGTH: 95
<212> TYPE: DNA
<213> ORGANISM: Unknown
<220> FEATURE:
<221> NAME/KEY: source
<223> OTHER INFORMATION: /note="Description of Unknown:
      SV40 Intron sequence"

<400> SEQUENCE: 18
gctctaaggt aaatataaaa tttttaagtg tataatgtgt taaactactg attctaattg      60
tttctctctt ttagattcca acctttggaa ctgat                                95

<210> SEQ ID NO 19
<211> LENGTH: 3828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagtgc aagtgggttt taggaccagg atgaggcggg     180
gtgggggtgc ctacctgacg accgaccccg acccactgga caagcaccca accccccattc    240 cccaaattgc gcatccccta tcagagaggg ggaggggaaa caggatgcgg cgaggcgcgt     300
gcgcactgcc agcttcagca ccgcggacag tgccttcgcc cccgcctggc ggcgcgcgcc     360
accgccgcct cagcactgaa ggcgcgctga cgtcactcgc cggtcccccg caaactcccc     420
ttcccggcca ccttggtcgc gtccgcgccg ccgccggccc agccggaccg caccacgcga     480
ggcgcgagat aggggggcac gggcgcgacc atctgcgctg cggcgccggc gactcagcgc     540
tgcctcagtc tgcggtgggc agcggaggag tcgtgtcgtg cctgagagcg caggccgcca     600
ccatgaagat tcctaacatt ggtaatgtga tgaataaatt tgagatcctt ggggttgtag     660
gtgaaggagc ctatggagtt gtacttaaat gcagacacaa ggaaacacat gaaattgtgg     720
cgatcaagaa attcaaggac agtgaagaaa atgaagaagt caaagaaacg actttacgag     780
agcttaaaat gcttcggact ctcaagcagg aaaacattgt ggagttgaag gaagcatttc     840
gtcggagggg aaagttgtac ttggtgtttg agtatgttga aaaaaatatg ctcgaattgc     900
tggaagaaat gccaaatgga gttccacctg agaaagtaaa aagctacatc tatcagctaa     960
tcaaggctat tcactggtgc cataagaatg atattgtcca tcgagatata aaaccagaaa    1020
atctcttaat cagccacaat gatgtcctaa aactgtgtga ctttggtttt gctcgtaatc    1080
tgtcagaagg caataatgct aattacacag agtacgttgc caccagatgg tatcggtccc    1140

-continued

```
cagaactctt acttggcgct ccctatggaa agtccgtgga catgtggtcg gtgggctgta      1200
ttcttgggga gcttagcgat ggacagcctt tatttcctgg agaaagtgaa attgaccaac      1260
tttttactat tcagaaggtg ctaggaccac ttccatctga gcagatgaag cttttctaca      1320
gtaatcctcg cttccatggg ctccggtttc cagctgttaa ccatcctcag tccttggaaa      1380
gaagatacct tggaattttg aatagtgttc tacttgacct aatgaagaat ttactgaagt      1440
tggacccagc tgacagatac ttgacagaac agtgtttgaa tcaccctaca tttcaaaccc      1500
agagacttct ggatcgttct ccttcaaggt cagcaaaaag aaaaccttac catgtggaaa      1560
gcagcacatt gtctaataga aaccaagccg gcaaaagtac tgctttgcag tctcaccaca      1620
gatctaacag caaggacatc cagaacctga gtgtaggcct gccccgggct gacgaaggtc      1680
tccctgccaa tgaaagcttc ctaaatggaa accttgctgg agctagtctt agtccactgc      1740
acaccaaaac ctaccaagca agcagccagc ctgggtctac cagcaaagat ctcaccaaca      1800
acaacatacc acaccttctt agcccaaaag aagccaagtc aaaaacagag tttgatttta      1860
atattgaccc aaagccttca gaaggcccag ggacaaagta cctcaagtca aacagcagat      1920
ctcagcagaa ccgccactca ttcatggaaa gctctcaaag caaagctggg acactgcagc      1980
ccaatgaaaa gcagagtcgg catagctata ttgacacaat tccccagtcc tctaggagtc      2040
cctcctacag gaccaaggcc aaaagccatg gggcactgag tgactccaag tctgtgagca      2100
acctttctga gccagggcc caaattgcgg agcccagtac cagtaggtac ttcccatcta      2160
gctgcttaga cttgaattct cccaccagcc caacccccac cagacacagt gacacgagaa      2220
ctttgctcag cccttctgga agaaataacc gaaatgaggg aacgctggac tcacgtcgaa      2280
ccacaaccag acattctaag acgatggagg aattgaagct gccggagcac atggacagta      2340
gccattccca ttcactgtct gcacctcacg aatcttttttc ttatggactg ggctacacca      2400 gcccctttttc ttcccagcaa cgtcctcata ggcattctat gtatgtgacc cgtgacaaag      2460
tgagagccaa gggcttggat ggaagcttga gcatagggca agggatggca gctagagcca      2520
acagcctgca actcttgtca ccccagcctg gagaacagct ccctccagag atgactgtgg      2580
caagatcttc ggtcaaagag acctccagag aaggcacctc ttccttccat acacgccaga      2640
agtctgaggg tggagtgtat catgacccac actctgatga tggcacagcc cccaaagaaa      2700
atagacacct atacaatgat cctgtgccaa ggagagttgg tagcttttac agagtgccat      2760
ctccacgtcc agacaattct ttccatgaaa ataatgtgtc aactagagtt tcttctctac      2820
catcagagag cagttctgga accaaccact caaaaagaca accagcattc gatccatgga      2880
aaagtcctga aaatattagt cattcagagc aactcaagga aaaagagaag caaggatttt      2940
tcaggtcaat gaaaaagaaa aagaagaaat ctcaaacagt acccaattcc gacagccctg      3000
atcttctgac gttgcagaaa tccattcatt ctgctagcac tccaagcagc agaccaaagg      3060
agtggcgccc cgagaagatc tcagatctgc agacccaaag ccagccatta aaatcactgc      3120
gcaagttgtt acatctctct tcggcctcaa atcacccggc ttcctcagat ccccgcttcc      3180
agcccttaac agctcaacaa accaaaaatt ccttctcaga aattcggatt cacccccctga      3240 gccaggcctc tggcgggagc agcaacatcc ggcaggaacc cgcaccgaag ggcaggccag      3300
ccctccagct gccaggtcag atggatcctg gttggcatgt gtcctctgtg accaggagtg      3360
ccacagaggg cccttcctac tctgaacagc tgggtgccaa aagtgggcca aatgggcacc      3420
cctataacag aacaaatcgc tcacgaatgc caaatctgaa tgatttaaaa gagacagcct      3480
```

-continued

```
tgtaagatcc agacatgata agatacattg atgagtttgg acaaaccaca actagaatgc      3540
agtgaaaaaa atgctttatt tgtgaaattt gtgatgctat tgctttattt gtaaccatta      3600
taagctgcaa taaacaagtt aacaacaaca attgcattca ttttatgttt caggttcagg      3660
gggaggtgtg ggaggttttt tagaggaacc cctagtgatg gagttggcca ctccctctct      3720
gcgcgctcgc tcgctcactg aggccgcccg ggcaaagccc gggcgtcggg cgacctttgg      3780
tcgcccggcc tcagtgagcg agcgagcgcg cagagaggga gtggccaa                   3828
```

```
<210> SEQ ID NO 20
<211> LENGTH: 4057
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
```

```
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcctcgtta cataacttac ggtaaatggc ccgcctggct       180
gaccgcccaa cgacccccgc ccattgacgt caataatgac gtatgttccc atagtaacgc       240
caatagggac tttccattga cgtcaatggg tggactattt acggtaaact gcccacttgg       300
cagtacatca agtgtatcat atgccaagta cgcccctat tgacgtcaat gacggtaaat        360
ggcccgcctg gcattatgcc cagtacatga ccttatggga ctttcctact ggcagtaca       420 tctacgtatt agtcatcgct attaccatgc gtcgaggtga gccccacgtt ctgcttcact       480
ctccccatct cccccccctc cccacccca attttgtatt tatttatttt ttaattattt      540
tatgcagcga tgggggcggg gggggggggg gcgcgcgcca ggcggggcgg ggcggggcga       600
ggggcggggc gggcgaggc ggagaggtgc ggcggcagcc aatcagagcg gcgcgctccg        660
aaagtttcct tttatggcga ggcggcggcg gcggcggccc tataaaaagc gaagcgcgcg       720
gcgggcggct ctaaggtaaa tataaaattt ttaagtgtat aatgtgttaa actactgatt       780
ctaattgttt ctctctttta gattccaacc tttggaactg atgccgccac catgaagatt      840
cctaacattg gtaatgtgat gaataaattt gagatccttg gggttgtagg tgaaggagcc       900
tatggagttg tacttaaatg cagacacaag gaaacacatg aaattgtggc gatcaagaaa       960
ttcaaggaca gtgaagaaaa tgaagaagtc aaagaaacga ctttacgaga gcttaaaatg      1020
cttcggactc tcaagcagga aaacattgtg gagttgaagg aagcatttcg tcggagggga      1080
aagttgtact tggtgtttga gtatgttgaa aaaaatatgc tcgaattgct ggaagaaatg      1140
ccaaatggag ttccacctga aaagtaaaa agctacatct atcagctaat caaggctatt       1200
cactggtgcc ataagaatga tattgtccat cgagatataa aaccagaaaa tctcttaatc      1260
agccacaatg atgtcctaaa actgtgtgac tttggttttg ctcgtaatct gtcagaaggc      1320
aataatgcta attacacaga gtacgttgcc accagatggt atcggtcccc agaactctta      1380
cttggcgctc cctatggaaa gtccgtggac atgtggtcgg tgggctgtat tcttgggag       1440 cttagcgatg gacagccttt atttcctgga gaaagtgaaa ttgaccaact tttttactatt     1500 cagaaggtgc taggaccact tccatctgag cagatgaagc ttttctacag taatcctcgc      1560
ttccatgggc tccggtttcc agctgttaac catcctcagt ccttggaaag aagataacctt     1620 ggaattttga atagtgttct acttgaccta atgaagaatt tactgaagtt ggacccagct      1680
```

-continued

```
gacagatact tgacagaaca gtgtttgaat caccctacat ttcaaaccca gagacttctg      1740
gatcgttctc cttcaaggtc agcaaaaaga aaaccttacc atgtggaaag cagcacattg      1800
tctaatagaa accaagccgg caaaagtact gctttgcagt ctcaccacag atctaacagc      1860
aaggacatcc agaacctgag tgtaggcctg ccccgggctg acgaaggtct ccctgccaat      1920
gaaagcttcc taaatggaaa ccttgctgga gctagtctta gtccactgca caccaaaacc      1980
taccaagcaa gcagccagcc tgggtctacc agcaaagatc tcaccaacaa caacatacca      2040
caccttctta gcccaaaaga agccaagtca aaaacagagt ttgattttaa tattgaccca      2100
aagccttcag aaggcccagg acaaagtac ctcaagtcaa acagcagatc tcagcagaac      2160
cgccactcat tcatggaaag ctctcaaagc aaagctggga cactgcagcc caatgaaaag      2220
cagagtcggc atagctatat tgacacaatt ccccagtcct ctaggagtcc ctcctacagg      2280
accaaggcca aaagccatgg ggcactgagt gactccaagt ctgtgagcaa cctttctgaa      2340
gccagggccc aaattgcgga gcccagtacc agtaggtact tcccatctag ctgcttagac      2400
ttgaattctc ccaccagccc aacccccacc agacacagtg acacgagaac tttgctcagc      2460
ccttctggaa gaaataaccg aaatgaggga acgctggact cacgtcgaac cacaaccaga      2520
cattctaaga cgatggagga attgaagctg ccggagcaca tggacagtag ccattcccat      2580
tcactgtctg cacctcacga atcttttttct tatggactgg gctacaccag ccccttttct      2640
tcccagcaac gtcctcatag gcattctatg tatgtgaccc gtgacaaagt gagagccaag      2700
ggcttggatg gaagcttgag catagggcaa gggatggcag ctagagccaa cagcctgcaa      2760
ctcttgtcac cccagcctgg agaacagctc cctccagaga tgactgtggc aagatcttcg      2820
gtcaaagaga cctccagaga aggcacctct tccttccata cacgccagaa gtctgagggt      2880
ggagtgtatc atgacccaca ctctgatgat ggcacagccc ccaaagaaaa tagacaccta      2940
tacaatgatc ctgtgccaag gagagttggt agcttttaca gagtgccatc tccacgtcca      3000
gacaattctt ccatgaaaaa taatgtgtca actagagttt cttctctacc atcagagagc      3060
agttctggaa ccaaccactc aaaaagacaa ccagcattcg atccatggaa aagtcctgaa      3120
aatattagtc attcagagca actcaaggaa aaagagaagc aaggattttt caggtcaatg      3180
aaaaagaaaa agaagaaatc tcaaacagta cccaattccg acagccctga tcttctgacg      3240
ttgcagaaat ccattcattc tgctagcact ccaagcagca gaccaaagga gtggcgcccc      3300
gagaagatct cagatctgca gacccaaagc cagccattaa aatcactgcg caagttgtta      3360
catctctctt cggcctcaaa tcacccggct tcctcagatc cccgcttcca gcccttaaca      3420
gctcaacaaa ccaaaaattc cttctcagaa attcggattc accccctgag ccaggcctct      3480
ggcgggagcc gcaacatccg gcaggaaccc gcaccgaagg gcaggccagc cctccagctg      3540
ccaggtcaga tggatcctgg ttggcatgtg tcctctgtga ccaggagtgc cacagagggc      3600
ccttcctact ctgaacagct gggtgccaaa agtgggccaa atgggcaccc ctataacaga      3660
acaaatcgct cacgaatgcc aaatctgaat gatttaaaag agacagcctt gtaagatcca      3720
gacatgataa gatacattga tgagtttgga caaccacaa ctagaatgca gtgaaaaaaa      3780
tgctttattt gtgaaatttg tgatgctatt gctttatttg taaccattat aagctgcaat      3840
aaacaagtta acaacaacaa ttgcattcat tttatgtttc aggttcaggg ggaggtgtgg      3900
gaggtttttt agaggaaccc ctagtgatgg agttggccac tccctctctg cgcgctcgct      3960
cgctcactga ggccgcccgg gcaaagcccg ggcgtcgggc gacctttggt cgcccggcct      4020
```

-continued

```
cagtgagcga gcgagcgcgc agagagggag tggccaa                        4057

<210> SEQ ID NO 21
<211> LENGTH: 2211
<212> TYPE: DNA
<213> ORGANISM: Adeno-associated virus 9

<400> SEQUENCE: 21
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct ccgggttac aaataccttg acccggcaa cggactcgac    180 aagggggagc cggtcaacgc agcagacgcg gcggccctcg agcacgacaa ggcctacgac    240
cagcagctca aggccggaga caacccgtac ctcaagtaca ccacgccga cgccgagttc    300 caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600 cttacaatgg cttcaggtgg tggcgcacca gtggcagaca ataacgaagg tgccgatgga    660
gtgggtagtt cctcgggaaa ttggcattgc gattcccaat ggctgggga cagagtcatc    720 accaccagca cccgaacctg ggcctgccc acctacaaca atcacctcta caagcaaatc    780
tccaacagca catctggagg atcttcaaat gacaacgcct acttcggcta cagcacccc    840 tggggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620 ttaattttg gcaaacaagg aactggaaga acaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg ctgggttca aaaccaagga   1800 atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc tcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
```

-continued

```
tacacttcca actattacaa gtctaataat gttgaatttg ctgttaatac tgaaggtgta      2160
tatagtgaac cccgccccat tggcaccaga tacctgactc gtaatctgta a               2211
```

<210> SEQ ID NO 22
<211> LENGTH: 736
<212> TYPE: PRT
<213> ORGANISM: Adeno-associated virus 9

<400> SEQUENCE: 22

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350
```

-continued

```
Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 23
<211> LENGTH: 310
<212> TYPE: PRT
<213> ORGANISM: Streptococcus pyogenes

<400> SEQUENCE: 23

-continued

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
                20                  25                  30

Phe Thr Gln Gly Glu Asp Val Phe His Ala Pro Tyr Val Ala Asn Gln
            35                  40                  45

Gly Trp Tyr Asp Ile Thr Lys Thr Phe Asn Gly Lys Asp Asp Leu Leu
        50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
            115                 120                 125

Glu Lys Ala Phe Pro Tyr Leu Ser Thr Lys His Leu Gly Val Phe Pro
        130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
            195                 200                 205

Leu Ile Lys Lys Glu Leu Thr Glu Gly Lys Ala Leu Gly Leu Ser His
        210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp Asn Gln Thr Asn
305                 310

<210> SEQ ID NO 24
<211> LENGTH: 349
<212> TYPE: PRT
<213> ORGANISM: Streptococcus equi

<400> SEQUENCE: 24

Met Lys Thr Ile Ala Tyr Pro Asn Lys Pro His Ser Leu Ser Ala Gly
1               5                   10                  15

Leu Leu Thr Ala Ile Ala Ile Phe Ser Leu Ala Ser Ser Asn Ile Thr
                20                  25                  30

Tyr Ala Asp Asp Tyr Gln Arg Asn Ala Thr Glu Ala Tyr Ala Lys Glu
            35                  40                  45

Val Pro His Gln Ile Thr Ser Val Trp Ser Lys Gly Val Thr Pro Leu

-continued

```
          50                    55                    60

Thr Pro Glu Gln Phe Arg Tyr Asn Asn Glu Asp Val Ile His Ala Pro
65                    70                    75                    80

Tyr Leu Ala His Gln Gly Trp Tyr Asp Ile Thr Lys Ala Phe Asp Gly
                   85                    90                    95

Lys Asp Asn Leu Leu Cys Gly Ala Ala Thr Ala Gly Asn Met Leu His
               100                   105                   110

Trp Trp Phe Asp Gln Asn Lys Thr Glu Ile Glu Ala Tyr Leu Ser Lys
           115                   120                   125

His Pro Glu Lys Gln Lys Ile Ile Phe Asn Asn Gln Glu Leu Phe Asp
       130                   135                   140

Leu Lys Ala Ala Ile Asp Thr Lys Asp Ser Gln Thr Asn Ser Gln Leu
145                   150                   155                   160

Phe Asn Tyr Phe Arg Asp Lys Ala Phe Pro Asn Leu Ser Ala Arg Gln
               165                   170                   175

Leu Gly Val Met Pro Asp Leu Val Leu Asp Met Phe Ile Asn Gly Tyr
               180                   185                   190

Tyr Leu Asn Val Phe Lys Thr Gln Ser Thr Asp Val Asn Arg Pro Tyr
           195                   200                   205

Gln Asp Lys Asp Lys Arg Gly Gly Ile Phe Asp Ala Val Phe Thr Arg
       210                   215                   220

Gly Asp Gln Thr Thr Leu Leu Thr Ala Arg His Asp Leu Lys Asn Lys
225                   230                   235                   240

Gly Leu Asn Asp Ile Ser Thr Ile Ile Lys Gln Glu Leu Thr Glu Gly
               245                   250                   255

Arg Ala Leu Ala Leu Ser His Thr Tyr Ala Asn Val Ser Ile Ser His
               260                   265                   270

Val Ile Asn Leu Trp Gly Ala Asp Phe Asn Ala Glu Gly Asn Leu Glu
               275                   280                   285

Ala Ile Tyr Val Thr Asp Ser Asp Ala Asn Ala Ser Ile Gly Met Lys
       290                   295                   300

Lys Tyr Phe Val Gly Ile Asn Ala His Gly His Val Ala Ile Ser Ala
305                   310                   315                   320

Lys Lys Ile Glu Gly Glu Asn Ile Gly Ala Gln Val Leu Gly Leu Phe
               325                   330                   335

Thr Leu Ser Ser Gly Lys Asp Ile Trp Gln Lys Leu Ser
           340                   345
```

GENE THERAPY FOR TREATING CDKL5 DEFICIENCY DISORDER

CROSS-REFERENCE TO RELATED APPLICATIONS

The present application is a U.S. national stage application, filed under 35 U.S.C. § 371, of International Application No. PCT/US2021/017656, filed on Feb. 11, 2021, which claims the benefit of and priority to U.S. Provisional Application No. 62/976,483, filed on Feb. 14, 2020; and to U.S. Provisional Application No. 63/090,492, filed on Oct. 12, 2020, the entire disclosure of each of which are incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Feb. 8, 2021, is named ULP-007WO_SL.txt and is 80,765 bytes in size.

TECHNICAL FIELD OF THE INVENTION

The present disclosure relates generally to recombinant adeno-associated viral vectors, recombinant adeno-associated virus, and methods of their use in gene therapy for treating CDKL5 deficiency disorder.

BACKGROUND OF THE INVENTION

CDKL5 deficiency disorder (CDD) is a rare neurodevelopmental disease caused by mutations in the CDKL5 gene which can manifest in a broad range of clinical symptoms and severity. Hallmarks of CDD include infantile-onset refractory epilepsy, developmental delay, intellectual disability, visual impairment, lack of speech, hypotonia, motor dysfunction, sleep disturbances, gastrointestinal dysfunction, and breathing difficulties. Although rare, the occurrence is believed to be approximately 1 in 40,000-60,000 live births, making it one of the most common forms of genetic epilepsy.

The CDKL5 gene encodes a cyclin-dependent kinase-like 5 (CDKL5) protein that is essential for normal brain development and function. The CDKL5 protein is involved in the formation, growth, and migration of neurons in the brain. It is widely expressed in the brain, predominantly in neurons and dendrites, with roles in cell proliferation, neuronal migration, axonal outgrowth, dendritic morphogenesis, and synapse development.

CDD is caused by pathogenic variants in the CDKL5 gene that include deletions, truncations, splice variants, and missense mutations. See Olson et al., 2019, *Pediatric Neurology* 97: 18-25. These variants can reduce the amount of functional CDKL5 protein and/or diminish its activity in neurons. More than 150 mutations in the CDKL5 gene have been found to cause CDD. See Del Rosso et al., 2017, *The EuroBiotech Journal* 1(2): 122-127.

To date, there is no treatment that addresses the underlying cause of CDD, namely the deficiency of CDKL5. At present, CDD patients generally require 24/7 care due to significant motor and intellectual disability. Furthermore, seizures experienced by CDD patients are typically not well-controlled with existing anti-epileptic drugs. Accordingly, a therapeutic approach that addresses the underlying cause of the disease—the deficiency of functional CDKL5—is urgently needed.

The present invention addresses this need via the creation of adeno-associated viral vectors that mediate the transfer of a gene encoding functional CDKL5 to patients with CDD. The present invention also describes the creation of recombinant adeno-associated virus (rAAV) that delivers a gene encoding functional CDKL5 to patients with CDD.

SUMMARY OF THE INVENTION

This invention provides compositions and methods of their use in gene therapy. More specifically, provided herein are recombinant adeno-associated virus (rAAV) comprising an adeno-associated virus (AAV) capsid and a vector genome packaged therein useful for the treatment of CDD.

In one aspect, the present disclosure provides a recombinant adeno-associated virus (rAAV) comprising an AAV capsid, and a vector genome packaged therein, wherein said vector genome comprises: (a) a promoter sequence and (b) a partial or complete coding sequence for CDKL5 or an isoform thereof, or a functional fragment or functional variant thereof.

In another aspect, the present disclosure provides a recombinant adeno-associated virus (rAAV) comprising an AAV capsid, and a vector genome packaged therein, wherein said vector genome comprises: (a) a 5'-inverted terminal repeat sequence (5'-ITR) sequence; (b) a promoter sequence; (c) a partial or complete coding sequence for CDKL5 or an isoform thereof, or a functional fragment or functional variant thereof and (d) a 3'-inverted terminal repeat sequence (3'-ITR) sequence.

In yet another aspect, the present disclosure provides an rAAV comprising an AAV capsid, and a vector genome packaged therein, wherein said vector genome comprises: (a) a 5'-ITR sequence; (b) a promoter sequence; (c) a partial or complete coding sequence for CDKL5 or an isoform thereof, or a functional fragment or functional variant thereof; (d) a polyadenylation signal sequence; and (e) a 3'-ITR sequence.

In yet another aspect, the present disclosure provides an rAAV comprising an AAV capsid, and a vector genome packaged therein, wherein said vector genome comprises: (a) a 5'-ITR sequence; (b) an enhancer sequence; (c) a promoter sequence; (d) an intron sequence; (e) a partial or complete coding sequence for CDKL5 or an isoform thereof, or a functional fragment or functional variant thereof; (f) a polyadenylation signal sequence; and (g) a 3'-ITR sequence.

In one embodiment, the partial or complete coding sequence for CDKL5 is a wild-type coding sequence. In an alternative embodiment, the partial or complete coding sequence for CDKL5 is a codon-optimized coding sequence. In one exemplary embodiment, the partial or complete coding sequence for CDKL5 is codon-optimized for expression in humans. In some embodiments, the partial or complete coding sequence for CDKL5 comprises a sequence which is at least 80%, at least 85%, at least 90%, at least 91%, at least 92%, at least 93%, at least 94%, at least 95%, at least 96%, at least 97%, at least 98%, at least 99% or more identical to a sequence selected from SEQ ID NOs: 1-8.

In some embodiments, the present disclosure provides an rAAV comprising an AAV capsid and a vector genome packaged therein, wherein said vector genome comprises: (a) a promoter sequence and (b) a coding sequence for CDKL5 comprising a sequence which is at least 95% identical to a sequence selected from SEQ ID NOs: 1, 2, 3, 4, 5, 6, 7, and 8.

In some embodiments, CDKL5 is encoded by the wild-type coding sequence shown in SEQ ID NO: 1. In another embodiment, a coding sequence expressing a variant or alternative natural isoform of CDKL5 may be used, such as the coding sequence shown in SEQ ID NO: 2. In certain embodiments, CDKL5 is encoded by a codon-optimized coding sequence. In some embodiments, CDKL5 is encoded by a codon-optimized coding sequence that is less than 80% identical to a wild-type coding sequence shown in SEQ ID NO: 1 or SEQ ID NO: 2. In some exemplary embodiments, CDKL5 is encoded by a codon-optimized coding sequence selected from SEQ ID NOs: 3-8. In some embodiments, CDKL5 is encoded by a codon-optimized coding sequence which is at least 80% identical to a sequence selected from SEQ ID NOs: 3-8. In some embodiments, CDKL5 is encoded by a codon-optimized coding sequence which is at least 90% identical to a sequence selected from SEQ ID NOs: 3-8. In some embodiments, CDKL5 is encoded by a codon-optimized coding sequence which is at least 95% identical to a sequence selected from SEQ ID NOs: 3-8. In some embodiments, the coding sequence for CDKL5 may further comprise a stop codon (TGA, TAA, or TAG) at the 3' end. In some embodiments, the expressed CDKL5 protein comprises or consists of an amino acid sequence of SEQ ID NO: 9. In some embodiments, the expressed CDKL5 protein comprises or consists of an amino acid sequence of SEQ ID NO: 10.

In some embodiments, the promoter is a neuron-specific promoter. In one embodiment, the neuron-specific promoter is selected from a human synapsin 1 (SYN1) promoter, a mouse calcium/calmodulin-dependent protein kinase II (CaMKII) promoter, a rat tubulin alpha I (Ta1) promoter, a rat neuron-specific enolase (NSE) promoter, a human neuron-specific enolase (ENO2) promoter, a human platelet-derived growth factor-beta chain (PDGF) promoter, a human BM88 promoter, and a neuronal nicotinic receptor (32 (CHRNB2) promoter.

In an exemplary embodiment, the neuron-specific promoter is the SYN1 promoter (e.g., human SYN1 promoter). In one embodiment, the SYN1 promoter (e.g., a human SYN1 promoter) has a nucleic acid sequence that comprises or consists of SEQ ID NO: 12.

In some embodiments, the promoter is selected from a chicken β-actin (CBA) promoter, a cytomegalovirus (CMV) immediate early gene promoter, a transthyretin (TTR) promoter, a thyroxine binding globulin (TBG) promoter, and an alpha-1 anti-trypsin (A1AT) promoter.

In an exemplary embodiment, the promoter is the CBA promoter. In one embodiment, the CBA promoter has a nucleic acid sequence that comprises or consists of SEQ ID NO: 13.

In some embodiments, the promoter is a gene-specific endogenous promoter. In one embodiment, the promoter comprises native gene promoter elements. In an exemplary embodiment, the promoter is the CDKL5 gene-specific endogenous promoter comprising a nucleotide sequence of at least 15 continuous nucleotides, which is at least 95% identical to an equal length region of SEQ ID NO: 14.

In some embodiments, the packaged vector genome comprises a 5'-ITR sequence and/or a 3'-ITR sequence. In certain embodiments, the 5'-ITR sequence is from AAV2. In certain embodiments, the 3'-ITR sequence is from AAV2. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11. In other embodiments, the 5'-ITR sequence and/or the 3'-ITR sequence are from a non-AAV2 source.

In some embodiments, the packaged vector genome comprises a polyadenylation signal sequence. In one embodiment, the polyadenylation signal sequence is selected from an SV40 polyadenylation signal sequence, a bovine growth hormone (BGH) polyadenylation signal sequence, and a rabbit beta globin polyadenylation signal sequence. In an exemplary embodiment, the polyadenylation signal sequence is the SV40 polyadenylation signal sequence. In one embodiment, the SV40 polyadenylation signal sequence comprises or consists of SEQ ID NO: 15.

In some embodiments, the packaged vector genome comprises a consensus Kozak sequence. In one embodiment, the consensus Kozak sequence is GCCGCCACC (SEQ ID NO: 16). In certain embodiments, the consensus Kozak sequence is located upstream of the coding sequence for CDKL5.

In some embodiments, the packaged vector genome comprises one or more enhancer sequences. In one embodiment, the enhancer is selected from a cytomegalovirus (CMV) immediate early gene enhancer, a transthyretin enhancer (enTTR), a chicken β-actin (CBA) enhancer, an En34 enhancer, and an apolipoprotein E (ApoE) enhancer. In an exemplary embodiment, the enhancer is the CMV enhancer (e.g., the CMV immediate early gene enhancer). In one embodiment, the CMV enhancer (e.g., the CMV immediate early gene enhancer) has a sequence that comprises or consists of SEQ ID NO: 17. In certain embodiments, the enhancer is located upstream of the promoter sequence.

In some embodiments, the packaged vector genome comprises one or more intron sequences. In one embodiment, the intron is selected from an SV40 Small T intron, a rabbit hemoglobin subunit beta (rHBB) intron, a human beta globin IV S2 intron, a β-globin/IgG chimeric intron, and an hFIX intron. In one exemplary embodiment, the intron is the SV40 Small T intron. In one embodiment, the SV40 Small T intron sequence comprises or consists of SEQ ID NO: 18.

In some embodiments, the AAV capsid is from an AAV of serotype 1, 2, 3, 4, 5, 6, 7, 8, 9, 10, 11, 12, rh10, hu37 (i.e., AAV1, AAV2, AAV3, AAV4, AAV5, AAV6, AAV7, AAV9, AAV10, AAV11, AAV12, AAVrh10, AAVhu37), or an engineered variant thereof. In an exemplary embodiment, the AAV capsid is an AAV serotype 9 (AAV9) capsid, an AAV9 variant capsid, an AAV serotype 8 (AAV8) capsid, an AAV8 variant capsid, or an AAV serotype hu37 (AAVhu37) capsid.

In some aspects, the present disclosure provides novel codon-optimized nucleic acid sequences encoding CDKL5. In one embodiment, the codon-optimized nucleic acid sequence encoding CDKL5 is less than 80% identical to a wild-type coding sequence shown in SEQ ID NO: 1 or SEQ ID NO: 2. In some embodiments, the codon-optimized nucleic acid sequence encoding CDKL5 is at least 80%, at least 85%, at least 90%, at least 91%, at least 92%, at least 93%, at least 94%, at least 95%, at least 96%, at least 97%, at least 98%, at least 99% or more identical to a sequence selected from SEQ ID NOs: 3-8. In some embodiments, the present disclosure provides nucleic acid sequences which are less than 80% identical to a wild-type coding sequence shown in SEQ ID NO: 1 or SEQ ID NO: 2 and are at least 80%, at least 85%, at least 90%, at least 91%, at least 92%, at least 93%, at least 94%, at least 95%, at least 96%, at least 97%, at least 98%, at least 99% or more identical to a sequence selected from SEQ ID NOs: 3-8. In exemplary embodiments, the present disclosure provides a nucleic acid sequence encoding CDKL5 selected from a sequence selected from SEQ ID NOs: 3-8. Further provided are fragments of the nucleic acid sequences shown in SEQ ID NOs: 3-8 which encode a polypeptide having functional CDKL5 activity. In some embodiments, the nucleic acid sequence encoding CDKL5 may further comprise a stop codon (TGA, TAA, or TAG) at the 3' end.

In some aspects, the present disclosure provides novel vector genome constructs useful in the treatment of CDD. In some embodiments, the present disclosure provides a vector genome construct (i.e., a polynucleotide) encoding CDKL5 that is at least 80%, at least 85%, at least 90%, at least 91%, at least 92%, at least 93%, at least 94%, at least 95%, at least 96%, at least 97%, at least 98%, at least 99% or more identical to a nucleic acid sequence selected from SEQ ID NOs: 19-20. In one embodiment, the present disclosure provides a polynucleotide which comprises a nucleic acid sequence at least 95% identical to SEQ ID NO: 19. In one embodiment, the present disclosure provides a polynucleotide whose nucleic acid sequence comprises or consists of SEQ ID NO: 19. In one embodiment, the present disclosure provides a polynucleotide which comprises a nucleic acid sequence at least 95% identical to SEQ ID NO: 20. In another embodiment, the present disclosure provides a polynucleotide whose nucleic acid sequence comprises or consists of SEQ ID NO: 20.

In certain embodiments, the present disclosure provides recombinant adeno-associated virus (rAAV) useful as agents for gene therapy in the treatment of CDD, wherein said rAAV comprises an AAV capsid and a vector genome as described herein packaged therein. In some embodiments, the AAV capsid is from an AAV of serotype 1, 2, 3, 4, 5, 6, 7, 8, 9, 10, 11, 12, rh10, hu37 (i.e., AAV1, AAV2, AAV3, AAV4, AAV5, AAV6, AAV7, AAV9, AAV10, AAV11, AAV12, AAVrh10, AAVhu37), or an engineered variant thereof. In an exemplary embodiment, the AAV capsid is an AAV serotype 9 (AAV9) capsid, an AAV9 variant capsid, an AAV serotype 8 (AAV8) capsid, an AAV8 variant capsid, or an AAV serotype hu37 (AAVhu37) capsid.

In certain embodiments, the present disclosure provides an rAAV useful for the treatment of CDKL5 deficiency disorder (CDD), wherein said rAAV comprises an AAV capsid and a vector genome packaged therein, and wherein said vector genome comprises: (a) a promoter sequence and (b) a partial or complete coding sequence for CDKL5 or an isoform thereof, or a functional fragment or functional variant thereof. In some embodiments, the coding sequence for CDKL5 comprises a sequence which is at least 95% identical to a sequence selected from SEQ ID NOs: 1-8.

In certain embodiments, the present disclosure provides an rAAV useful for the treatment of CDKL5 deficiency disorder (CDD), wherein said rAAV comprises an AAV capsid and a vector genome packaged therein, and wherein said vector genome comprises: (a) a 5'-ITR sequence; (b) a promoter sequence; (c) a coding sequence for CDKL5 comprising a sequence which is at least 95% identical to a sequence selected from SEQ ID NOs: 1-8; (d) a polyadenylation signal sequence; and (e) a 3'-ITR sequence.

In certain embodiments, the present disclosure provides an rAAV useful for the treatment of CDKL5 deficiency disorder (CDD), wherein said rAAV comprises an AAV9 capsid and a vector genome packaged therein, and wherein said vector genome comprises: (a) a 5'-ITR sequence; (b) a promoter sequence; (c) a coding sequence for CDKL5 comprising a sequence which is at least 95% identical to a sequence selected from SEQ ID NOs: 1-8; (d) a polyadenylation signal sequence; and (e) a 3'-ITR sequence.

In certain embodiments, the present disclosure provides an rAAV useful for the treatment of CDKL5 deficiency disorder (CDD), wherein said rAAV comprises an AAV9 capsid and a vector genome packaged therein, and wherein said vector genome comprises: (a) an AAV2 5'-ITR sequence; (b) a SYN1 promoter sequence (e.g., a human SYN1 promoter sequence); (c) a coding sequence for CDKL5 comprising a sequence which is at least 95% identical to a sequence selected from SEQ ID NOs: 1-8; (d) an SV40 polyadenylation signal sequence; and (e) an AAV2 3'-ITR sequence. In an exemplary embodiment, the coding sequence for CDKL5 comprises or consists of SEQ ID NO: 1.

In certain embodiments, the present disclosure provides an rAAV useful for the treatment of CDKL5 deficiency disorder (CDD), wherein said rAAV comprises an AAV9 capsid and a vector genome packaged therein, and wherein said vector genome comprises: (a) a 5'-ITR sequence; (b) an enhancer sequence; (c) a promoter sequence; (d) an intron sequence; (e) a coding sequence for CDKL5 comprising a sequence which is at least 95% identical to a sequence selected from SEQ ID NOs: 1-8; (f) a polyadenylation signal sequence; and (g) a 3'-ITR sequence.

In certain embodiments, the present disclosure provides an rAAV useful for the treatment of CDKL5 deficiency disorder (CDD), wherein said rAAV comprises an AAV9 capsid and a vector genome packaged therein, and wherein said vector genome comprises: (a) an AAV2 5'-ITR sequence; (b) a CMV enhancer sequence (e.g., a CMV immediate early gene sequence); (c) a CBA promoter sequence; (d) an SV40 Small T intron sequence; (e) a coding sequence for CDKL5 comprising a sequence which is at least 95% identical to a sequence selected from SEQ ID NOs: 1-8; (0 an SV40 polyadenylation signal sequence; and (g) a AAV2 3'-ITR sequence. In an exemplary embodiment, the coding sequence for CDKL5 comprises or consists of SEQ ID NO: 1.

In some aspects, the present disclosure provides the use of an rAAV disclosed herein for the treatment of CDD, wherein the rAAV includes an AAV capsid and a vector genome packaged therein. In some embodiments, the rAAV contains a packaged genome comprising as operably linked components: a 5'-ITR, a promoter sequence, a partial or complete coding sequence for CDKL5 or an isoform thereof, or a functional fragment or functional variant thereof, and a 3'-ITR. In some embodiments, the packaged genome also comprises at least one of the following elements: (a) an enhancer sequence upstream of the promoter sequence, (b) an intron downstream of the promoter, and (c) a polyadenylation sequence upstream of the 3'-ITR. In one exemplary embodiment, the rAAV contains a packaged genome comprising as operably linked components: an AAV2 5'-ITR sequence, a SYN1 promoter (e.g., a human SYN1 promoter), a coding sequence for CDKL5, an SV40 polyadenylation signal sequence, and an AAV2 3'-ITR. In some embodiments, the coding sequence for CDKL5 comprises a sequence which is at least 95% identical to a sequence selected from SEQ ID NOs: 1-8. In some embodiments, the capsid is an AAV9 capsid.

The present disclosure further relates to pharmaceutical compositions comprising an rAAV disclosed herein. In some embodiments, the pharmaceutical composition comprises a pharmaceutically acceptable carrier or excipient. In some embodiments, the pharmaceutical composition comprising an rAAV is formulated for subcutaneous, intramuscular, intradermal, intraperitoneal, intrathecal, intracerebroventricular, or intravenous administration. In an exemplary embodiment, the pharmaceutical composition is formulated for intrathecal administration.

In yet another aspect, the present disclosure provides methods of treating CDD in a human subject comprising administering to the human subject a therapeutically effective amount of at least one rAAV disclosed herein. In one embodiment, the present disclosure provides a method of treating CDD comprising administering an rAAV that includes an AAV capsid and a vector genome packaged therein, wherein the vector genome comprises a partial or complete coding sequence for CDKL5 or an isoform thereof, or a functional fragment or functional variant thereof. In some embodiments, the method may further comprise administration of an IgG-degrading protease (e.g., the *Streptococcus pyogenes* IdeS or the *Streptococcus equi* IdeZ) prior to administration of the rAAV. In some embodiments, the present disclosure provides a method of treating CDKL5 deficiency disorder (CDD) in a human subject comprising administering a therapeutically effective amount of at least one rAAV disclosed herein, wherein the human subject has been administered an IgG-degrading protease.

In yet another aspect, the present disclosure provides a method of treating a CNS disorder in a human subject comprising first administering to the subject a corticosteroid and then subsequently administering a therapeutically effective amount of at least one rAAV designed for treatment of said CNS disorder, wherein the rAAV is administered intrathecally, intracerebroventricularly, or via intracisterna magna delivery. In some embodiments, the present disclosure provides a method of treating CDKL5 deficiency disorder (CDD) in a human subject comprising administering to a human subject a therapeutically effective amount of a recombinant adeno-associated virus (rAAV), wherein said rAAV comprises an AAV capsid and a vector genome packaged therein, wherein said vector genome comprises a promoter sequence and a coding sequence for CDKL5, and wherein the human subject has been administered a corticosteroid. In one embodiment, the corticosteroid is selected from prednisolone, prednisone, dexamethasone, hydrocortisone, triamcinolone, methylprednisolone, budesonide, betamethasone, and deflazacort. In an exemplary embodiment, the corticosteroid is prednisolone. In one embodiment, the CNS disorder is selected from CDD, Angelman syndrome, Batten disease, Krabbe disease, Parkinson's disease, Alzheimer's disease, Spinal Muscular Atrophy (SMA) Types I, II, III, and IV, X-linked Myotubular Myopathy, Friedrich's Ataxia, Canavan's, Amyotrophic Lateral Sclerosis (ALS), Adrenoleukodystrophy, Huntington disease, Rett syndrome, and Spinocerebellar ataxia. In an exemplary embodiment, the CNS disorder is CDD and the rAAV comprises an rAAV useful for the treatment of CDD described herein.

In certain embodiments, the present disclosure provides methods of treating CDD in a human subject comprising administering to a human subject diagnosed with at least one mutation in CDKL5 a therapeutically effective amount of at least one rAAV disclosed herein. In one embodiment, the present disclosure provides a method of treating CDD in a human subject diagnosed with at least one mutation in CDKL5 comprising administering an rAAV that includes an AAV capsid and a vector genome packaged therein, wherein the vector genome comprises a partial or complete coding sequence for CDKL5 or an isoform thereof, or a functional fragment or functional variant thereof. In some embodiments, the coding sequence for CDKL5 is selected from SEQ ID NOs: 1-8. In some embodiments, the capsid is an AAV9 capsid.

In some embodiments, the rAAV is administered subcutaneously, intramuscularly, intradermally, intraperitoneally, intrathecally, intracerebroventricularly, intravenously, or via intracisterna magna delivery. In an exemplary embodiment, the rAAV is administered intrathecally. In another exemplary embodiment, the rAAV is administered via the cisterna magna. In some embodiments, the rAAV is administered at a dose of about $1\times10^{11}$ to about $1\times10^{14}$ genome copies (GC)/kg. In further embodiments, the rAAV is administered at a dose of about $1\times10^{12}$ to about $1\times10^{13}$ genome copies (GC)/kg. In some embodiments, a single dose of rAAV is administered. In other embodiments, multiple doses of rAAV are administered.

In some aspects, provided herein are host cells comprising a recombinant nucleic acid molecule, an AAV vector, or an rAAV disclosed herein. In specific embodiments, the host cells may be suitable for the propagation of AAV. In certain embodiments, the host cell is selected from a HeLa, Cos-7, HEK293, A549, BHK, Vero, RD, HT-1080, ARPE-19, and MRC-5 cell.

These and other aspects and features of the invention are described in the following sections of the present disclosure.

BRIEF DESCRIPTION OF THE DRAWINGS

The invention can be more completely understood with reference to the following drawings.

FIG. 6A panels are images showing the distribution of hCDKL5 mRNA as detected by fluorescent RNAScope in CDKL5-deficient mice dosed via the intracerebroventricular route with rAAV9-CBA-hCDKL5 (left panel image of FIG. 6A) or rAAV9-SYN-hCDKL5 (right panel image of FIG. 6A).

FIG. 10A; hippocampus: FIG. 10B; and brainstem: FIG. 10C) of the CDKL5-deficient mouse brain using western blot approximately 3 months after dosing. Moderate long-lasting increases in human CDKL5 protein across the brain of treated mice (20-30% of WT levels in frontal cortex and brainstem, 35-70% in hippocampus) were observed 3 months after dosing.

FIGS. 11A-11D shows graphs demonstrating that rAAV9-SYN-hCDKL5 treated mice (SYN-hCDKL5) perform better on learning, memory, and motor function tasks compared to vehicle treated (CDD-PBS) control littermates. Improvements were seen in anxiety-like behavior (FIG. 11A), motor function (FIG. 11B), coordination (FIG. 11C), as well as normalization in learning and memory (FIG. 11D).

0002) of $7.76\times10^{13}$ vg of rAAV9-SYN-eGFP given in the Trendelenburg position. The graph illustrates that intracisternal magna delivery results in increased numbers of vector genomes in the NHP CNS in a variety of brain tissues, including the parietal lobe (10×), striatum (10×), and thalamus (8×). The data presented in this graph were collected as part of two independent studies.

Figure 13A:
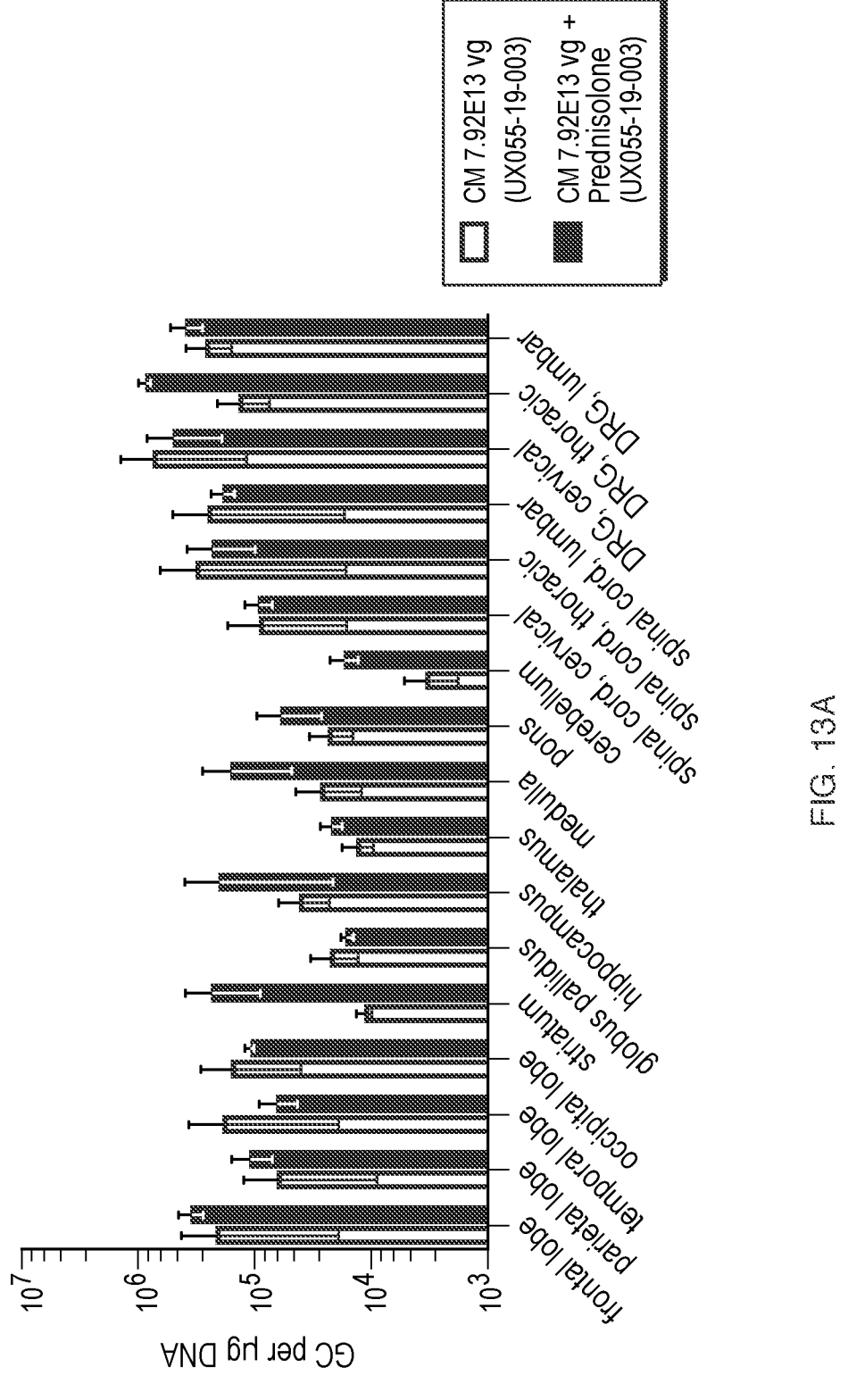
Figure 13B:
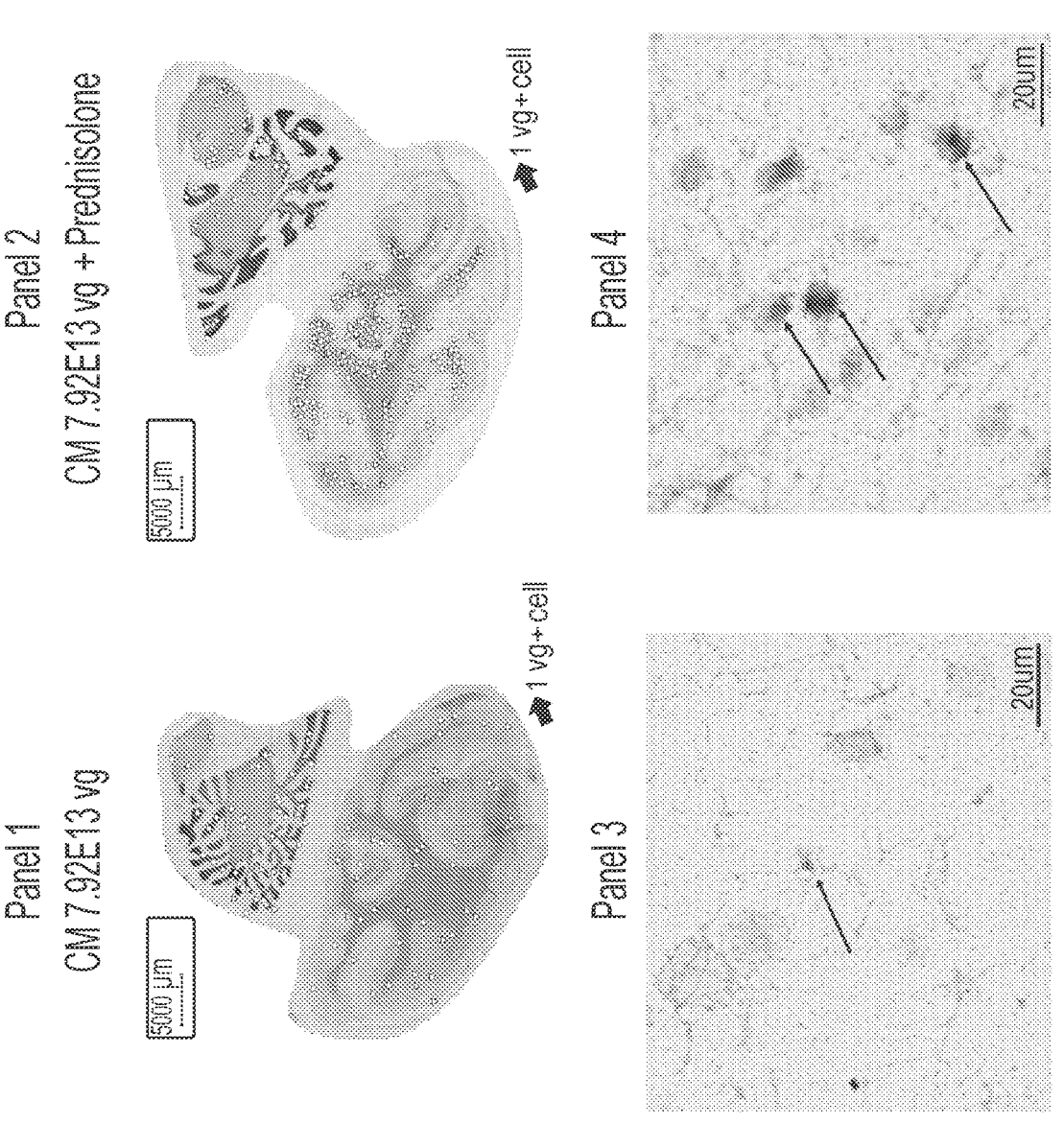
Figure 13C:
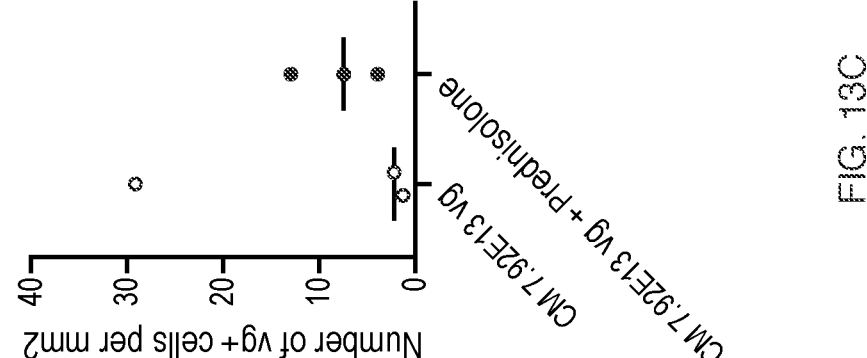

FIG. 13A is a bar graph illustrating genome copies (GC) per μg of DNA in the CNS of 1-year old female non-human primates (NHPs) four weeks after intracisterna magna (CM) delivery (UX055-19-003) of $7.92\times10^{13}$ vg of rAAV9-SYN-CDKL5 given in the Trendelenburg position with and without administration of 1 mg/kg prednisolone (by oral gavage) on days –4 to day 28. The graph illustrates that increased numbers of vector genomes (measured by qPCR) were present in a variety of brain tissues in NHPs administered prednisolone, including increases in the striatum (20×), hippocampus (5×), medulla (6×), and cerebellum (5×). FIG. 13B shows large sections of brain containing occipital cortex and cerebellum from the same NHPs that were examined using a BaseS cope analysis (in situ hybridization) with probes against the vector. Panels 1 and 3 represent sections from NHPs that were not administered prednisolone, while panels 2 and 4 represent sections from NHPs that were administered prednisolone. The number of cells with at least one vector genome were counted from one entire half coronal section for each NHP and an arrow was added to the image to mark each positive cell to aid visualization. FIG. 13C is a graph displaying number of cells containing at least one vector genome in NHPs treated with prednisolone compared to those without prednisolone. Overall, there was a trend toward an increase in the number of cells containing at least one vector genome in NHPs treated with prednisolone compared to those without prednisolone, however, there was significant animal to animal variability. One outlier NHP with very high numbers of vector genome positive cells was noted in the non prednisolone group.

DETAILED DESCRIPTION OF THE INVENTION

This invention provides a range of novel agents and compositions to be used for therapeutic applications. The nucleic acid sequences, vectors, recombinant viruses, and associated compositions of this invention can be used for ameliorating, preventing, or treating CDKL5 deficiency disorder (CDD) as described herein.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 12 recognized serotypes of AAV (AAV1-12).

Administration/Administer: To provide or give a subject an agent, such as a therapeutic agent (e.g., a recombinant AAV), by any effective route. Exemplary routes of administration include, but are not limited to, injection (such as subcutaneous, intramuscular, intradermal, intraperitoneal, intrathecal, intracerebroventricular, or intravenous administration), oral, intraductal, sublingual, rectal, transdermal, intranasal, vaginal and inhalation routes.

Coding Sequence: A "coding sequence" means the nucleotide sequence encoding a polypeptide in vitro or in vivo when operably linked to appropriate regulatory sequences. The coding sequence may or may not include regions preceding and following the coding region, e.g., 5' untranslated (5' UTR) and 3' untranslated (3' UTR) sequences, as well as intervening sequences (introns) between individual coding segments (exons).

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as CDD) refers to inhibiting the full development of a disease. "Treating" refers to a therapeutic intervention that ameliorates a sign or symptom of a disease or pathological condition (such as CDD) after it has begun to develop. "Ameliorating" refers to the reduction in the number or severity of signs or symptoms of a disease (such as CDD).

Promoter: A region of DNA that directs/initiates transcription of a nucleic acid (e.g., a gene). A promoter includes necessary nucleic acid sequences near the start site of transcription. Many promoter sequences are known to the person skilled in the art and even a combination of different promoter sequences in artificial nucleic acid molecules is possible. As used herein, a gene-specific endogenous promoter refers to a native promoter element that regulates expression of the endogenous gene of interest. In one embodiment, a CDKL5 gene-specific endogenous promoter regulates expression of a CDKL5 gene.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule such as a recombinant nucleic acid molecule encoding CDKL5 has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970: Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992: and Pearson et al., *Meth. Mol. Rio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stuffer sequence: Refers to a sequence of nucleotides contained within a larger nucleic acid molecule (such as a vector) that is typically used to create desired spacing between two nucleic acid features (such as between a promoter and a coding sequence), or to extend a nucleic acid molecule so that it is of a desired length. Stuffer sequences do not contain protein coding information and can be of unknown/synthetic origin and/or unrelated to other nucleic acid sequences within a larger nucleic acid molecule.

Subject: Living multi-cellular vertebrate organisms, a category that includes human and non-human mammals. In some embodiments, the subject is a human. In one embodiment, the human subject is an adult subject, i.e., a human subject greater than 18 years old. In one embodiment, the human subject is a pediatric subject, i.e., a human subject of ages 0-18 years old inclusive. In some embodiments, the subject (e.g., human subject) has been administered a corticosteroid. In some embodiments, the subject (e.g., human subject) has been administered an IgG-degrading protease. In some embodiments, the subject (e.g., human subject) has been administered a corticosteroid and has also been administered an IgG-degrading protease.

Synthetic: Produced by artificial means in a laboratory, for example a synthetic nucleic acid can be chemically synthesized in a laboratory.

Untranslated region (UTR): A typical mRNA contains a 5' untranslated region (5' UTR) and a 3' untranslated region (3' UTR) upstream and downstream, respectively, of the coding region (see Mignone F. et. al., (2002) *Genome Biol* 3:REVIEWS0004).

Therapeutically effective amount: A quantity of a specified pharmaceutical or therapeutic agent (e.g., a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Recombinant AAV (rAAV):

This invention provides compositions and methods of their use in gene therapy. More specifically, provided herein are recombinant adeno-associated virus (rAAV) comprising an adeno-associated virus (AAV) capsid, and a vector genome packaged therein useful for the treatment of CDD.

In one aspect, the present disclosure provides a recombinant adeno-associated virus (rAAV), wherein said rAAV comprises an AAV capsid and a vector genome packaged therein, wherein said vector genome comprises: (a) a promoter sequence; and (b) a partial or complete coding sequence for CDKL5 or an isoform thereof, or a functional fragment or functional variant thereof. In an exemplary embodiment, the coding sequence comprises a sequence which is at least 95% identical to a sequence selected from SEQ ID NOs: 1-8.

In some embodiments, the packaged vector genome may further comprise a 5'-ITR sequence, an enhancer, an intron, a consensus Kozak sequence, a polyadenylation signal, and/or a 3'-ITR sequence as described herein. In some embodiments, the recombinant vector can further include one or more stuffer nucleic acid sequences. In one embodiment, a stuffer nucleic acid sequence is situated between the intron and the partial or complete coding sequence for CDKL5.

In various embodiments described herein, the rAAV comprises an AAV capsid. The AAV capsid can be from an AAV of serotype 1, 2, 3, 4, 5, 6, 7, 8, 9, 10, 11, 12, rh10, hu37 (i.e., AAV1, AAV2, AAV3, AAV4, AAV5, AAV6, AAV7, AAV8, AAV9, AAV10, AAV11, AAV12, AAVrh10, AAVhu37), as well as any one of the more than 100 variants isolated from human and nonhuman primate tissues. See, e.g., Choi et al., 2005, *Curr Gene Ther.* 5: 299-310, 2005 and Gao et al., 2005, *Curr Gene Ther.* 5: 285-297.

Beyond the aforementioned capsids, also included within the scope of the invention are variant AAV capsids which have been engineered to harbor one or more beneficial therapeutic properties (e.g., improved targeting for select tissues, increased ability to evade the immune response, reduced stimulation of neutralizing antibodies, etc.). Non-limiting examples of such engineered variant capsids are described in U.S. Pat. Nos. 9,506,083, 9,585,971, 9,587,282, 9,611,302, 9,725,485, 9,856,539, 9,909,142, 9,920,097, 10,011,640, 10,081,659, 10,179,176, 10,202,657, 10,214,566, 10,214,785, 10,266,845, 10,294,281, 10,301,648, 10,385,320, and 10,392,632 and in PCT Publication NOs. WO/2017/165859, WO/2018/022905, WO/2018/156654, WO/2018/222503, and WO/2018/226602, the disclosures of which are herein incorporated by reference.

In certain exemplary embodiments, the rAAV administered according to the invention comprises an AAV9 capsid. The AAV9 capsid is a self-assembled AAV capsid composed of multiple AAV9 vp proteins. The AAV9 vp proteins are typically expressed as alternative splice variants encoded by a nucleic acid sequence of SEQ ID NO: 21 or a variant that is at least 70%, at least 75%, at least 80%, at least 85%, at least 90%, at least 95%, at least 97%, at least 99% identical thereto, which encodes the vp1 amino acid sequence of SEQ ID NO: 22 (GenBank Accession: AAS99264). These splice variants result in proteins of different length of SEQ ID NO: 22. As used herein, an AAV9 variant includes, e.g., those described in WO/2016/049230, U.S. Pat. No. 8,927,514, US Patent Publication No. 2015/0344911, and U.S. Pat. No. 8,734,809.

As indicated herein, the rAAV administered according to the invention may comprise, in some embodiments, an AAV9 capsid. However, in other embodiments, another AAV capsid is selected. Tissue specificity is determined by the capsid type. AAV serotypes which transduce a suitable target (e.g., liver, muscle, lung, or CNS) may be selected as sources for capsids of AAV viral vectors including, e.g., AAV1, AAV2, AAV3, AAV4, AAV5, AAV6, AAV6.2, AAV7, AAV8, AAV9, AAVrh10, AAVrh64R1, AAVrh64R2, AAVrh8. See, e.g., U.S. Patent Publication No. 2007/0036760; US Patent Publication No. 2009/0197338; and EP1310571. See also WO 2003/042397 (AAV7 and other simian AAV), U.S. Pat. Nos. 7,282,199 and 7,790,449 (AAV8). In addition, AAV yet to be discovered, or a recombinant AAV based thereon, may be used as a source for the AAV capsid. These documents also describe other AAV which may be selected for generating AAV and are incorporated by reference. In some embodiments, an AAV capsid for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the afore-mentioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned capsids.

Inverted Terminal Repeats (ITRs):

In some embodiments, the rAAV comprises a packaged vector genome which comprises an AAV ITR sequence, which functions as both the origin of vector DNA replication and the packaging signal of the vector genome, when AAV and adenovirus helper functions are provided in trans. Additionally, the ITRs serve as the target for single-stranded endonucleatic nicking by the large Rep proteins, resolving individual genomes from replication intermediates.

In some embodiments, the 5'-ITR sequence is from AAV2. In some embodiments, the 3'-ITR sequence is from AAV2. In some embodiments, the 5'-ITR sequence and the 3'-ITR sequence are from AAV2. In some embodiments, the 5'-ITR sequence and/or the 3'-ITR sequence are from AAV2 and comprise or consist of SEQ ID NO: 11. In other embodiments, the 5'-ITR sequence and/or the 3'-ITR sequence are from a non-AAV2 source.

Promoter:

In various aspects described herein, the rAAV comprises a packaged vector genome which comprises a promoter sequence that helps drive and regulate CDKL5 expression. In exemplary embodiments, the promoter sequence is located between a 5'-ITR sequence and the partial or complete coding sequence for CDKL5. In some embodiments, the promoter sequence is located downstream of an enhancer sequence. In some embodiments the promoter sequence is located upstream of an intron sequence.

In some embodiments, the promoter is a neuron-specific promoter. In one embodiment, the neuron-specific promoter is selected from a human synapsin 1 (SYN1) promoter, a mouse calcium/calmodulin-dependent protein kinase II (CaMKII) promoter, a rat tubulin alpha I (Ta1) promoter, a rat neuron-specific enolase (NSE) promoter, a human neuron-specific enolase (ENO2) promoter, a human platelet-derived growth factor-beta chain (PDGF) promoter, a human BM88 promoter, and a neuronal nicotinic receptor β2 (CHRNB2) promoter.

In an exemplary embodiment, the neuron-specific promoter is the SYN1 promoter (e.g., human SYN1 promoter). In one embodiment, the SYN1 promoter (e.g., human SYN1 promoter) is at least 80%, at least 85%, at least 90%, at least 91%, at least 92%, at least 93%, at least 94%, at least 95%, at least 96%, at least 97%, at least 98%, at least 99% or more identical to SEQ ID NO: 12. In an exemplary embodiment, the SYN1 promoter (e.g., human SYN1 promoter) comprises or consists of SEQ ID NO: 12.

In some embodiments, the promoter is selected from a chicken β-actin (CBA) promoter, a cytomegalovirus (CMV) immediate early gene promoter, a transthyretin (TTR) promoter, a thyroxine binding globulin (TBG) promoter, and an alpha-1 anti-trypsin (A1AT) promoter.

In an exemplary embodiment, the promoter is the CBA promoter. In one embodiment, the CBA promoter comprises or consists of SEQ ID NO: 13.

In some embodiments, the promoter is a gene-specific endogenous promoter. In one embodiment, the promoter comprises native gene promoter elements. In some illustrative embodiments, a packaged genome described herein comprises a CDKL5 gene-specific endogenous promoter comprising a nucleotide sequence of at least 15 continuous nucleotides, which is at least 95% identical to an equal length region of SEQ ID NO: 14. In certain embodiments, a packaged genome described herein comprises a CDKL5 gene-specific endogenous promoter comprising a nucleotide sequence of at least about 15 continuous nucleotides (for example, about 30, about 45, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 525, about 550, about 575, about 600, about 625, about 650, about 675, about 700, about 800, about 900, about 1000, about 1100, about 1200, about 1300, about 1400, or about 1500), which is at least 95% identical to an equal length region of SEQ ID NO: 14. In some illustrative embodiments, a packaged genome described herein comprises a CDKL5 gene-specific endogenous promoter comprising a nucleotide sequence of at least 15 continuous nucleotides, which is 100% identical to an equal length region of SEQ ID NO: 14.

Other Vector Elements:

In addition to a promoter and a coding sequence for CDKL5, a packaged genome may contain other appropriate transcription initiation, termination, enhancer sequence, and efficient RNA processing signals. As described in further detail below, such sequences include splicing and polyadenylation (poly A) signals, regulatory elements that enhance expression, sequences that stabilize cytoplasmic mRNA, sequences that enhance translation efficiency (i.e., the Kozak consensus sequence), and sequences that enhance protein stability.

In some embodiments, the rAAV contains a packaged vector genome that comprises one or more enhancer sequences. In one embodiment, the enhancer is selected from a cytomegalovirus immediate early gene (CMV) enhancer, a transthyretin enhancer (enTTR), a chicken β-actin (CBA) enhancer, an En34 enhancer, and an ApoE enhancer. In an exemplary embodiment, the enhancer is the CMV enhancer (e.g., CMV immediate early gene enhancer). In one embodiment, the CMV enhancer (e.g., CMV immediate early gene enhancer) comprises or consists of SEQ ID NO: 17.

In some embodiments, the rAAV contains a packaged vector genome that comprises one or more intron sequences. In one embodiment, the intron is selected from an SV40 Small T intron, a rabbit hemoglobin subunit beta (rHBB) intron, a human beta globin IVS2 intron, a (3-globin/IgG chimeric intron, and an hFIX intron. In one exemplary embodiment, the intron is the SV40 Small T intron. In one embodiment, the SV40 Small T intron sequence comprises or consists of SEQ ID NO: 18.

In some embodiments, the rAAV contains a packaged vector genome comprises a consensus Kozak sequence. In some embodiments, the consensus Kozak sequence is located downstream of an intron sequence. In one embodiment, the consensus Kozak sequence is GCCGCCACC (SEQ ID NO: 16).

In some embodiments, the rAAV contains a packaged vector genome that comprises a polyadenylation signal sequence. In one embodiment, the polyadenylation signal sequence is selected from a bovine growth hormone (BGH) polyadenylation signal sequence, an SV40 polyadenylation signal sequence, a rabbit beta globin polyadenylation signal sequence, and a CDKL5 gene-specific endogenous polyadenylation signal sequence. In an exemplary embodiment, the polyadenylation signal sequence is the SV40 polyadenylation signal sequence. In one embodiment, the SV40 polyadenylation signal sequence comprises or consists of SEQ ID NO: 15.

CDKL5 Polypeptides and Polynucleotides:

As described herein, aspects of the invention provide recombinant vectors that include a packaged genome that comprises a promoter sequence and a partial or complete coding sequence for CDKL5 or an isoform thereof, or a functional fragment or functional variant thereof.

In one embodiment, the partial or complete coding sequence for CDKL5 is a wild-type coding sequence. As used herein, the term "wild-type" refers to a biopolymer (e.g., a polypeptide sequence or polynucleotide sequence)

that is the same as the biopolymer (e.g., polypeptide sequence or polynucleotide sequence) that exists in nature.

In an alternative embodiment, the partial or complete coding sequence for CDKL5 is a codon-optimized coding sequence. In one embodiment, the partial or complete coding sequence for CDKL5 is codon-optimized for expression in humans.

In various embodiments described herein, vectors are provided that contain a packaged genome that comprise a coding sequence for CDKL5. The polypeptides delivered with the vectors described herein encompass CDKL5 polypeptides that may be useful in the treatment of mammals, including humans.

In some embodiments, the polypeptide expressed with a vector described herein is CDKL5 isoform 2 (SEQ ID NO: 9, GenBank Accession No. NP 001310218.1, 960 amino acids) or a functional fragment or functional variant thereof. In some embodiments, the polypeptide expressed with a vector described herein is CDKL5 isoform 2 and comprises or consists of SEQ ID NO: 9. In one embodiment, the CDKL5 isoform 2 polypeptide is encoded by the wild-type coding sequence shown in SEQ ID NO: 1. In alternative embodiments, the CDKL5 isoform 2 polypeptide is encoded by a codon-optimized coding sequence. In some embodiments, the CDKL5 isoform 2 polypeptide is encoded by a codon-optimized coding sequence that is less than 80% identical to the wild-type coding sequence shown in SEQ ID NO: 1. In some exemplary embodiments, the CDKL5 isoform 2 polypeptide is encoded by a codon-optimized coding sequence selected from SEQ ID NOs: 3-5. In some embodiments, the coding sequence for CDKL5 isoform 2 may further comprise a stop codon (TGA, TAA, or TAG) at the 3' end.

In some embodiments, the polypeptide expressed with a vector described herein is CDKL5 isoform 1 (SEQ ID NO: 10, GenBank Accession No. NP 001032420.1, 1030 amino acids) or a functional fragment or functional variant thereof. In some embodiments, the polypeptide expressed with a vector described herein is CDKL5 isoform 1 and comprises or consists of SEQ ID NO: 10. In one embodiment, the CDKL5 isoform 1 polypeptide is encoded by the wild-type coding sequence shown in SEQ ID NO: 2. In alternative embodiments, the CDKL5 isoform 1 polypeptide is encoded by a codon-optimized coding sequence. In some embodiments, the CDKL5 isoform 1 polypeptide is encoded by a codon-optimized coding sequence that is less than 80% identical to the wild-type coding sequence shown in SEQ ID NO: 2. In some exemplary embodiments, the CDKL5 isoform 1 polypeptide is encoded by a codon-optimized coding sequence selected from SEQ ID NOs: 6-8. In some embodiments, the coding sequence for CDKL5 isoform 1 may further comprise a stop codon (TGA, TAA, or TAG) at the 3' end.

In various aspects, the invention may be used to deliver fragments, variants, isoforms, or fusions of the CDKL5 polypeptides described herein.

In some embodiments, the invention may be used to deliver fragments of the CDKL5 polypeptides, which comprise at least 50, at least 100, at least 150, at least 200, at least 250, at least 300, at least 350, at least 400, at least 450, at least 500, at least 550, or at least 600 amino acid residues and retain one or more activities associated with the full-length polypeptide (e.g., kinase activity in the case of an CDKL5). Such fragments may be obtained by recombinant techniques that are routine and well-known in the art. Moreover, such fragments may be tested for activity by routine in vitro assays known to the skilled artisan. For instance, CDKL5 activity can be assayed by an in vitro autophosphorylation kinase assay as described in Lin et al., 2005, *Human Mol Genet* 14(24): 3775-86. Briefly, 500 µg of ectopically expressed FLAG-tagged CDKL5 can be incubated with 5 µg of M2 bound agarose for 4 h. Beads may be washed three times with TLB and twice with kinase buffer (25 m M HEPES, pH 7.4, 10 mM MgCl$_2$, 10 mM MnCl$_2$, 10 mM dithiothreitol, 0.2 mM sodium vanadate and 10 mM nitro-phenyl-phosphate). FLAG peptide can then be used to elute CDKL5. Resultant beads may then be resuspended in 30 µl of kinase buffer with addition of 100 µM ATP, 5 µCi of [γ-$^{32}$P]-ATP (NEN) and substrate. Kinase assays may be carried out 15 min at 30° C. and terminated by addition of SDS-PAGE protein loading buffer.

In some aspects, the present disclosure also provides nucleic acid molecules which encode the above-described polypeptide fragments.

In some embodiments, the invention may be used to deliver variants of the CDKL5 polypeptides. In some embodiments, the variant polypeptides may be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) identical to the wild-type therapeutic polypeptide, e.g., a wild-type CDKL5 isoform 2 polypeptide of SEQ ID NO: 9 or a wild-type CDKL5 isoform 1 polypeptide of SEQ ID NO: 10. In some embodiments, the variant therapeutic polypeptides may have at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least at least 24, at least 25, at least 26, at least 27, at least 28, at least 29, at least 30, at least 31, at least 32, at least 33, at least 34, at least 35, at least 36, at least 37, at least 38, at least 39, or at least 40 different residues as compared to the respective wild-type polypeptide. Such variants may be obtained by recombinant techniques that are routine and well-known in the art. Moreover, such variants may be tested for kinase activity by routine in vitro assays known to the skilled artisan. See, e.g., Lin et al., 2005, *Human Mol Genet* 14(24): 3775-86 for a description of CDKL5 kinase activity assays.

In some aspects, the present disclosure also provides nucleic acid molecules which encode the above described therapeutic polypeptide variants.

Novel Codon-Optimized Sequences:

In some aspects, the present disclosure provides novel codon-optimized nucleic acid sequences encoding CDKL5 isoform 2. In one embodiment, the codon-optimized nucleic acid sequence encoding CDKL5 isoform 2 is less than 80% identical to the wild-type coding sequence shown in SEQ ID NO: 1. In some embodiments, the codon-optimized nucleic acid sequence encoding CDKL5 isoform 2 is at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) identical to SEQ ID NOs: 3-5. In some embodiments, the codon-optimized nucleic acid sequence encoding CDKL5 isoform 2 is 100% identical to a sequence selected from SEQ ID NOs: 3-5. In some embodiments, the present disclosure provides nucleic acid sequences which are less than 80% identical to the wild-type coding sequence shown in SEQ ID NO: 1 and are at least 80%, at least 85%, at least 90%, at least 91%, at least 92%, at least 93%, at least 94%, at least 95%, at least 96%, at least 97%, at least 98%, at least 99% or more identical to SEQ ID NOs: 3-5. In exemplary embodiments, the present disclosure provides a nucleic acid sequence encoding CDKL5 isoform 2 selected from SEQ ID NOs: 3-5. Further provided are fragments of the nucleic acid sequences shown in SEQ ID NOs: 3-5 which encode a polypeptide having functional CDKL5 activity. In some embodiments, the nucleic acid sequence encoding CDKL5 isoform 2 may further comprise a stop codon (TGA, TAA, or TAG) at the 3' end.

In some aspects, the present disclosure provides novel codon-optimized nucleic acid sequences encoding CDKL5 isoform 1. In one embodiment, the codon-optimized nucleic acid sequence encoding CDKL5 isoform 1 is less than 80% identical to the wild-type coding sequence shown in SEQ ID NO: 2. In some embodiments, the codon-optimized nucleic acid sequence encoding CDKL5 isoform 1 is at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) identical to SEQ ID NOs: 6-8. In some embodiments, the codon-optimized nucleic acid sequence encoding CDKL5 isoform 1 is 100% identical to a sequence selected from SEQ ID NOs: 6-8. In some embodiments, the present disclosure provides nucleic acid sequences which are less than 80% identical to the wild-type coding sequence shown in SEQ ID NO: 2 and are at least 80%, at least 85%, at least 90%, at least 91%, at least 92%, at least 93%, at least 94%, at least 95%, at least 96%, at least 97%, at least 98%, at least 99% or more identical to a sequence selected from SEQ ID NOs: 6-8. In exemplary embodiments, the present disclosure provides a nucleic acid sequence encoding CDKL5 isoform 1 selected from SEQ ID NOs: 6-8. Further provided are fragments of the nucleic acid sequences shown in SEQ ID NOs: 6-8 which encode a polypeptide having functional CDKL5 activity. In some embodiments, the nucleic acid sequence encoding CDKL5 isoform 1 may further comprise a stop codon (TGA, TAA, or TAG) at the 3' end.

Host Cells Comprising a Recombinant Nucleic Acid Molecule:

In some aspects, provided herein are host cells comprising a recombinant nucleic acid molecule, viral vector, e.g., an AAV vector, or an rAAV disclosed herein. In specific embodiments, the host cells may be suitable for the propagation of AAV.

A vast range of host cells can be used, such as bacteria, yeast, insect, mammalian cells, etc. In some embodiments, the host cell can be a cell (or a cell line) appropriate for production of recombinant AAV (rAAV), for example, a HeLa, Cos-7, HEK293, A549, BHK, Vero, RD, HT-1080, ARPE-19, or MRC-5 cell.

The recombinant nucleic acid molecules or vectors can be delivered into the host cell culture using any suitable method known in the art. In some embodiments, a stable host cell line that has the recombinant nucleic acid molecule or vector inserted into its genome is generated. In some embodiments, a stable host cell line is generated, which contains an rAAV vector described herein. After transfection of the rAAV vector to the host culture, integration of the rAAV into the host genome can be assayed by various methods, such as antibiotic selection, fluorescence-activated cell sorting, southern blot, PCR based detection, fluorescence in situ hybridization as described by Nakai et al, Nature Genetics (2003) 34, 297-302; Philpott et al, Journal of Virology (2002) 76(11):5411-5421, and Howden et al, J Gene Med 2008; 10:42-50. Furthermore, a stable cell line can be established according to protocols well known in the art, such as those described in Clark, Kidney International Vol 61 (2002):59-S15, and Yuan et al, Human Gene Therapy 2011 May; 22(5): 613-24.

Recombinant AAV for Gene Therapy:

AAV belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORF). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Days and Berns, *Clin Microbiol Rev* 21(4):583-593, 2008).

The left ORF of AAV contains the Rep gene, which encodes four proteins—Rep78, Rep68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008).

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev,* 21(4):583-593, 2008).

Methods for producing rAAV suitable for gene therapy are well known in the art (see, for example, U.S. Patent Application NOs. 2012/0100606; 2012/0135515; 2011/0229971; and 2013/0072548; and Ghosh et al., *Gene Ther* 13(4):321-329, 2006), and can be utilized with the recombinant nucleic acid molecules and methods disclosed herein.

In some aspects, the present disclosure provides the use of an rAAV disclosed herein for the treatment of CDKL5 deficiency disorder (CDD), wherein the rAAV includes an AAV capsid and a vector genome packaged therein. In some embodiments, the rAAV contains a packaged genome comprising as operably linked components in 5' to 3' order: a 5'-ITR, a promoter sequence, a partial or complete coding sequence for CDKL5, or a functional fragment or functional variant thereof, and a 3'-ITR. In some embodiments, the coding sequence for CDKL5 is selected from SEQ ID NOs: 1-8, or a sequence at least 95% identical thereto.

In an exemplary embodiment, the coding sequence for CDKL5 comprises or consists of SEQ ID NO: 1. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 2. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 3. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 4. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 5. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 6. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 7. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

In an exemplary embodiment, the coding sequence for CDKL5 comprises or consists of SEQ ID NO: 8. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid. In some embodiments, the capsid is an AAV8 capsid. In some embodiments, the capsid is an AAV9 variant capsid. In some embodiments, the 5'-ITR sequence and/or the 3'-ITR sequence are from AAV2. In some embodiments, the 5'-ITR sequence and/or the 3'-ITR sequence comprise or consist of SEQ ID NO: 11.

Figure 1:
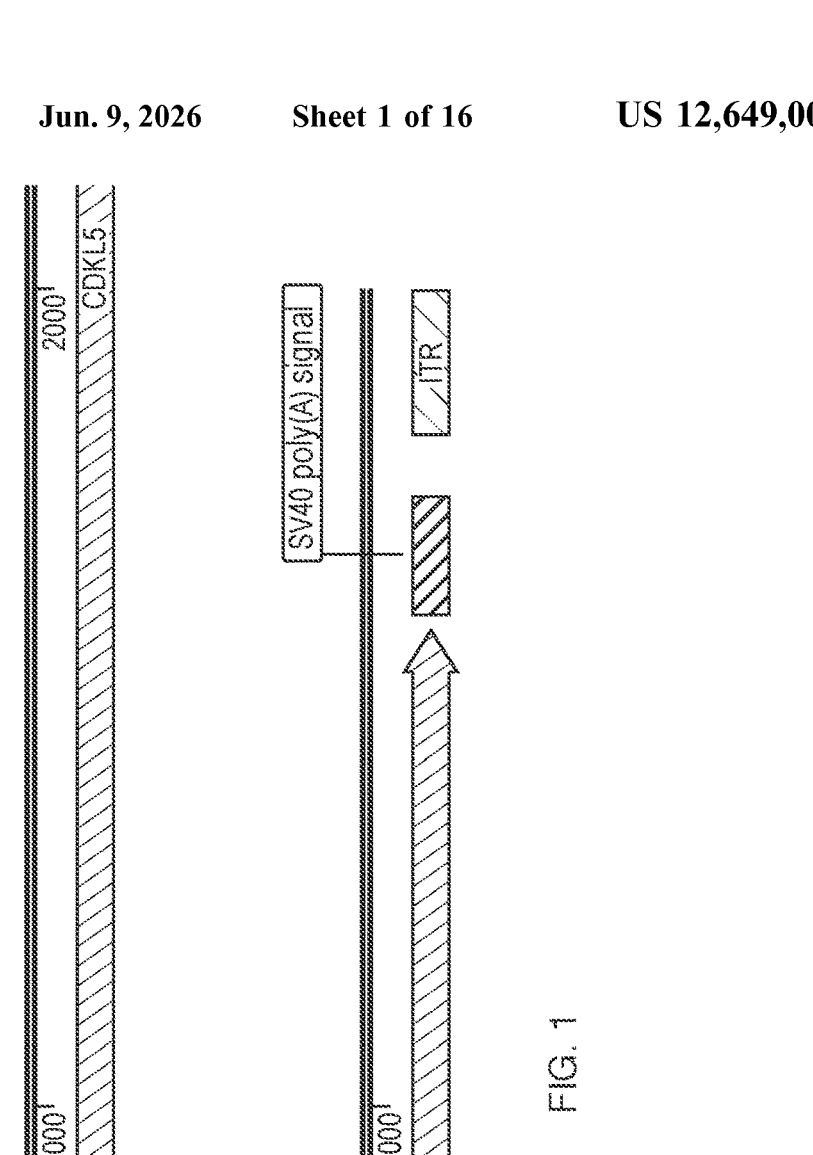
FIG. 1 is an illustrative diagram showing a first exemplary packaged vector genome construct comprising a coding sequence for CDKL5 under the control of a SYN promoter. Abbreviations used in the figure: ITR—inverted terminal repeat; hSyn—human Synapsin 1 promoter; SV40 poly(A) signal—SV40 polyadenylation signal.

An illustrative diagram showing an exemplary packaged vector genome construct for the expression of CDKL5 is provided in FIG. 1, which shows in 5' to 3' order: a 5'-ITR, a SYN1 promoter, a CDKL5 coding sequence, an SV40 polyadenylation signal sequence, and a 3'-ITR. The 3,828 bp sequence for this exemplary packaged vector genome construct is provided in SEQ ID NO: 19.

Figure 2:
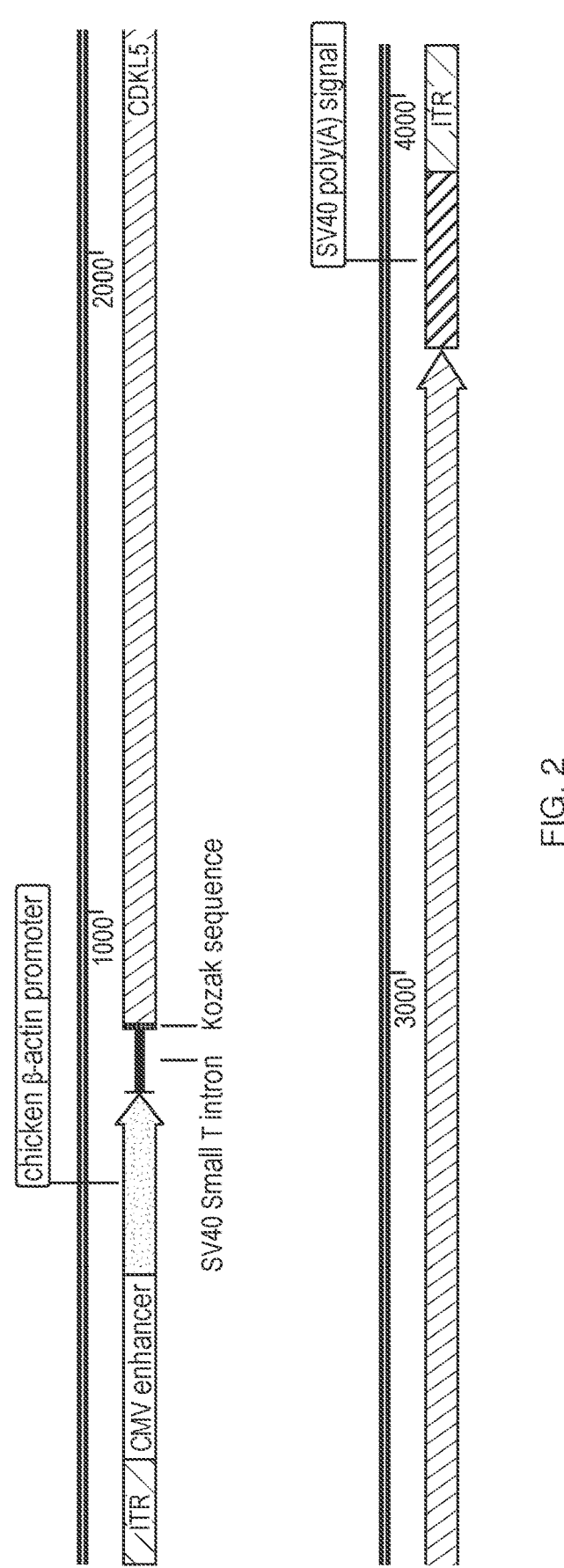
FIG. 2 is an illustrative diagram showing a second exemplary packaged vector genome construct comprising a coding sequence for CDKL5 under the control of a chicken β-actin (CBA) promoter. Abbreviations used in the figure: ITR—inverted terminal repeat; CMV-cytomegalovirus; SV40 poly(A) signal—SV40 polyadenylation signal.

Another illustrative diagram showing an exemplary packaged vector genome construct for the expression of CDKL5 is provided in FIG. 2, which shows in 5' to 3' order: a 5'-ITR, a CMV enhancer (e.g., CMV immediate early gene enhancer), a CBA promoter, an SV40 Small T intron, a CDKL5 coding sequence, an SV40 polyadenylation signal sequence, and a 3'-ITR. The 4,057 bp sequence for this exemplary packaged vector genome construct is provided in SEQ ID NO: 20.

Pharmaceutical Compositions:

In some aspects, the present disclosure provides a pharmaceutical composition that comprises an rAAV of the invention (e.g., an rAAV for the delivery of CDKL5) and a pharmaceutically acceptable carrier or excipient. In some embodiments, the pharmaceutical composition comprising an rAAV of the invention (e.g., an rAAV for the delivery of CDKL5) is formulated for subcutaneous, intramuscular, intradermal, intraperitoneal, intrathecal, intracerebroventricular, intravenous, or intracisterna magna administration. In an exemplary embodiment, the pharmaceutical composition is formulated for intrathecal administration. In another exemplary embodiment, the pharmaceutical composition is formulated for intracisterna magna administration.

In some embodiments, the rAAV is formulated in a buffer/carrier suitable for infusion in human subjects. The buffer/carrier should include a component that prevents the rAAV from sticking to the infusion tubing but does not interfere with the rAAV binding activity in vivo. Various suitable solutions may include one or more of: a buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene 10 (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol.

In an exemplary embodiment, the rAAV is formulated in a solution comprising NaCl (e.g., 200 mM NaCl), MgCl$_2$ (e.g., 1 mM MgCl$_2$), Tris (e.g., 20 mM Tris), pH 8.0, and poloxamer 188 (e.g., 0.005% or 0.01% poloxamer 188).

In some embodiments, the rAAV is formulated in a pharmaceutical composition comprising at least one dihydric or polyhydric alcohol. In one embodiment, the dihydric or polyhydric alcohol is one or more alcohols selected from the group consisting of polyethylene glycol, propylene glycol and sorbitol.

In an exemplary embodiment, the rAAV is formulated in a pharmaceutical composition comprising sorbitol. In one embodiment, sorbitol is present in the formulation at a range of 0.5 wt % to 20 wt %. In one embodiment, sorbitol is present in the formulation at a range of 1 wt % to 10 wt %. In one embodiment, sorbitol is present in the formulation at about 1 wt %, about 2 wt %, about 3 wt %, about 4 wt %, about 5 wt %, about 6 wt %, about 7 wt %, about 8 wt %, about 9 wt %, or about 10 wt %.

In an exemplary embodiment, the rAAV is formulated in a pharmaceutical composition comprising 5 wt % sorbitol and poloxamer 188 (e.g., 0.005% or 0.01% poloxamer 188).

Methods of Treating CDKL5 Deficiency Disorder (CDD):

In yet another aspect, the present disclosure provides methods of treating CDKL5 deficiency disorder (CDD) in a human subject comprising administering to the human subject a therapeutically effective amount of at least one rAAV disclosed herein.

In one embodiment, the present disclosure provides a method of treating CDD comprising administering an rAAV that includes an AAV capsid and a vector genome packaged therein, wherein the vector genome comprises a partial or complete coding sequence for CDKL5, or a functional fragment or functional variant thereof. In some embodiments, the coding sequence for CDKL5 is selected from SEQ ID NOs: 1-8, or a sequence at least 95% identical thereto. In an exemplary embodiment, the coding sequence for CDKL5 comprises or consists of SEQ ID NO: 1. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid.

In certain embodiments, the present disclosure provides methods of treating CDD in a human subject comprising administering to a human subject diagnosed with at least one mutation in CDKL5 a therapeutically effective amount of at least one rAAV disclosed herein. Non-limiting lists of pathogenic mutations in CDKL5 are described in Hector et al., 2017, *Neurol Genet* 3(6): e200, in Russo et al., 2009, *Neurogenetics* 10(3): 241-50, and at the Leiden Open Variation Database (LOVD) Global Variome for CDKL5.

In one embodiment, the present disclosure provides a method of treating CDD in a human subject diagnosed with at least one mutation in CDKL5 comprising administering an rAAV that includes an AAV capsid and a vector genome packaged therein, wherein the vector genome comprises a partial or complete coding sequence for CDKL5, or a functional fragment or functional variant thereof. In some embodiments, the coding sequence for CDKL5 is selected from SEQ ID NOs: 1-8, or a sequence at least 95% identical thereto. In an exemplary embodiment, the coding sequence for CDKL5 comprises or consists of SEQ ID NO: 1. In some embodiments, the promoter sequence is selected from SEQ ID NOs: 12-14. In an exemplary embodiment, the promoter sequence comprises or consists of SEQ ID NO: 12. In some embodiments, the capsid is an AAV9 capsid.

Any suitable method or route can be used to administer an rAAV or an rAAV-containing composition described herein. Routes of administration include, for example, subcutaneously, intradermally, intraperitoneally, intrathecally, intracerebroventricularly, intravenously, intracisterna magna, and other parenteral routes of administration. In an exemplary embodiment, the rAAV is administered intrathecally. In another exemplary embodiment, the rAAV is administered via the cisterna magna.

In one embodiment, the rAAV can be administered via a cisternal intrathecal route. In another embodiment, the rAAV can be administered via a lumbar intrathecal route. In some embodiments, the rAAV can be administered using an auto-intrathecal injector. For instance, an injector that leverages CSF dynamics, physiological pulsatility, and volume displacement can be utilized to deliver rAAV intrathecally. An example of one possible injector for use in the methods of the invention is the Pulsar™ Smart Intrathecal Delivery Platform in development at Alcyone Lifesciences, Inc.

The specific dose administered can be a uniform dose for each patient, for example, $1.0 \times 10^{11}$-$1.0 \times 10^{14}$ genome copies (GC) of virus per patient. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can also be adjusted as the progress of the disease is monitored In some embodiments, the rAAV is administered at a dose of, e.g., about $1.0 \times 10^{11}$ genome copies per kilogram of patient body weight (GC/kg) to about $1 \times 10^{14}$ GC/kg, about $5 \times 10^{11}$ genome copies per kilogram of patient body weight (GC/kg) to about $5 \times 10^{11}$ GC/kg, or about $1 \times 10^{12}$ to about $1 \times 10^{11}$ GC/kg, as measured by qPCR or digital droplet PCR (ddPCR). In some embodiments, the rAAV is administered at a dose of about $1 \times 10^{12}$ to about $1 \times 10^{13}$ genome copies (GC)/kg. In some embodiments, the rAAV is administered at a dose of about $1.1 \times 10^{11}$, about $1.3 \times 10^{11}$, about $1.6 \times 10^{11}$, about $1.9 \times 10^{11}$, about $2 \times 10^{11}$, about $2.5 \times 10^{11}$, about $3.0 \times 10^{11}$, about $3.5 \times 10^{11}$, about $4.0 \times 10^{11}$, about $4.5 \times 10^{11}$, about $5.0 \times 10^{11}$, about $5.5 \times 10^{11}$, about $6.0 \times 10^{11}$, about $6.5 \times 10^{11}$, about $7.0 \times 10^{11}$, about $7.5 \times 10^{11}$, about $8.0 \times 10^{11}$, about $8.5 \times 10^{11}$, about $9.0 \times 10^{11}$, about $9.5 \times 10^{11}$, about $1.0 \times 10^{12}$, about $1.5 \times 10^{12}$, about $2.0 \times 10^{12}$, about $2.5 \times 10^{12}$, about $3.0 \times 10^{12}$, about $3.5 \times 10^{12}$, about $4.0 \times 10^{12}$, about $4.5 \times 10^{12}$, about $5.0 \times 10^{12}$, about $5.5 \times 10^{12}$, about $6.0 \times 10^{12}$, about $6.5 \times 10^{12}$, about $7.0 \times 10^{12}$, about $7.5 \times 10^{12}$, about $8.0 \times 10^{12}$, about $8.5 \times 10^{12}$, about $9.0 \times 10^{12}$, about $9.5 \times 10^{12}$, about $1.0 \times 10^{13}$, about $1.5 \times 10^{13}$, about $2.0 \times 10^{13}$, about $2.5 \times 10^{13}$, about $3.0 \times 10^{13}$, about $3.5 \times 10^{13}$, about $4.0 \times 10^{13}$, about $4.5 \times 10^{13}$, about $5.0 \times 10^{13}$, about $5.5 \times 10^{13}$, about $6.0 \times 10^{13}$, about $6.5 \times 10^{13}$, about $7.0 \times 10^{13}$, about $7.5 \times 10^{13}$, about $8.0 \times 10^{13}$, about $8.5 \times 10^{13}$, about $9.0 \times 10^{13}$, about $9.5 \times 10^{13}$ genome copies (GC)/kg. The rAAV can be administered in a single dose, or in multiple doses (such as 2, 3, 4, 5, 6, 7, 8, 9, 10 or more doses) as needed for the desired therapeutic results.

In some embodiments, the methods of treating CDD according to the instant invention may further comprise administration of an IgG-degrading protease prior to administration of an rAAV described herein. Accordingly, the present disclosure provides a method of treating CDD comprising first administering an IgG-degrading protease and then subsequently administering an rAAV that includes an AAV capsid and a vector genome packaged therein, wherein the vector genome comprises a partial or complete coding sequence for CDKL5, or a functional fragment or functional variant thereof.

In some embodiments, the methods of treating CDD according to the instant invention is performed on a human subject who has been administered an IgG-degrading protease.

Examples of proteases that may be used in the instant invention include, for example and without limitation, those described in WO/2020/016318 and/or WO/2020/159970, including, for example, cysteine proteases from *Streptococcus pyogenes, Streptococcus equi, Mycoplasma canis, Streptococcus agalactiae, Streptococcus pseudoporcinus*, or *Pseudomonas putida*.

In certain embodiments, the IgG-degrading protease is the IdeS from *Streptococcus pyogenes* (SEQ ID NO: 23) or a protease which is at least 80%, at least 85%, at least 90%, at least 95%, at least 96%, at least 97%, at least 98%, or at least 99% identical to SEQ ID NO: 23. In some embodiments, the protease is an engineered variant of SEQ ID NO: 23. Examples of engineered IdeS proteases are described in WO/2020/016318 and U.S. Patent Publication NOs. 20180023070 and 20180037962. In some embodiments, the engineered IdeS variant may have 1, 2, 3, 4, 5, or more amino acid modifications relative to SEQ ID NO: 20.

In certain embodiments, the IgG-degrading protease is the IdeZ from *Streptococcus equi* (SEQ ID NO: 24) or a protease which is at least 80%, at least 85%, at least 90%, at least 95%, at least 96%, at least 97%, at least 98%, or at least 99% identical to SEQ ID NO: 24. In some embodiments, the protease is an engineered variant of SEQ ID NO: 24. Examples of engineered IdeZ proteases are described in WO/2020/016318. In some embodiments, the engineered IdeZ variant may have 1, 2, 3, 4, 5, or more amino acid modifications relative to SEQ ID NO: 21.

Other proteases that may be used in the instant invention include, for example and without limitation, IgdE enzymes from *Streptococcus suis, Streptococcus porcinus*, and *Streptococcus equi*, described in WO/2017/134274.

In some embodiments, the IgG-degrading protease may be encapsulated in or complexed with liposomes, nanoparticles, lipid nanoparticles (LNPs), polymers, microparticles, microcapsules, micelles, or extracellular vesicles.

Methods of Treating CNS Disorders Comprising Use of Corticosteroids:

The present inventors have surprisingly observed that administration of the corticosteroid, prednisolone, prior to rAAV administration leads to increases in the number of vector genomes present in a variety of brain tissues. Without being bound by theory, it is hypothesized that the corticosteroid acts to reduce inflammation in CNS tissues, which allows the rAAV to penetrate into deep CNS tissues which would otherwise be inaccessible in the absence of corticosteroid administration. Accordingly, in yet another aspect, the present disclosure provides a method of treating a CNS disorder in a human subject comprising first administering to the subject a corticosteroid and then subsequently administering a therapeutically effective amount of at least one rAAV designed for treatment of said CNS disorder, wherein the rAAV is administered intrathecally, intracerebroventricularly, or via intracisterna magna delivery. Also provided is a method of treating a CNS disorder in a human subject comprising administering a therapeutically effective amount of at least one rAAV designed for treatment of said CNS disorder, wherein the subject has been administered a corticosteroid; optionally, the rAAV is administered intrathecally, intracerebroventricularly, or via intracisterna magna delivery.

In various embodiments according to this aspect, the corticosteroid may be selected from prednisolone, prednisone, dexamethasone, hydrocortisone, triamcinolone, methylprednisolone, budesonide, betamethasone, and deflazacort. In an exemplary embodiment, the corticosteroid is prednisolone.

In various embodiments according to this aspect, the corticosteroid is administered to the subject at least about 12 hours before administration of the rAAV. In another embodiment, the corticosteroid is administered to the subject at least about 24 hours before administration of the rAAV. In yet another embodiment, the corticosteroid is administered to the subject at least about 2 days before administration of the rAAV. In yet another embodiment, the corticosteroid is administered to the subject at least about 3, 4, 5, 6, 7, or more days before administration of the rAAV. In yet another embodiment, the corticosteroid is administered to the subject at least about 7, 14, 21, or more days before administration of the rAAV. In yet another embodiment, the corticosteroid is administered to the subject at least about 1 month, at least about 2 months, or at least about 3 months before administration of the rAAV.

In one embodiment, the corticosteroid is administered once before administration of the rAAV. In another embodiment, the corticosteroid is administered twice before administration of the rAAV. In yet another embodiment, the corticosteroid is administered 3, 4, 5, or more times before administration of the rAAV.

Administration of the corticosteroid to a human subject can be by any route, including but not limited to oral, intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intrapleural, intracerebral, intra-arterial, intraperitoneal, or intranasal administration. In an exemplary embodiment, the corticosteroid is administered orally.

In certain embodiments, the dose of a corticosteroid is measured in units of mg/kg of subject body weight. In other embodiments, the dose of a corticosteroid is measured in units of mg per dose administered to a subject. Any measurement of dose can be used in conjunction with compositions and methods of the invention and dosage units can be converted by means standard in the art.

In certain embodiments, the corticosteroid may be administered at a dose of about 1 mg to about 1000 mg. In some embodiments, the corticosteroid is administered at a dose of about 3 mg to about 300 mg. In some embodiments, the corticosteroid is administered at a dose of about 5 mg to about 150 mg. In some embodiments, the corticosteroid is administered at a dose of about 10 mg to about 100 mg. In some embodiments, the corticosteroid is administered at a dose of about 15 mg to about 80 mg. In some embodiments, the corticosteroid is administered at a dose of about 20 mg to about 60 mg.

In certain embodiments the corticosteroid may be administered at a dose of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg, or about 1000 mg.

In certain embodiments, the corticosteroid may be administered at a dose of about 0.1 mg/kg to about 100 mg/kg of body weight of a subject. In some embodiments, the anti-CD19 antibody is administered at a dose of about 0.2 mg/kg to about 10 mg/kg. In some embodiments, the anti-CD19 antibody is administered at a dose of about 0.5 mg/kg to about 5 mg/kg. In some embodiments, the anti-CD19 antibody is administered at a dose of about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 2 mg/kg, about 3 mg/kg, about 4 mg/kg, about 5 mg/kg, or about 10 mg/kg of body weight of a subject.

In some embodiments, the corticosteroid may be administered for a total of at least 1, at least 2, at least 3, at least 4, at least 5, at least 6, at least 7, at least 8, at least 9, at least 10, or more days prior to administration of the rAAV. For example, in certain exemplary embodiments, the corticosteroid may be administered at 1 mg/kg per day for 5 days prior to administration of the rAAV.

In some embodiments, the corticosteroid may be administered at 1 mg/kg per day for 4 weeks with a first dose occurring 5 days prior to administration of the rAAV. In some embodiments, the corticosteroid may be administered at 1 mg/kg per day for 4 weeks with a first dose occurring 5 days prior to administration of the rAAV, followed by a taper of corticosteroid for an additional 4 weeks.

The methods according to this aspect may be used to treat any CNS disorder for which gene therapy may be suitable. In some embodiments, the CNS disorder is selected from CDD, Angelman syndrome, Batten disease, Krabbe disease, Parkinson's disease, Alzheimer's disease, Spinal Muscular Atrophy (SMA) Types I, II, III, and IV, X-linked Myotubular Myopathy, Friedrich's Ataxia, Canavan's, Amyotrophic Lateral Sclerosis (ALS), Adrenoleukodystrophy, Huntington disease, Rett syndrome, and Spinocerebellar ataxia. In an exemplary embodiment, the CNS disorder is CDD. In another exemplary embodiment, the rAAV for use in a method according to this aspect comprises an rAAV useful for the treatment of CDD described herein. For instance, rAAV may comprise an AAV capsid (e.g., an AAV9 capsid) and a vector genome packaged therein, wherein said vector genome comprises: (a) a promoter sequence (e.g., a SYN1 promoter sequence, e.g., a human SYN1 promoter sequence); and (b) a partial or complete coding sequence for CDKL5 or an isoform thereof, or a functional fragment or functional variant thereof. In some embodiments, the coding sequence comprises a sequence which is at least 95% identical to a sequence selected from SEQ ID NOs: 1-8.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the present disclosure, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within the present disclosure, embodiments have been described and depicted in a way that enables a clear and concise disclosure to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including" is intended merely to illustrate better the present invention and does not pose a limitation on the scope of the invention unless claimed. No language in the specification should be construed as indicating any non-claimed element as essential to the practice of the present invention.

EXAMPLES

The disclosure now being generally described, will be more readily understood by reference to the following examples, which are included merely for purposes of illustration of certain aspects and embodiments of the present disclosure, and are not intended to limit the scope of the disclosure in any way.

Example 1

The purpose of this example is to demonstrate that delivering CBA-hCDKL5 plasmid to Neuro2a (mouse neuroblastoma) cells leads to increased expression of CDKL5 and subsequent increased phosphorylation of EB2 (microtubule-associated protein RP/EB family member 2), a downstream target of CDKL5.

In this example, Neuro2a cells were transiently transfected with a plasmid containing the CBA promoter upstream of human CDKL5 cDNA for 48 hr or left untransfected. Cells were fixed and immunocytochemistry performed using anti-CDKL5 antibody and anti-Phospho-EB2 antibody. Imaging was performed using a Zeiss Axio Imager M2 fluorescent microscope.

Figure 3:
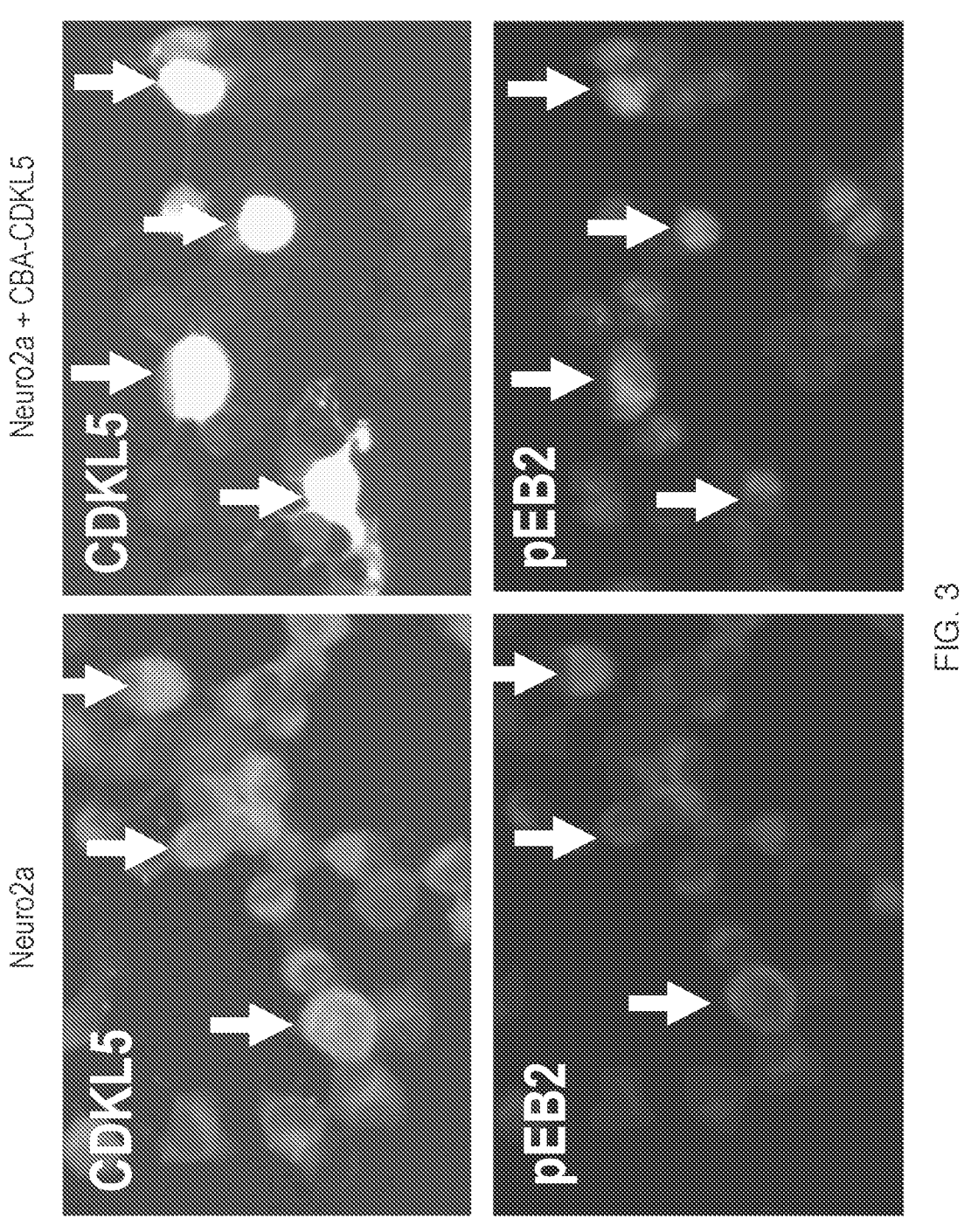
FIG. 3 are images showing changes in phospho-EB2 (pEB2) levels when human CDKL5 is overexpressed following transfection of Neuro2a cells with plasmid DNA. EB2, a downstream target of CDKL5, shows increased phosphorylation when human CDKL5 is overexpressed in these cells. The left two panels represent untreated cells. The right two panels represent cells transfected with human CDKL5 under the control of a CBA promoter.

As shown in FIG. 3, Neuro2a cells expressing high levels of hCDKL5 demonstrate enhanced levels of phosphorylated EB2 protein, a downstream target of CDKL5. This indicates that delivery of CDKL5 to Neuro2a cells can positively impact the activity of CDKL5 targets such as EB2.

Example 2

The purpose of this example is to demonstrate the expression of enhanced green fluorescent protein (eGFP) in various CNS tissues of rAAV9-CBA-eGFP or rAAV9-SYN-eGFP-treated Cdkl5 KO mice.

In this example, CDKL5-deficient mice were dosed with (1) rAAV comprising an AAV9 capsid and a vector genome comprising a CBA promoter and a eGFP coding sequence [rAAV9-CBA-eGFP] or (2) an rAAV comprising an AAV9 capsid and a vector genome comprising a SYN promoter and a eGFP coding sequence [rAAV9-SYN-eGFP]. Mice were administered rAAV by intracerebroventricular (ICV) injection. Tissue was retrieved at 2-4 weeks post-dosing for analysis. Brains were fixed, sliced, and immunostained for detection of eGFP.

Figure 4:
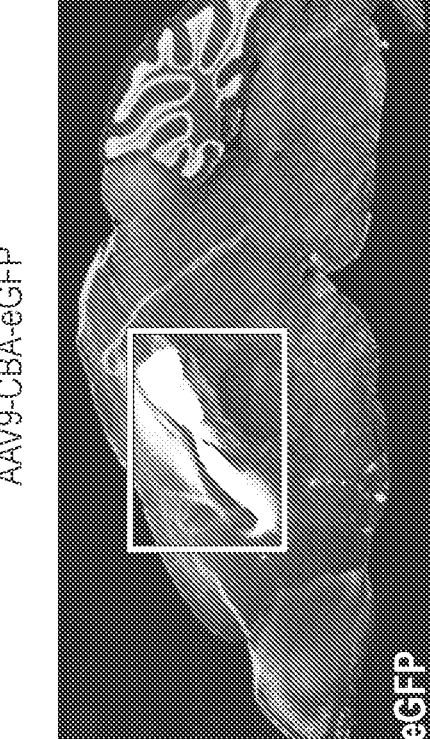
FIG. 4 is an image showing the distribution of enhanced green fluorescent protein (eGFP) in CDKL5-deficient mice dosed intracerebroventricularly with rAAV9-CBA-eGFP (left panel) or rAAV9-SYN-eGFP (right panel). Both vectors yielded high eGFP levels in the hippocampal and striatal regions and lower numbers of eGFP-positive cells in the cortex and cerebellum.

As shown in FIG. 4, eGFP was detected in multiple areas of the brain of dosed mice including the hippocampus, striatum, frontal cortex, and cerebellum. All mice had the highest concentration of eGFP in the hippocampus and striatum. Mice dosed with rAAV9-CBA-eGFP had few cells in the cortex and slightly more cells in the cerebellum; mice dosed with rAAV9-SYN-eGFP had fewer cells in the cerebellum and slightly more cells in the cortex.

This example demonstrates that administration of rAAV9-CBA-eGFP and rAAV9-SYN-eGFP by ICV injection yields high levels of eGFP protein in cells of the hippocampus and striatum and lower levels in cells of the cortex and cerebellum.

Example 3

The purpose of this example is to demonstrate that a human synapsin (SYN) promoter, a constitutive promoter (CBA), or an endogenous CDKL5 promoter can all drive CDKL5 protein expression in Neuro2a cells.

In this example, Neuro2a cells were transiently transfected with plasmids expressing eGFP or hCDKL5 for 48 hr. Neuro2a cells that were not transduced served as controls. Cells were fixed and immunocytochemistry performed using an anti-CDKL5 antibody. Imaging was performed using a Zeiss Axio Imager M2 fluorescent microscope.

Figure 5:
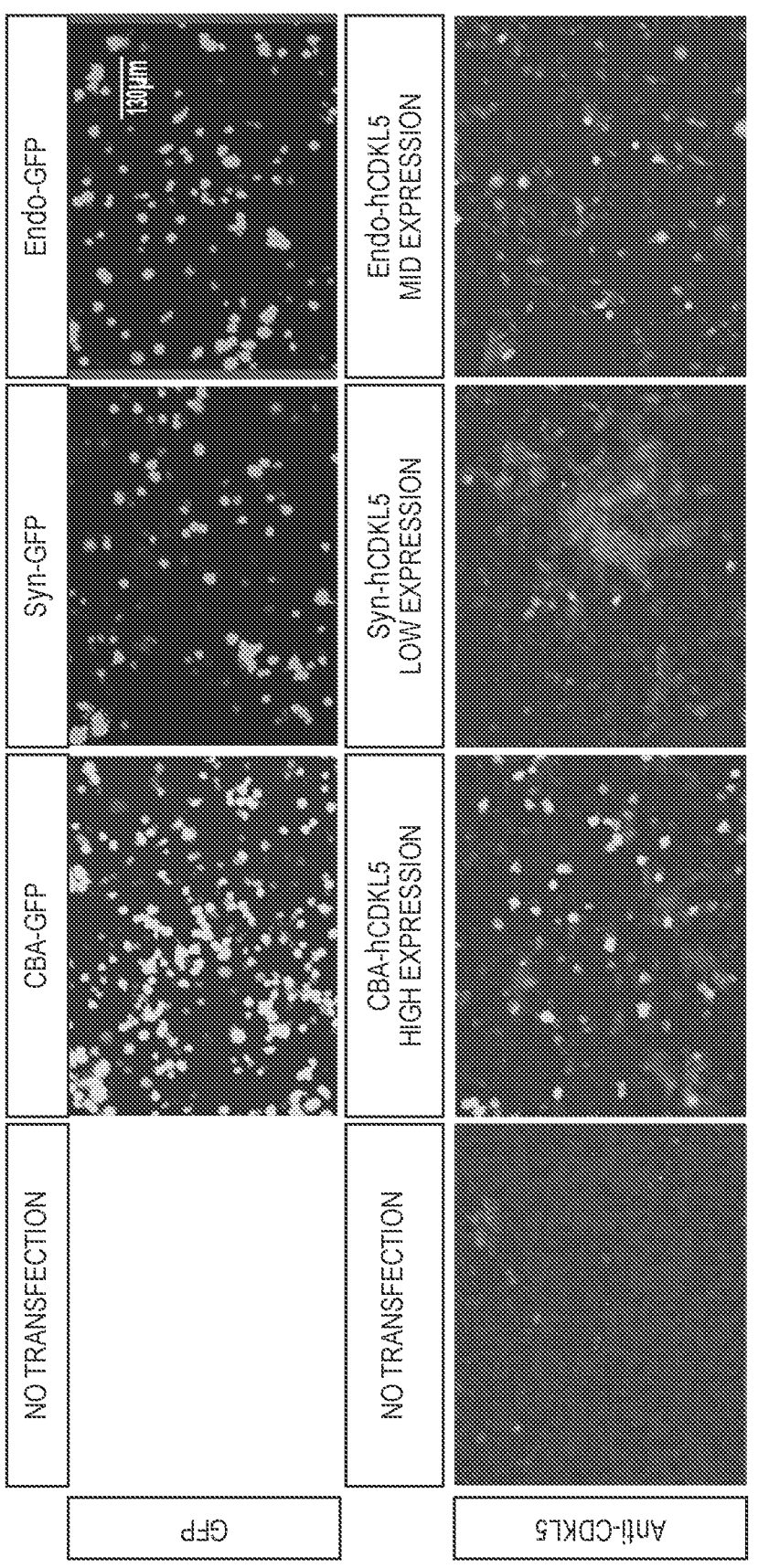
FIG. 5 is an image showing the expression of green fluorescent protein (GFP) and hCDKL5 plasmids in Neuro2a cells using the endogenous CDKL5 promoter alongside the CBA and SYN promoters. The endogenous CDKL5 promoter drives the expression of hCDKL5 at a level intermediate to the CBA and SYN promoters in these cells. The images are shown as follows from left to right (top four panels): untransfected, transfected with CBA-GFP, transfected with SYN-GFP, and transfected with endogenous CDKL5 promoter and eGFP (Endo-eGFP). Regarding the bottom four panels, the images are shown as follows from left to right: untransfected, transfected with CBAhCDKL5, transfected with SYN-hCDKL5, and transfected with endogenous CDKL5 promoter and hCDKL5 (Endo-hCDKL5).

As shown in FIG. 5, hCDKL5 and eGFP are expressed at intermediate levels in transfected Neuro2a cells using an endogenous CDKL5 promoter (Endo-hCDKL5 and Endo-eGFP, respectively) as compared to the highest expression levels with the CBA promoter and lower expression levels from the SYN promoter. This example indicates that the nucleotides lying upstream of the human CDKL5 transcriptional start site (i.e., the endogenous CDKL5 promoter) are capable of driving expression of eGFP as well as hCDKL5 in Neuro2a cells.

Example 4

The purpose of this example is to demonstrate that CSF delivery of rAAV9-SYN-hCDKL5 and rAAV9-CBA-hCDKL5 to CDKL5-deficient mice results in robust distribution of hCDKL5 mRNA and cDNA throughout the brain.

In this example, CDKL5-deficient mice were dosed with (1) rAAV comprising an AAV9 capsid and a vector genome comprising a CBA promoter and an hCDKL5 coding sequence [rAAV9-CBA-hCDKL5] or (2) an rAAV comprising an AAV9 capsid and a vector genome comprising a SYN promoter and an hCDKL5 coding sequence [rAAV9-SYN-hCDKL5]. Mice were dosed by intracerebroventricular (ICV) injection. Tissue was retrieved at either 2 weeks or 3 months post-dosing. Brains were fixed, sliced, and processed by RNAScope in situ hybridization to detect hCDKL5 mRNA and cDNA as well as Rbfox3 mRNA (neuronal marker).

Figure 6B:
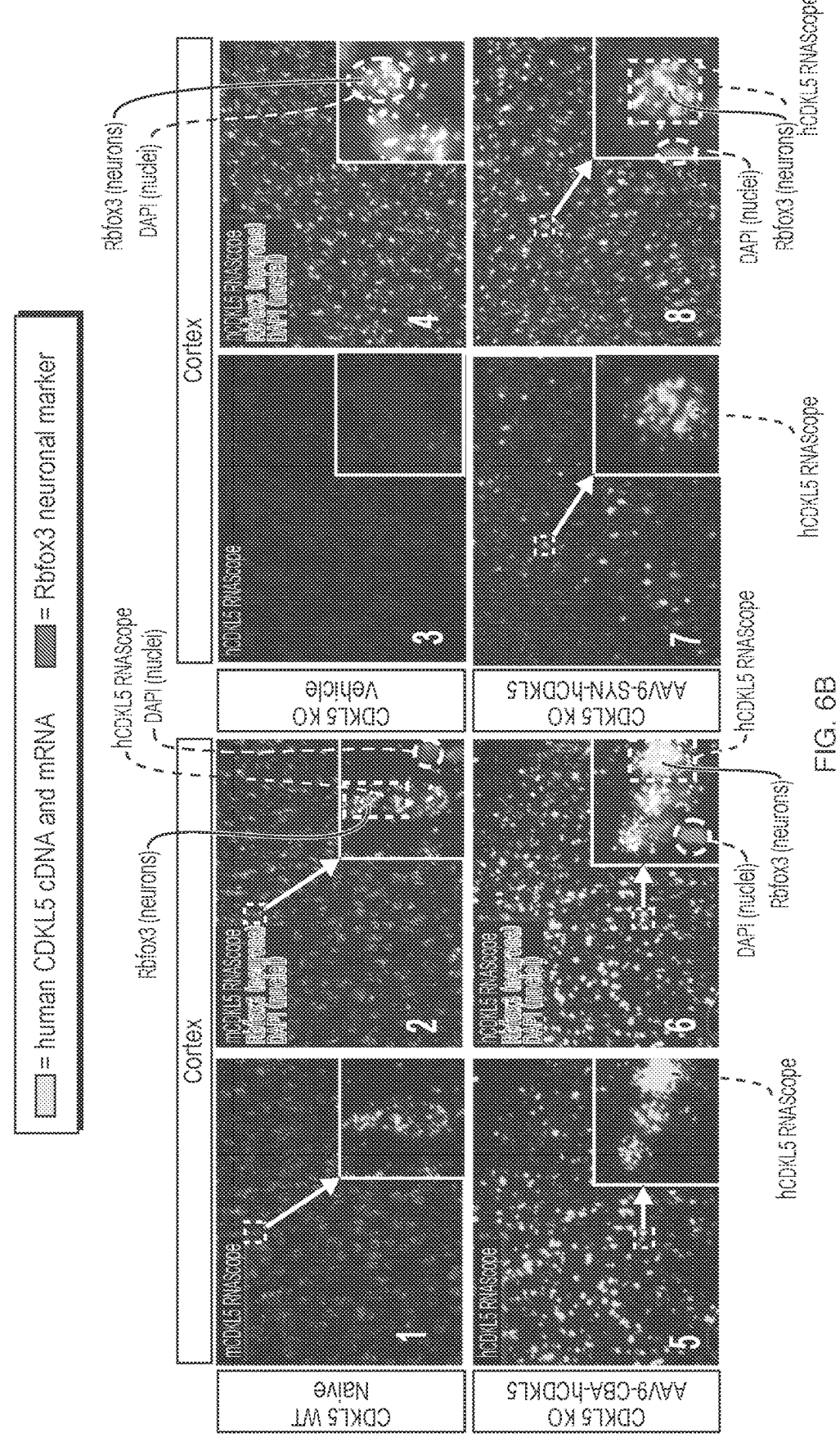
FIG. 6B panels are representative images from RNA-Scope in situ hybridization showing the distribution of hCDKL5 mRNA as detected by fluorescent RNAScope in CDKL5-deficient mice dosed via the intracerebroventricular route with rAAV9-CBA-hCDKL5 (squares 5 and 6) or rAAV9-SYN-hCDKL5 (squares 7 and 8). CDKL5 knockout (KO) mice dosed via the intracerebroventricular route with the vehicle are shown in squares 3 and 4. CDKL5 wild-type (WT) mice that were not dosed with any vehicle or either vector (naïve) are shown in squares 1 and 2.

As shown in FIG. 6A, both vectors yielded high levels of hCDKL5 in the hippocampal and striatal regions. Co-labeling confirmed that both vectors also expressed hCDKL5 in neurons throughout the cortex (FIG. 6B). As shown in FIG. 6B, mice treated with rAAV9-CBA-hCDKL5 (square 5 of FIG. 6B) or rAAV9-SYN-hCDKL5 (square 7 of FIG. 6B) by ICV injection had hCDKL5 mRNA and cDNA in the hippocampus, striatum, and cortex. Similarities in the overall distribution were noted between the two vectors and both vectors drove expression in neurons as shown by FIG. 6B which shows co-labeling with the neuronal marker Rbfox3. Square 6 of FIG. 6B shows co-labeling of hCDKL5 expressed from rAAV9-CBA-hCDKL5 vector and neuronal marker Rbfox3. Square 8 of FIG. 6B shows co-labeling of hCDKL5 expressed from rAAV9-SYN-hCDKL5 vector and neuronal marker Rbfox3.

The data shown in this example indicate that administration of rAAV9-CBA-hCDKL5 and rAAV9-SYN-hCDKL5 vectors by ICV injection leads to hCDKL5 mRNA and cDNA in neurons throughout the hippocampus, striatum, and frontal cortex.

Example 5

The purpose of this example is to demonstrate that AAV9-SYN-hCDKL5 and AAV9-CBA-hCDKL5 rAAV can deliver functional CDKL5 protein to the mouse brain.

In this example, CDKL5-deficient mice were dosed with rAAV9-CBA-hCDKL5 or rAAV9-SYN-hCDKL5 by intracerebroventricular (ICV) injection and tissue retrieved at 2 weeks post-dosing. Brains were microdissected and frontal cortex was homogenized and run on a western blot that was probed with antibodies against CDKL5, pEB2 and β-tubulin.

Figure 7:
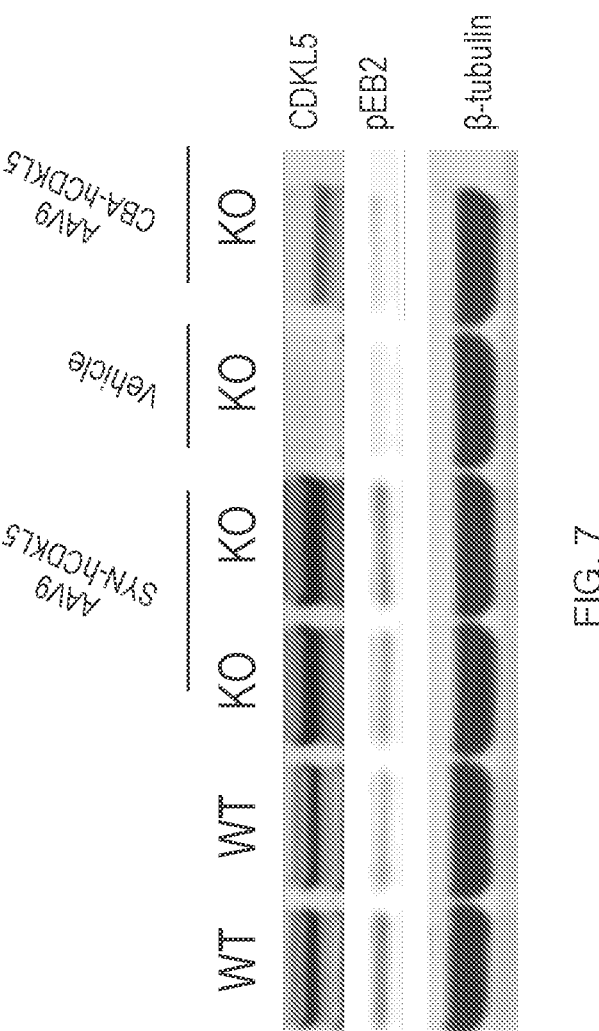
FIG. 7 is a western blot showing levels of CDKL5 protein and phosphorylated EB2 (pEB2) isolated from the frontal cortex of Cdkl5 knockout mice 2 weeks after they were dosed with a single intracerebroventricular injection of rAAV9-SYN-hCDKL5 or rAAV9-CBA-hCDKL5 (1.6e12 vector genomes (vg)). Treated mice show increased levels of CDKL5 compared to vehicle treated controls. The phosphorylation of the CDKL5 downstream target, EB2, confirms that the CDKL5 is acting as a functional kinase.

As shown in FIG. 7, CDKL5-deficient mice treated with rAAV9-SYN-hCDKL5 or rAAV9-CBA-hCDKL5 exhibited increased levels of CDKL5 protein as well as phosphorylated EB2 (pEB2) protein in comparison to vehicle control. Phosphorylation of the CDKL5 downstream target, EB2, confirms that the delivered CDKL5 is acting as a functional kinase.

Example 6

The purpose of this example is to demonstrate that AAV9-CBA-eGFP and AAV9-SYN-eGFP are capable of transducing cells across the non-human primate (NHP) brain after lumbar intrathecal delivery.

In this example, young female NHP subjects (n=2/vector) were administered rAAV9-CBA-eGFP or rAAV9-SYN-eGFP by lumbar intrathecal injection. At two weeks post-dosing, a variety of tissues were retrieved for vector genome quantification by quantitative PCR.

Figure 8:
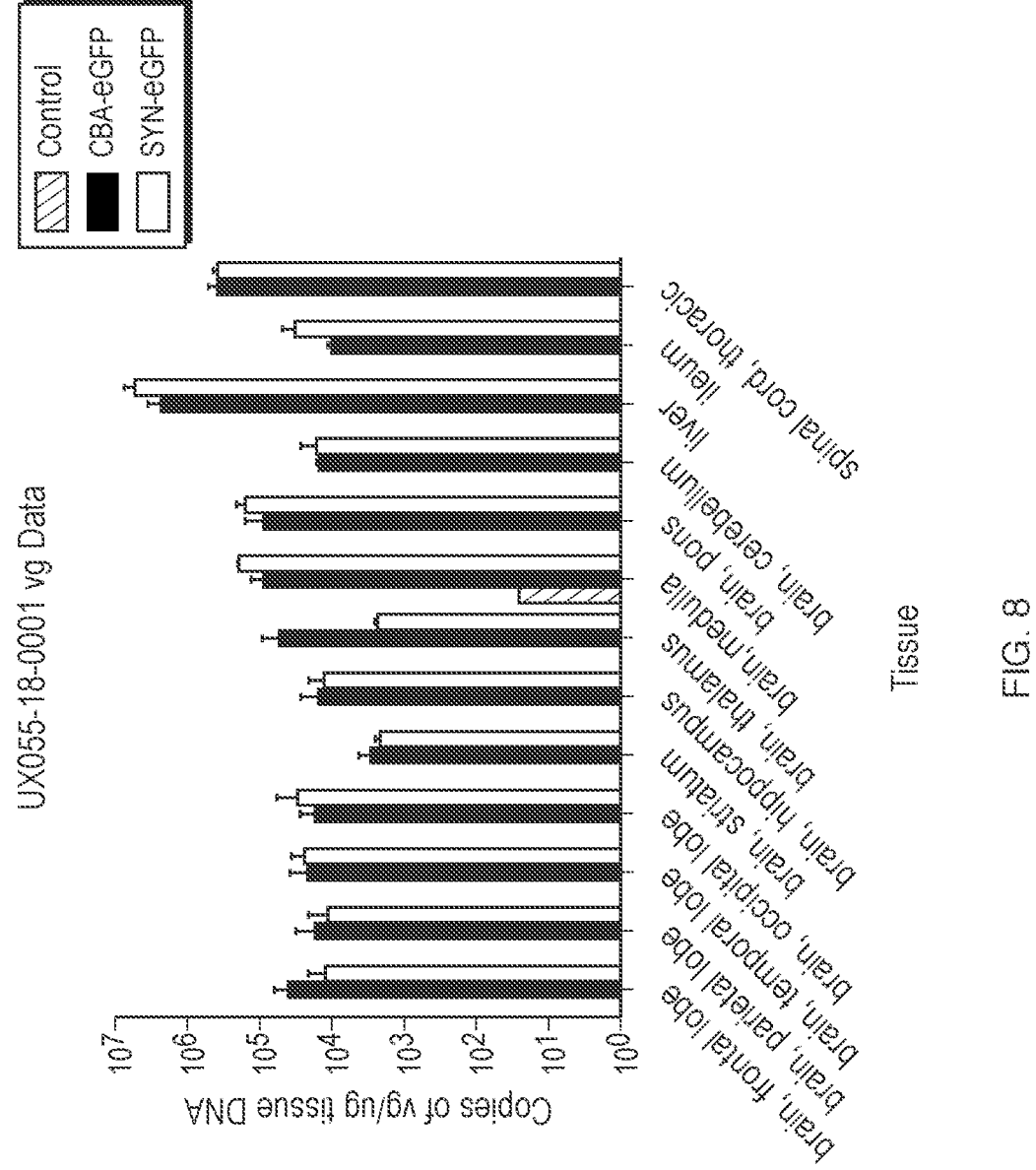
FIG. 8 is a bar graph showing quantifications of the number of copies of vector genomes per μg of tissue DNA in CNS and peripheral tissue from non-human primate (NHP) subjects 2 weeks after they were administered rAAV9-CBA-eGFP (CBA-eGFP) or rAAV9-SYN-eGFP (SYN-eGFP) by lumbar intrathecal injection. Both vectors yielded similar amounts of vector genomes per tissue. In each set of bars, CBA-eGFP is shown as the left bar (or in the case of the medulla, the middle bar) while SYN-eGFP is shown as the right bar.

Between $1\times10^3$ and $1\times10^7$ copies of vg/µg tissue DNA were quantified in CNS and peripheral tissues from treated NHPs. As shown in FIG. 8, both rAAV9-CBA-eGFP and rAAV9-SYN-eGFP administrations yielded similar copy numbers between the different tissues.

This example shows that administration of rAAV9-CBA-eGFP and rAAV9-SYN-eGFP by intrathecal delivery yields vector genomes in all brain and peripheral regions analyzed with no distinction in broad biodistribution between vector.

Example 7

The purpose of this example is to demonstrate that, in the NHP cortex, AAV9-CBA-eGFP drives expression primarily in cells with glial morphology while AAV9-SYN-eGFP drives expression primarily in cells with neuronal morphology.

In this example, young female NHP subjects (n=2/vector) were administered rAAV9-CBA-eGFP or rAAV9-SYN-eGFP by lumbar intrathecal injection. At two weeks post-dosing, the brains were retrieved, fixed, sectioned, and immunostained for eGFP by free-floating chromogenic detection.

eGFP positive cells were detected in brains sections from NHP subjects dosed with both rAAV9-CBA-eGFP and rAAV9-SYN-eGFP. eGFP-positive cells were most commonly seen singly, though were sometimes seen in clusters.

Figure 9:
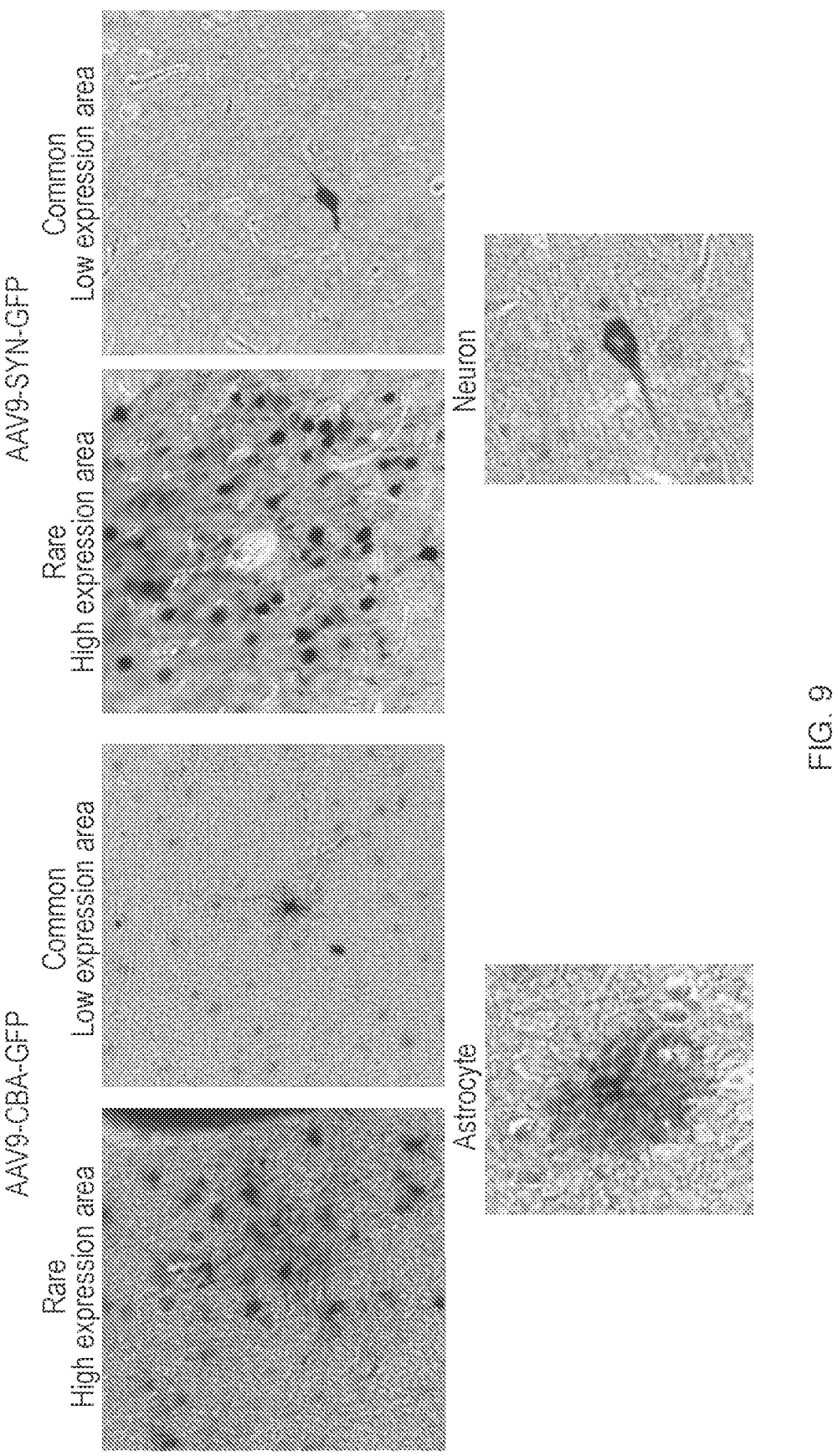
FIG. 9 is an image showing representative bright-field microscopy images from brain tissue immunostained for eGFP from NHP subjects 2 weeks after they were administered rAAV9-CBA-eGFP (left 3 panels) or rAAV9-SYN-eGFP (right 3 panels) by lumbar intrathecal injection. eGFP-positive cells from subjects dosed with rAAV9-CBA-eGFP had astrocytic/glial morphology (bottom left panel) while eGFP-positive cells from subjects dosed with rAAV9-SYN-eGFP had neuronal morphology (bottom right panel).

As shown in FIG. 9, eGFP-positive cells from NHP subjects dosed with rAAV9-CBA-eGFP had a variety of morphologies, though most had the appearance of glial cells with broad arborizations and small cell bodies, suggesting that the CBA promoter preferentially expresses the eGFP payload in astrocytic glial cells (i.e., non-neuronal cells). Meanwhile, eGFP-positive cells from NHP subjects dosed with rAAV9-SYN-eGFP had the appearance of neurons with rounded cell bodies and less arborization, suggesting that the SYN promoter is more effective at expressing the eGFP payload in the desired target cell type (i.e., neurons).

Administration of rAAV9-CBA-eGFP by intrathecal dosing largely yields eGFP-positive astrocytic glial cells while administration of rAAV9-SYN-eGFP largely yields eGFP-positive neurons. The data in this example suggests that in non-human primates, the SYN promoter may be advantageous for the delivery and expression of CDKL5 in neuronal cells relative to the constitutive CBA promoter.

Example 8

The purpose of this example is to demonstrate that rAAV9-SYN-hCDKL5 delivery to the CSF of juvenile CDKL5-deficient mice can improve learning, memory, and motor function.

In this example, a single high dose (1.6e12 vg/mouse) of a recombinant AAV comprising an AAV9 capsid and a vector genome expressing the human CDKL5 gene under the control of the SYN promoter (packaged genome illustrated in FIG. 1, SEQ ID NO: 19, 3,828 bp) was injected into the CSF of juvenile male and female CDKL5-deficient mice between 3-5 weeks of age (early symptomatic) by intracerebroventricular (ICV) injection. Once the mice reached 2-3 months of age (adulthood) they underwent a battery of behavioral tests. Following behavioral testing, brains were harvested for western blot analysis of CDKL5 protein expression.

Figures 10A, 10B, 10C:
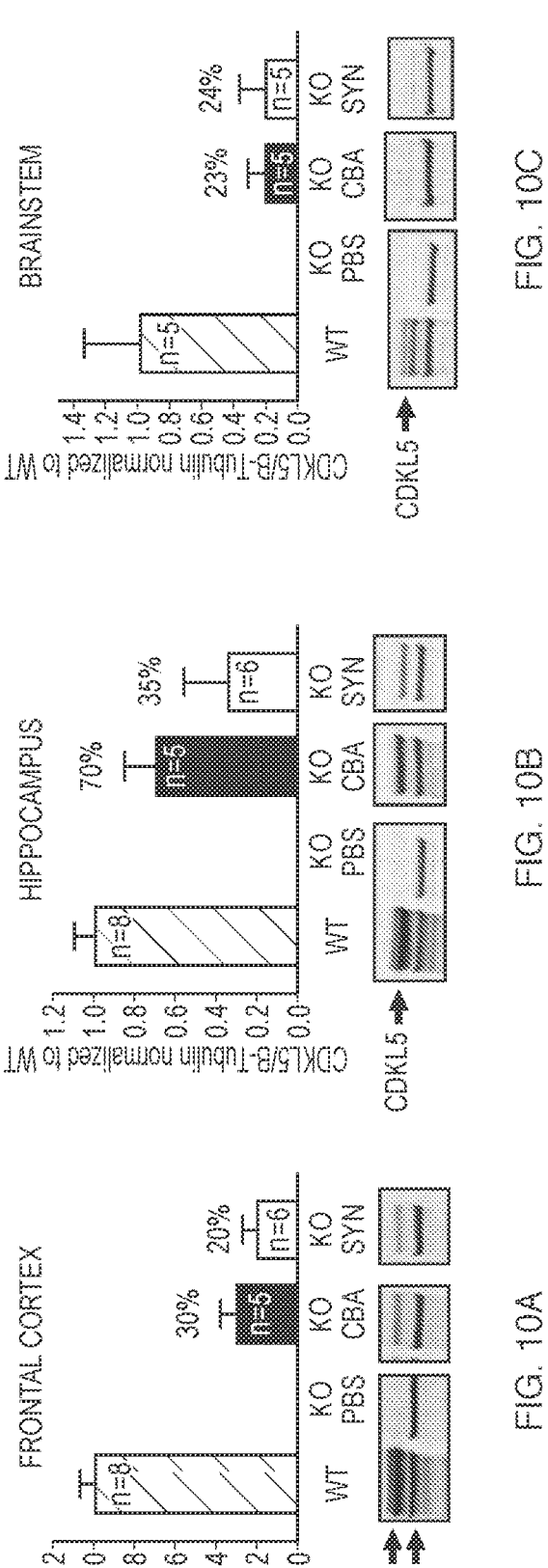
FIGS. 10A-10C shows graphs which display the amount of CDKL5 quantified in different regions (frontal cortex.

Western blot analysis of microdissected tissue from multiple brain regions demonstrated moderate long-lasting increases in human CDKL5 protein across the brain of treated mice (20-30% of WT levels in frontal cortex and brainstem, 35-70% in hippocampus) approximately 3-months after dosing. See FIGS. 10A-10C showing graphs which display the amount of CDKL5 quantified in different regions (frontal cortex: FIG. 10A; hippocampus: FIG. 10B; and brainstem: FIG. 10C) of the CDKL5-deficient mouse brain. And as shown in FIGS. 11A-11D, rAAV9-SYN-hCDKL5 treated male and female mice showed improvements in anxiety-like behavior (FIG. 11A), motor function (FIG. 11B) and coordination (FIG. 11C), as well as normalization in learning and memory (FIG. 11D).

The findings highlighted in this example suggest that even moderate levels of functional CDKL5, when delivered via rAAV9-SYN-hCDKL5 to juvenile symptomatic CDKL5-deficient mice, can lead to significantly improved brain function.

Example 9

The purpose of this example is to demonstrate that rAAV9-SYN-eGFP delivery to several CNS regions of non-human primates (NHPs) can be increased by administration of vector particles through an intracisterna magna route of administration in comparison to lumbar intrathecal administration.

Figure 12:
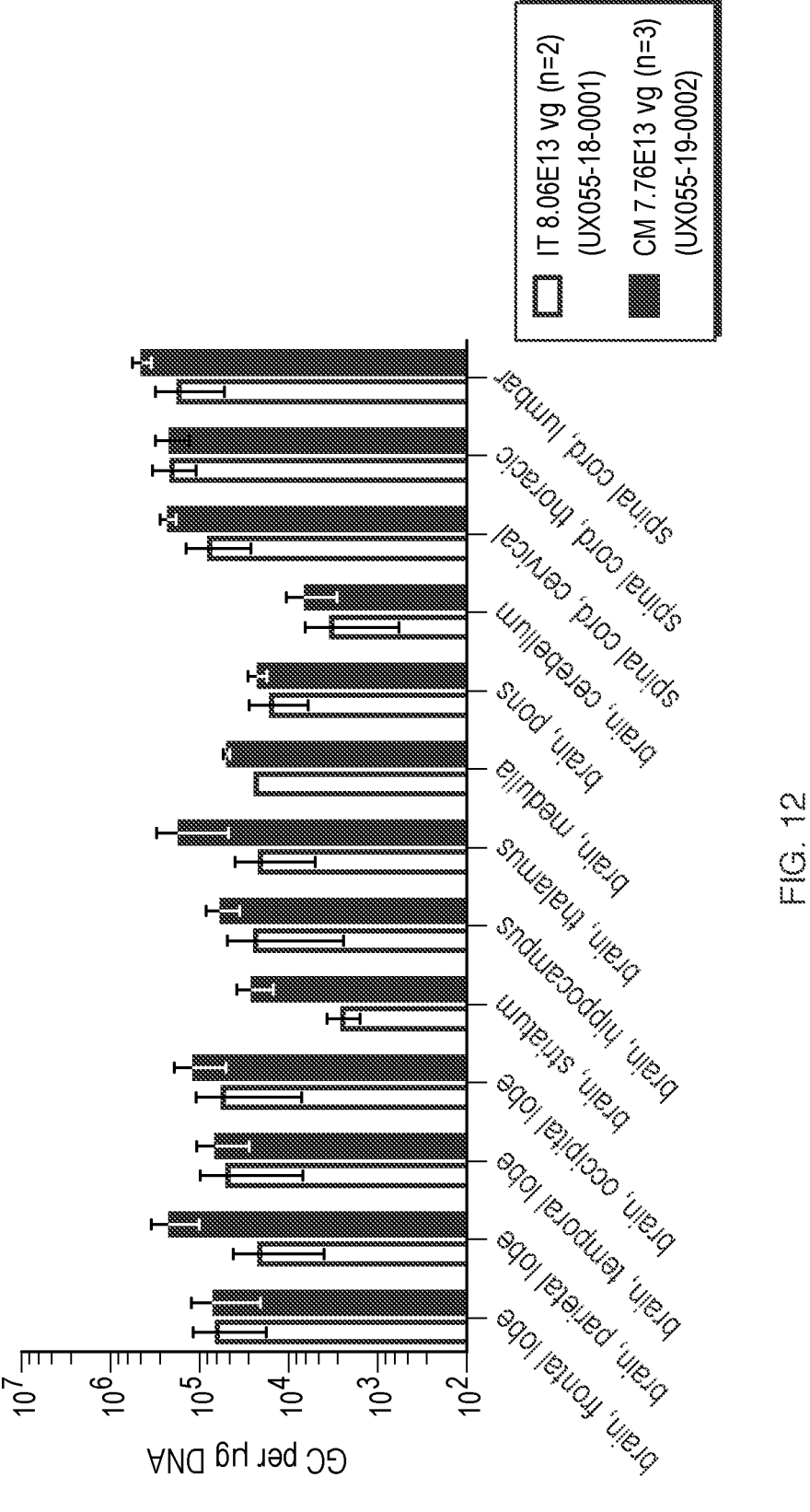
FIG. 12 is a bar graph illustrating genome copies (GC) per μg of DNA in the CNS of 1-2 year old female non-human primates (NHPs) two weeks after either intrathecal (IT) delivery (UX055-18-0001) of $8.06\times10^{13}$ vector genomes (vg) or intracisterna magna (CM) delivery (UX055-19-

In this example, young female NHP subjects were administered rAAV9-SYN-eGFP by lumbar intrathecal (IT) injection (n=2) (data extracted from Example 6 above) or by intracisterna magna (CM) administration (n=3) (data newly generated in this Example 9). All NHPs were placed in the Trendelenburg position during dosing and for 15 min after dosing was complete. At two weeks post-dosing, a variety of tissues were retrieved for vector genome quantification by quantitative PCR. FIG. 12 is a bar graph illustrating genome copies (GC) per μg of DNA in the CNS of 1-2 year old female non-human primates (NHPs) two weeks after either intrathecal (IT) delivery (UX055-18-0001) of 8.06×1013 vector genomes (vg) or intracisterna magna (CM) delivery (UX055-19-0002) of 7.76×1013 vg of rAAV9-SYN-eGFP given in the Trendelenburg position. The graph illustrates that intracisternal magna delivery results in increased numbers of vector genomes in the NHP CNS in a variety of brain tissues, including the parietal lobe (10×), striatum (10×), and thalamus (8×). The data presented in this graph were collected as part of two independent studies Between $1\times10^3$ and $1\times10^6$ copies of vg/μg tissue DNA were quantified in brain and spinal cord tissues from treated NHPs. As shown in FIG. 12, rAAV9-SYN-eGFP administration to the cisterna magna yielded higher copy numbers than lumbar intrathecal delivery across many CNS tissues.

The findings highlighted in this example indicate that increased rAAV delivery to several CNS regions in NHPs can be achieved via an intracisterna magna route of administration.

Example 10

The purpose of this example is to demonstrate that prednisolone surprisingly increases the number of rAAV9-SYN-hCDKL5 (UX055-19-003) vector genomes delivered to many CNS regions in NHPs after intracisterna magna injection.

In this example, young female NHP subjects were administered rAAV9-SYN-hCDKL5 by intracisterna magna (CM) administration in the Trendelenburg position with (n=3) or without prednisolone (n=3). NHPs in the prednisolone treatment group received a single daily dose of 1 mg/kg prednisolone by oral gavage starting 4 days before rAAV9-SYN-hCDKL5 dosing and continued until the end of the study. At four weeks post-dosing, a variety of tissues were retrieved for vector genome quantification by quantitative PCR from one half of the brain and the other half of the brain was sectioned coronally for analysis of the number of cells transduced using in situ hybridization. Probes were designed to specifically bind to the vector DNA and a hematoxylin counter stain was used to visualize individual cells.

Between $1\times10^3$ and $1\times10^6$ copies of vg/μg tissue DNA were quantified in several brain regions, spinal cord, and dorsal root ganglia (DRG) from treated NHPs. As shown in FIG. 13A, pretreatment and sustained prednisolone, when combined with rAAV9-SYN-hCDKL5 administration to the cisterna magna, surprisingly led to higher copy numbers compared to rAAV9-SYN-hCDKL5 alone across many CNS tissues. These results were surprising as an increase in transduction was not expected.

As shown in FIG. 13B, BaseScope (in situ hybridization) analysis on sections containing the occipital cortex and cerebellum demonstrated a trend toward increased numbers of cells transduced in NHPs treated with prednisolone (panels 2 and 4), however, significant animal to animal variability was seen with one outlier NHP in the non prednisolone group (panels 1 and 3). As shown in FIG. 13C, one outlier NHP with very high numbers of vector genome positive cells was noted in the non prednisolone group.

Without being bound by theory, it is hypothesized that prednisolone's ability to inhibit the innate immune system may contribute to this finding, and/or that prednisolone's ability to suppress inflammation may allow the rAAV to penetrate deeper into the brain resulting in the observed increase in transduction as measured by vector genome copy numbers.

The findings highlighted in this example indicate that increased rAAV delivery to several CNS regions in NHPs can be achieved when the corticosteroid prednisolone is given prior to and during rAAV administration.

NUMBERED EMBODIMENTS

Embodiments disclosed herein include embodiments P1 to P53 as provided in the numbered embodiments of the disclosure.

Embodiment P1: A recombinant adeno-associated virus (rAAV), wherein said rAAV comprises an AAV capsid and a vector genome packaged therein, wherein said vector genome comprises:

(a) a promoter sequence; and (b) a coding sequence for CDKL5, wherein said coding sequence comprises a sequence which is at least 95% identical to SEQ ID NOs: 1-8.

Embodiment P2: The rAAV according to embodiment P1, wherein the AAV capsid is from an AAV of serotype 1, 2, 3, 4, 5, 6, 7, 8, 9, 10, 11, 12, rh10, or hu37.

Embodiment P3: The rAAV according to embodiment P2, wherein the AAV capsid is from AAV9.

Embodiment P4: The rAAV according to embodiment P2, wherein the AAV capsid is from AAV8.

Embodiment P5: The rAAV according to embodiment P1, wherein the AAV capsid is an AAV9 variant capsid.

Embodiment P6: The rAAV according to any of embodiments P1-P5, wherein the promoter is a neuron-specific promoter.

Embodiment P7: The rAAV according to embodiment P6, wherein the neuron-specific promoter is selected from a human synapsin 1 (SYN1) promoter, a mouse calcium/calmodulin-dependent protein kinase II (CaMKII) promoter, a rat tubulin alpha I (Ta1) promoter, a rat neuron-specific enolase (NSE) promoter, a human neuron-specific enolase (ENO2) promoter, a human platelet-derived growth factor-beta chain (PDGF) promoter, a human BM88 promoter, and a neuronal nicotinic receptor β2 (CHRNB2) promoter.

Embodiment P8: The rAAV according to embodiment P7, wherein the neuron-specific promoter is the SYN1 promoter.

Embodiment P9: The rAAV according to embodiment P8, wherein the SYN1 promoter sequence comprises SEQ ID NO: 12.

Embodiment P10: The rAAV according to embodiment P8, wherein the SYN1 promoter sequence consists of SEQ ID NO: 12.

Embodiment P11: The rAAV according to any of embodiments P1-P5, wherein the promoter is selected from a chicken β-actin (CBA) promoter, a cytomegalovirus (CMV) immediate early gene promoter, a transthyretin (TTR) promoter, a thyroxine binding globulin (TBG) promoter, and an alpha-1 anti-trypsin (A1AT) promoter.

Embodiment P12: The rAAV according to embodiment P11, wherein the promoter is the CBA promoter.

Embodiment P13: The rAAV according to embodiment P12, wherein the CBA promoter sequence comprises SEQ ID NO: 13.

Embodiment P14: The rAAV according to embodiment P12, wherein the CBA promoter sequence consists of SEQ ID NO: 13.

Embodiment P15: The rAAV according to any of embodiments P1-P5, wherein the promoter is a CDKL5 gene-specific endogenous promoter.

Embodiment P16: The rAAV according to embodiment P15, wherein the CDKL5 gene-specific endogenous promoter comprises a nucleotide sequence of at least 15 continuous nucleotides which is at least 95% identical to an equal length region of SEQ ID NO: 14.

Embodiment P17: The rAAV according to any of embodiments P1-P16, wherein the vector genome further comprises a 5'-ITR sequence.

Embodiment P18: The rAAV according to any of embodiments P1-P17, wherein the vector genome further comprises a 3'-ITR sequence.

Embodiment P19: The rAAV according to any of embodiments P17-P18, wherein the 5'-ITR sequence and/or the 3'-ITR sequence are from AAV2.

Embodiment P20: The rAAV according to embodiment P19, wherein the 5'-ITR sequence and the 3'-ITR sequence comprise or consist of SEQ ID NO: 11.

Embodiment P21: The rAAV according to any of embodiments P17-P18, wherein the 5'-ITR sequence and/or the 3'-ITR sequence are from a non-AAV2 source.

Embodiment P22: The rAAV according to any of embodiments P1-P21, wherein the vector genome further comprises a polyadenylation signal sequence.

Embodiment P23: The rAAV according to embodiment P22, wherein the polyadenylation signal sequence is selected from an SV40 polyadenylation signal sequence, a bovine growth hormone (BGH) polyadenylation signal sequence, and a rabbit beta globin polyadenylation signal sequence.

Embodiment P24: The rAAV according to embodiment P23, wherein the polyadenylation signal sequence is the SV40 polyadenylation signal sequence.

Embodiment P25: The rAAV according to embodiment P24, wherein the SV40 polyadenylation signal sequence comprises or consists of SEQ ID NO: 15.

Embodiment P26: The rAAV according to any of embodiments P1-P25, wherein the vector genome further comprises one or more enhancer sequences.

Embodiment P27: The rAAV according to embodiment P26, wherein the enhancer is selected from a cytomegalovirus (CMV) immediate early gene enhancer, a transthyretin enhancer (enTTR), a chicken β-actin (CBA) enhancer, an En34 enhancer, and an apolipoprotein E (ApoE) enhancer.

Embodiment P28: The rAAV according to embodiment P27, wherein the enhancer is the CMV enhancer.

Embodiment P29: The rAAV according to embodiment P28, wherein the enhancer sequence comprises or consists of SEQ ID NO: 17.

Embodiment P30: The rAAV according to embodiments P26-P29, wherein the enhancer is located upstream of the promoter sequence.

Embodiment P31: The rAAV according to any of embodiments P1-P30, wherein the vector genome further comprises one or more intron sequences.

Embodiment P32: The rAAV according to embodiment P31, wherein the intron is selected from an SV40 Small T intron, a rabbit hemoglobin subunit beta (rHBB) intron, a human beta globin IVS2 intron, a β-globin/IgG chimeric intron, or an hFIX intron.

Embodiment P33: The rAAV according to embodiment P32, wherein the intron is the SV40 Small T intron.

Embodiment P34: The rAAV according to embodiment P33, wherein the SV40 Small T intron sequence comprises or consists of SEQ ID NO: 18.

Embodiment P35: A composition comprising the rAAV of any of the preceding embodiments and a pharmaceutically acceptable carrier.

Embodiment P36: A method of treating CDKL5 deficiency disorder (CDD) in a human subject comprising administering to the human subject a therapeutically effective amount of an rAAV of any of embodiments P1-P34 or a composition of embodiment P35.

Embodiment P37: The method of embodiment P36, wherein the rAAV or the composition is administered subcutaneously, intramuscularly, intradermally, intraperitoneally, intrathecally, intracerebroventricularly, intravenously, or intracisterna magna.

Embodiment P38: The method of embodiment P37, wherein the rAAV or the composition is administered intrathecally.

Embodiment P39: The method of embodiment P37, wherein the rAAV or the composition is administered intracisterna magna.

Embodiment P40: The method of any of embodiments P37-P39, wherein the rAAV is administered at a dose of about $1 \times 10^{11}$ to about $1 \times 10^{14}$ genome copies (GC)/kg.

Embodiment P41: A method of treating CDKL5 deficiency disorder (CDD) in a human subject comprising first administering to the human subject a corticosteroid and then subsequently administering a therapeutically effective amount of a recombinant adeno-associated virus (rAAV), wherein said rAAV comprises an AAV capsid and a vector genome packaged therein, wherein said vector genome comprises a promoter sequence and a coding sequence for CDKL5.

Embodiment P42: A method of treating CDKL5 deficiency disorder (CDD) in a human subject comprising first administering to the human subject a corticosteroid and then subsequently administering a therapeutically effective amount of an rAAV of any of embodiments P1-P34 or a composition of embodiment P35.

Embodiment P43: The method of any of embodiments P41-P42, wherein the corticosteroid is selected from prednisolone, prednisone, dexamethasone, hydrocortisone, triamcinolone, methylprednisolone, budesonide, betamethasone, and deflazacort.

Embodiment P44: The method of embodiment P43, wherein the corticosteroid is prednisolone.

Embodiment P45: A method of treating CDKL5 deficiency disorder (CDD) in a human subject comprising first administering to the human subject an IgG-degrading protease and then subsequently administering a therapeutically effective amount of an rAAV of any of embodiments P1-P34 or a composition of embodiment P35.

Embodiment P46: The method of embodiment P45, wherein the IgG-degrading protease is IdeS of *Streptococcus pyogenes* or an engineered variant thereof.

Embodiment P47: The method of embodiment P45, wherein the IgG-degrading protease is IdeZ of *Streptococcus equi* or an engineered variant thereof.

Embodiment P48: A polynucleotide which comprises a nucleic acid sequence at least 95% identical to SEQ ID NO: 19.

Embodiment P49: A polynucleotide comprising SEQ ID NO: 19.

Embodiment P50: A polynucleotide consisting of SEQ ID NO: 19.

Embodiment P51: A polynucleotide which comprises a nucleic acid sequence at least 95% identical to SEQ ID NO: 20.

Embodiment P52: A polynucleotide comprising SEQ ID NO: 20.

Embodiment P53: A polynucleotide consisting of SEQ ID NO: 20.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Various structural elements of the different embodiments and various disclosed method steps may be utilized in various combinations and permutations, and all such variants are to be considered forms of the disclosure. Scope of the disclosure is thus indicated by the appended claims rather than by the foregoing description, and all changes that come within the meaning and range of equivalency of the claims are intended to be embraced therein.

What is claimed is:

1. A recombinant adeno-associated virus (rAAV), wherein said rAAV comprises an AAV capsid and a vector genome packaged therein, wherein said vector genome comprises:

(a) a promoter sequence; and (b) a coding sequence for CDKL5, wherein said coding sequence comprises a sequence which is at least 95% identical to a sequence selected from SEQ ID NOs: 1, 2, 3, 4, 5, 6, 7, and 8.

2. The rAAV according to claim 1, wherein the AAV capsid is from an AAV of serotype 8, 9, 1, 2, 3, 4, 5, 6, 7, 10, 11, 12, rh10, AAV9 variant, or hu37.

3. The rAAV according to claim 1, wherein the promoter sequence is any one of:

(i) a neuron-specific promoter sequence selected from any one of a human synapsin 1 (SYN1) promoter sequence, a mouse calcium/calmodulin-dependent protein kinase II (CaMKII) promoter sequence, a rat tubulin alpha I (Ta1) promoter sequence, a rat neuron-specific enolase (NSE) promoter sequence, a human neuron-specific enolase (ENO2) promoter sequence, a human platelet-derived growth factor-beta chain (PDGF) promoter sequence, a human BM88 promoter sequence, and a neuronal nicotinic receptor β2 (CHRNB2) promoter sequence; and (ii) a chicken β-actin (CBA) promoter sequence, a cyto-megalovirus (CMV) immediate early gene promoter sequence, a transthyretin (TTR) promoter sequence, a thyroxine binding globulin (TBG) promoter sequence, an alpha-1 anti-trypsin (A1AT) promoter sequence, and a CDKL5 gene-specific endogenous promoter sequence.

4. The rAAV according to claim 3, wherein the neuron-specific promoter sequence is selected from any one of:

(a) a human synapsin 1 (SYN1) promoter sequence comprising the sequence of SEQ ID NO: 12, (b) a human SYN1 promoter sequence consisting of SEQ ID NO: 12, (c) a CBA promoter sequence comprising the sequence of SEQ ID NO: 13, (d) a CBA promoter sequence consisting of SEQ ID NO: 13, and (e) a CDKL5 gene-specific endogenous promoter that comprises a nucleotide sequence of at least 15 continuous nucleotides which is at least 95% identical to an equal length region of the sequence of SEQ ID NO: 14.

5. The rAAV according to claim 1, wherein the vector genome further comprises a 5'-ITR sequence, a 3'-ITR sequence, or both.

6. The rAAV according to claim 5, wherein:

(a) the 5'-ITR sequence and/or the 3'-ITR sequence are from an AAV2 source; or (b) the 5'-ITR sequence and/or the 3'-ITR sequence are from a non-AAV2 source.

7. The rAAV according to claim 1, wherein the vector genome further comprises a polyadenylation signal sequence selected from an SV40 polyadenylation signal sequence, a bovine growth hormone (BGH) polyadenylation signal sequence, and a rabbit beta globin polyadenylation signal sequence.

8. The rAAV according to claim 7, wherein the SV40 polyadenylation signal sequence comprises or consists of the nucleic acid sequence of SEQ ID NO: 15.

9. The rAAV according to claim 1, wherein the vector genome further comprises one or more enhancer sequences selected from a cytomegalovirus (CMV) immediate early gene enhancer sequence, a transthyretin enhancer (enTTR) sequence, a chicken β-actin (CBA) enhancer sequence, an En34 enhancer sequence, and an apolipoprotein E (ApoE) enhancer sequence.

10. The rAAV according to claim 9, wherein the enhancer sequence is located upstream of the promoter sequence.

11. The rAAV according to claim 1, wherein the vector genome further comprises one or more intron sequences selected from an SV40 Small T intron sequence, a rabbit hemoglobin subunit beta (rHBB) intron sequence, a human beta globin IVS2 intron sequence, a β-globin/IgG chimeric intron sequence, and an hFIX intron sequence.

12. A composition comprising the rAAV of claim 1 and a pharmaceutically acceptable carrier.

13. A polynucleotide which comprises a nucleic acid sequence that is:

(a) at least 95% identical to the sequence of SEQ ID NO: 19;

(b) 100% identical to the sequence of SEQ ID NO: 19;

(c) at least 95% identical to the sequence of SEQ ID NO: 20; or (d) 100% identical to the sequence of SEQ ID NO: 20.

14. The rAAV according to claim 5, wherein the 5'-ITR sequence and/or the 3'-ITR sequence are from an AAV2 source and comprise the nucleic acid sequence of SEQ ID NO: 11.

15. A recombinant adeno-associated virus (rAAV), wherein said rAAV comprises an AAV capsid and a vector genome packaged therein, wherein said vector genome comprises:

(a) an AAV 5'-inverted terminal repeat (ITR) sequence of SEQ ID NO: 11;

(b) a human synapsin 1 (SYN1) promoter sequence of SEQ ID NO: 12;

(c) a nucleic acid sequence of SEQ ID NO: 1 encoding CDKL5;

(d) an SV40 polyadenylation signal sequence of SEQ ID NO: 15; and (e) an AAV 3'-ITR sequence of SEQ ID NO: 11.

* * * * *